(12) United States Patent
Yaniv et al.

(10) Patent No.: US 8,934,975 B2
(45) Date of Patent: Jan. 13, 2015

(54) GASTROINTESTINAL ELECTRICAL THERAPY

(75) Inventors: Irit Yaniv, Ramat Gan (IL); Walid Haddad, Haifa (IL); Paul V. Goode, Jr., Cherry Hill, NJ (US); Harold Lebovitz, Staten Island, NY (US); Ricardo Aviv, Vienna (AU); Benny Rousso, Rishon Le Zion (IL); Shlomo Ben-Haim, Orangeburg, NY (US)

(73) Assignee: Metacure Limited, Hamilton (BM)

( * ) Notice: Subject to any disclaimer, the term of this patent is extended or adjusted under 35 U.S.C. 154(b) by 62 days.

(21) Appl. No.: 13/576,485

(22) PCT Filed: Feb. 1, 2011

(86) PCT No.: PCT/IL2011/000116
§ 371 (c)(1),
(2), (4) Date: Oct. 16, 2012

(87) PCT Pub. No.: WO2011/092710
PCT Pub. Date: Aug. 4, 2011

(65) Prior Publication Data
US 2013/0030503 A1    Jan. 31, 2013

Related U.S. Application Data

(60) Provisional application No. 61/300,292, filed on Feb. 1, 2010, provisional application No. 61/406,774, filed on Oct. 26, 2010.

(51) Int. Cl.
*A61N 1/40* (2006.01)
*A61N 1/36* (2006.01)
*A61N 1/05* (2006.01)

(52) U.S. Cl.
CPC ........ *A61N 1/36139* (2013.01); *A61N 1/36007* (2013.01); *A61N 1/36085* (2013.01); *A61N 1/0509* (2013.01); *A61N 1/36053* (2013.01)
USPC .......................................................... 607/40

(58) Field of Classification Search
CPC ....... A61N 1/36007; A61N 1/00; A61N 1/08; A61B 5/053; A61B 5/4238; A61B 5/6871; A61F 5/0026; A61F 5/0036
USPC ..................................................... 607/2, 9, 40
See application file for complete search history.

(56) References Cited

U.S. PATENT DOCUMENTS

| 1,918,386 A | 7/1933 | Esau |
| 2,593,067 A | 4/1952 | Spencer |

(Continued)

FOREIGN PATENT DOCUMENTS

| EP | 0057048 | 8/1982 |
| EP | 0129483 | 12/1984 |

(Continued)

OTHER PUBLICATIONS

Applicant-Initiated Interview Summary Dated Feb. 4, 2014 From the US Patent and Trademark Office Re. U.S. Appl. No. 11/884,389.

(Continued)

*Primary Examiner* — Rex R Holmes
(74) *Attorney, Agent, or Firm* — William H. Dippert; Eckert Seamans Cherin & Mellott, LLC

(57) ABSTRACT

Apparatus (18) for treating a human patient, which includes one or more electrode contact surfaces (100), which are configured to be applied to a fundus (22) of the patient. A control unit (90) is configured to drive the one or more electrode contact surfaces (100) to apply an electrical signal to the fundus (22) that chronically improves a blood glucose level of the patient, in order to treat the patient, without calculating an impedance of tissue of the fundus (22) based on a sensed parameter that varies in response to the electrical signal, for detecting eating by the patient or a characteristic of food eaten by the patient. Other embodiments are also described.

66 Claims, 12 Drawing Sheets

(56) References Cited

U.S. PATENT DOCUMENTS

| | | |
|---|---|---|
| 3,211,154 A | 10/1965 | Becker et al. |
| 3,411,507 A | 11/1968 | Wingrove |
| 3,587,567 A | 12/1968 | Schiff |
| 3,516,412 A | 6/1970 | Ackerman |
| 3,541,390 A | 11/1970 | Jahnke |
| 3,572,345 A | 3/1971 | Auphan |
| 3,650,277 A | 3/1972 | Sjostrand et al. |
| 3,651,805 A | 3/1972 | Brelling |
| 3,651,806 A | 3/1972 | Hirshberg |
| 3,658,051 A | 4/1972 | MacLean |
| 3,737,579 A | 6/1973 | Bolduc |
| 3,796,221 A | 3/1974 | Hagfors |
| 3,911,930 A | 10/1975 | Hagfors et al. |
| 3,924,641 A | 12/1975 | Weiss |
| 3,933,147 A | 1/1976 | Du Vall et al. |
| 3,942,536 A | 3/1976 | Mirowski et al. |
| 3,944,740 A | 3/1976 | Murase et al. |
| 3,952,750 A | 4/1976 | Mirowski et al. |
| 4,000,745 A | 1/1977 | Goldberg et al. |
| 4,010,758 A | 3/1977 | Rockland et al. |
| 4,030,509 A | 6/1977 | Heilman et al. |
| 4,055,190 A | 10/1977 | Tany |
| 4,106,494 A | 8/1978 | McEachern |
| 4,133,315 A | 1/1979 | Berman et al. |
| 4,164,216 A | 8/1979 | Person |
| 4,165,454 A | 8/1979 | Carlsson et al. |
| 4,168,711 A | 9/1979 | Cannon, III et al. |
| 4,177,818 A | 12/1979 | De Pedro |
| 4,184,493 A | 1/1980 | Langer et al. |
| 4,202,340 A | 5/1980 | Langer et al. |
| 4,223,678 A | 9/1980 | Langer et al. |
| 4,235,246 A | 11/1980 | Weiss |
| 4,237,895 A | 12/1980 | Johnson |
| 4,273,114 A | 6/1981 | Berkalow et al. |
| 4,280,503 A | 7/1981 | Ackerman |
| 4,293,734 A | 10/1981 | Pepper, Jr. |
| 4,312,354 A | 1/1982 | Walters |
| 4,313,448 A | 2/1982 | Stokes |
| 4,315,503 A | 2/1982 | Ryaby et al. |
| 4,316,472 A | 2/1982 | Mirowski et al. |
| 4,337,776 A | 7/1982 | Daly et al. |
| 4,342,896 A | 8/1982 | Teich |
| 4,354,153 A | 10/1982 | Lentz |
| 4,357,946 A | 11/1982 | Dutcher et al. |
| 4,369,791 A | 1/1983 | Friedman |
| 4,377,733 A | 3/1983 | Yamaguchi et al. |
| 4,378,023 A | 3/1983 | Trabucco |
| 4,384,585 A | 5/1983 | Zipes |
| 4,387,717 A | 6/1983 | Brownlee et al. |
| 4,403,614 A | 9/1983 | Engle et al. |
| 4,406,288 A | 9/1983 | Horwinski et al. |
| 4,407,288 A | 10/1983 | Langer et al. |
| 4,411,268 A | 10/1983 | Cox |
| 4,416,267 A | 11/1983 | Garren et al. |
| 4,428,366 A | 1/1984 | Findl et al. |
| 4,431,888 A | 2/1984 | Simpson |
| 4,440,172 A | 4/1984 | Langer |
| 4,447,693 A | 5/1984 | Buck |
| 4,452,254 A | 6/1984 | Goldberg et al. |
| 4,475,024 A | 10/1984 | Tateda |
| 4,485,805 A | 12/1984 | Foster, Jr. |
| 4,506,680 A | 3/1985 | Stokes |
| 4,537,195 A | 8/1985 | McDonnell |
| 4,537,203 A | 8/1985 | Machida |
| 4,543,738 A | 10/1985 | Mower |
| 4,543,956 A | 10/1985 | Herscovici |
| 4,550,221 A | 10/1985 | Mabusth |
| 4,552,150 A | 11/1985 | Zacouto |
| 4,554,922 A | 11/1985 | Prystowsky et al. |
| 4,554,992 A | 11/1985 | Kassai |
| 4,559,946 A | 12/1985 | Mower |
| 4,559,947 A | 12/1985 | Renger et al. |
| 4,566,456 A | 1/1986 | Koning et al. |
| 4,572,191 A | 2/1986 | Mirowski et al. |
| 4,592,339 A | 6/1986 | Kuzmak |
| 4,596,915 A | 6/1986 | Simpson |
| 4,628,934 A | 12/1986 | Pohndorf et al. |
| 4,637,397 A | 1/1987 | Jones et al. |
| 4,639,720 A | 1/1987 | Rympalski et al. |
| 4,651,716 A | 3/1987 | Forester et al. |
| 4,674,508 A | 6/1987 | DeCote |
| 4,679,572 A | 7/1987 | Baker, Jr. |
| 4,686,332 A | 8/1987 | Greanias et al. |
| 4,690,155 A | 9/1987 | Hess |
| 4,693,253 A | 9/1987 | Adams |
| 4,696,288 A | 9/1987 | Kuzmak |
| 4,708,145 A | 11/1987 | Tacker et al. |
| 4,717,581 A | 1/1988 | Robblee |
| 4,726,279 A | 2/1988 | Kepler et al. |
| 4,726,379 A | 2/1988 | Altman et al. |
| 4,765,341 A | 8/1988 | Mower et al. |
| 4,807,632 A | 2/1989 | Liess et al. |
| 4,823,808 A | 4/1989 | Clegg et al. |
| 4,830,006 A | 5/1989 | Haluska et al. |
| 4,834,100 A | 5/1989 | Charms |
| 4,850,959 A | 7/1989 | Findl |
| 4,870,974 A | 10/1989 | Wang |
| 4,873,986 A | 10/1989 | Wallace |
| 4,878,553 A | 11/1989 | Yamanami et al. |
| 4,884,576 A | 12/1989 | Alt |
| 4,914,624 A | 4/1990 | Dunthorn et al. |
| 4,928,688 A | 5/1990 | Mower |
| 4,967,749 A | 11/1990 | Cohen |
| 4,971,058 A | 11/1990 | Pless et al. |
| 4,975,682 A | 12/1990 | Kerr et al. |
| 4,979,507 A | 12/1990 | Heinz et al. |
| 4,988,837 A | 1/1991 | Murakami et al. |
| 4,996,984 A | 3/1991 | Sweeney |
| 4,998,531 A | 3/1991 | Bocchi et al. |
| 4,998,532 A | 3/1991 | Griffith |
| 5,002,052 A | 3/1991 | Haluska et al. |
| 5,003,976 A | 4/1991 | Alt |
| 5,018,522 A | 5/1991 | Mehra |
| 5,020,544 A | 6/1991 | Dahl et al. |
| 5,022,396 A | 6/1991 | Watanabe |
| 5,025,787 A | 6/1991 | Sutherland et al. |
| 5,026,397 A | 6/1991 | Aoki et al. |
| 5,031,617 A | 7/1991 | Klettner |
| 5,041,107 A | 8/1991 | Heil, Jr. |
| 5,044,375 A | 9/1991 | Bach, Jr. et al. |
| 5,048,522 A | 9/1991 | Petrofsky |
| 5,050,612 A | 9/1991 | Matsumura |
| 5,063,929 A | 11/1991 | Bartelt et al. |
| 5,074,868 A | 12/1991 | Kuzmak |
| 5,083,564 A | 1/1992 | Scherlag |
| 5,083,565 A | 1/1992 | Parins |
| 5,085,218 A | 2/1992 | Heil et al. |
| 5,087,243 A | 2/1992 | Avitall |
| 5,097,832 A | 3/1992 | Buchanan |
| 5,097,833 A | 3/1992 | Campos |
| 5,097,843 A | 3/1992 | Soukup et al. |
| 5,101,814 A | 4/1992 | Palti |
| 5,103,804 A | 4/1992 | Abele |
| 5,105,812 A | 4/1992 | Corman |
| 5,107,834 A | 4/1992 | Ideker et al. |
| 5,111,814 A | 5/1992 | Goldfarb |
| 5,111,815 A | 5/1992 | Mower |
| 5,129,394 A | 7/1992 | Mehra |
| 5,133,354 A | 7/1992 | Kallok |
| 5,137,021 A | 8/1992 | Wayne et al. |
| 5,144,554 A | 9/1992 | Zhang et al. |
| 5,154,501 A | 10/1992 | Svenson et al. |
| 5,156,147 A | 10/1992 | Warren et al. |
| 5,156,149 A | 10/1992 | Hudrlik |
| 5,161,527 A | 11/1992 | Nappholz et al. |
| 5,163,427 A | 11/1992 | Keimel |
| 5,163,428 A | 11/1992 | Pless |
| 5,172,690 A | 12/1992 | Nappholz et al. |
| 5,172,699 A | 12/1992 | Svenson et al. |
| 5,174,286 A | 12/1992 | Chirife |
| 5,184,616 A | 2/1993 | Weiss |
| 5,184,620 A | 2/1993 | Cudahy et al. |
| 5,185,620 A | 2/1993 | Cooper |
| 5,188,104 A | 2/1993 | Wernicke et al. |

(56) References Cited

U.S. PATENT DOCUMENTS

| | | |
|---|---|---|
| 5,188,106 A | 2/1993 | Nappholz et al. |
| 5,190,036 A | 3/1993 | Linder |
| 5,190,041 A | 3/1993 | Palti |
| 5,190,141 A | 3/1993 | Boldrini et al. |
| 5,197,491 A | 3/1993 | Anderson |
| 5,199,428 A | 4/1993 | Obel et al. |
| 5,202,095 A | 4/1993 | Houchin et al. |
| 5,205,284 A | 4/1993 | Freeman |
| 5,213,098 A | 5/1993 | Bennett et al. |
| 5,226,429 A | 7/1993 | Kuzmak |
| 5,231,381 A | 7/1993 | Duwaer |
| 5,231,988 A | 8/1993 | Wernicke et al. |
| 5,233,985 A | 8/1993 | Hudrlik |
| 5,234,454 A | 8/1993 | Bangs |
| 5,236,413 A | 8/1993 | Feiring |
| 5,243,980 A | 9/1993 | Mehra et al. |
| 5,247,938 A | 9/1993 | Silverstein |
| 5,263,480 A | 11/1993 | Wernicke et al. |
| 5,267,560 A | 12/1993 | Cohen |
| 5,281,219 A | 1/1994 | Kallok |
| 5,282,785 A | 2/1994 | Shapland et al. |
| 5,284,491 A | 2/1994 | Sutton et al. |
| 5,286,254 A | 2/1994 | Shapland et al. |
| 5,292,344 A | 3/1994 | Douglas |
| 5,305,745 A | 4/1994 | Zacouto |
| 5,314,463 A | 5/1994 | Camps et al. |
| 5,318,591 A | 6/1994 | Causey, III et al. |
| 5,320,543 A | 6/1994 | Barton et al. |
| 5,320,642 A | 6/1994 | Scherlag |
| 5,320,643 A | 6/1994 | Roline et al. |
| 5,324,327 A | 6/1994 | Cohen |
| 5,325,856 A | 7/1994 | Nitzsche et al. |
| 5,327,887 A | 7/1994 | Nowakowski |
| 5,346,506 A | 9/1994 | Mower et al. |
| 5,350,403 A | 9/1994 | Stroetmann et al. |
| 5,353,800 A | 10/1994 | Pohndorf et al. |
| 5,365,461 A | 11/1994 | Stein et al. |
| 5,366,485 A | 11/1994 | Kroll et al. |
| 5,366,486 A | 11/1994 | Zipes et al. |
| 5,368,028 A | 11/1994 | Palti |
| 5,368,040 A | 11/1994 | Carney |
| 5,370,665 A | 12/1994 | Hudrlik |
| 5,374,787 A | 12/1994 | Miller et al. |
| 5,381,160 A | 1/1995 | Landmeier |
| 5,386,835 A | 2/1995 | Elphick et al. |
| 5,386,837 A | 2/1995 | Sterzer |
| 5,387,419 A | 2/1995 | Levy et al. |
| 5,391,192 A | 2/1995 | Lu et al. |
| 5,391,199 A | 2/1995 | Ben-Haim |
| 5,397,344 A | 3/1995 | Garfield et al. |
| 5,398,683 A | 3/1995 | Edwards et al. |
| 5,402,151 A | 3/1995 | Duwaer |
| 5,411,531 A | 5/1995 | Hill et al. |
| 5,415,629 A | 5/1995 | Henley |
| 5,417,717 A | 5/1995 | Salo et al. |
| 5,419,763 A | 5/1995 | Hildebrand |
| 5,423,872 A | 6/1995 | Cigaina |
| 5,425,363 A | 6/1995 | Wang |
| 5,431,682 A | 7/1995 | Hedberg |
| 5,431,688 A | 7/1995 | Freeman |
| 5,431,693 A | 7/1995 | Schroeppel |
| 5,433,730 A | 7/1995 | Alt |
| 5,443,485 A | 8/1995 | Housworth et al. |
| 5,443,489 A | 8/1995 | Ben-Haim |
| 5,445,609 A | 8/1995 | Lattin et al. |
| 5,447,520 A | 9/1995 | Spano et al. |
| 5,447,525 A | 9/1995 | Powell et al. |
| 5,447,526 A | 9/1995 | Karsdon |
| 5,449,368 A | 9/1995 | Kuzmak |
| 5,451,751 A | 9/1995 | Takimoto et al. |
| 5,458,568 A | 10/1995 | Racchini et al. |
| 5,464,020 A | 11/1995 | Lerner |
| 5,464,429 A | 11/1995 | Hedberg et al. |
| 5,468,254 A | 11/1995 | Hahn et al. |
| 5,472,453 A | 12/1995 | Alt |
| 5,476,484 A | 12/1995 | Hedberg |
| 5,476,485 A | 12/1995 | Weinberg et al. |
| 5,476,487 A | 12/1995 | Sholder |
| 5,476,497 A | 12/1995 | Mower et al. |
| 5,480,422 A | 1/1996 | Ben-Haim |
| 5,482,052 A | 1/1996 | Lerner |
| 5,489,293 A | 2/1996 | Pless et al. |
| 5,495,077 A | 2/1996 | Miller et al. |
| 5,499,971 A | 3/1996 | Shapland et al. |
| 5,501,662 A | 3/1996 | Hofmann |
| 5,505,700 A | 4/1996 | Leone et al. |
| 5,510,813 A | 4/1996 | Makinwa et al. |
| 5,514,162 A | 5/1996 | Bornzin et al. |
| 5,514,175 A | 5/1996 | Kim et al. |
| 5,520,642 A | 5/1996 | Bigagli et al. |
| 5,522,853 A | 6/1996 | Kroll |
| 5,527,345 A | 6/1996 | Infinger |
| 5,528,002 A | 6/1996 | Katabami |
| 5,531,764 A | 7/1996 | Adams et al. |
| 5,534,015 A | 7/1996 | Kroll et al. |
| 5,540,722 A | 7/1996 | Clare et al. |
| 5,540,730 A | 7/1996 | Terry, Jr. et al. |
| 5,540,734 A | 7/1996 | Zabara |
| 5,543,589 A | 8/1996 | Buchana et al. |
| 5,546,951 A | 8/1996 | Ben-Haim |
| 5,549,646 A | 8/1996 | Katz et al. |
| 5,551,425 A | 9/1996 | Essen-Moller |
| 5,552,150 A | 9/1996 | Horrobin et al. |
| 5,556,421 A | 9/1996 | Prutchi et al. |
| 5,556,425 A | 9/1996 | Hewson |
| 5,556,760 A | 9/1996 | Nakamura et al. |
| 5,558,640 A | 9/1996 | Pfeiler et al. |
| 5,561,165 A | 10/1996 | Lautt et al. |
| 5,562,708 A | 10/1996 | Combs et al. |
| 5,562,720 A | 10/1996 | Stern et al. |
| 5,565,632 A | 10/1996 | Ogawa |
| 5,568,809 A | 10/1996 | Ben-haim |
| 5,571,143 A | 11/1996 | Hoegnelid et al. |
| 5,571,997 A | 11/1996 | Gray et al. |
| 5,578,061 A | 11/1996 | Stroetmann et al. |
| 5,584,803 A | 12/1996 | Stevens et al. |
| 5,584,804 A | 12/1996 | Klatz et al. |
| 5,584,868 A | 12/1996 | Salo et al. |
| 5,587,200 A | 12/1996 | Lorenz et al. |
| 5,589,856 A | 12/1996 | Stein et al. |
| 5,601,604 A | 2/1997 | Vincent |
| 5,601,609 A | 2/1997 | Duncan |
| 5,601,611 A | 2/1997 | Fayram et al. |
| 5,616,268 A | 4/1997 | Carr |
| 5,620,468 A | 4/1997 | Mongeon et al. |
| 5,622,687 A | 4/1997 | Krishnan et al. |
| 5,626,622 A | 5/1997 | Cooper |
| 5,632,267 A | 5/1997 | Hoegnelid et al. |
| 5,634,895 A | 6/1997 | Igo et al. |
| 5,634,899 A | 6/1997 | Shapland et al. |
| 5,649,966 A | 7/1997 | Noren et al. |
| 5,651,378 A | 7/1997 | Matheny et al. |
| 5,654,030 A | 8/1997 | Munshi et al. |
| 5,662,687 A | 9/1997 | Hedberg et al. |
| 5,670,755 A | 9/1997 | Kwon |
| 5,674,251 A | 10/1997 | Combs et al. |
| 5,674,259 A | 10/1997 | Gray |
| 5,683,429 A | 11/1997 | Mehra |
| 5,683,431 A | 11/1997 | Wang |
| 5,687,734 A | 11/1997 | Dempsey et al. |
| 5,690,691 A | 11/1997 | Chen et al. |
| 5,694,945 A | 12/1997 | Ben-Haim |
| 5,697,953 A | 12/1997 | Kroll et al. |
| 5,704,368 A | 1/1998 | Asano et al. |
| 5,713,924 A | 2/1998 | Min et al. |
| 5,713,929 A | 2/1998 | Hess et al. |
| 5,713,935 A | 2/1998 | Prutchi et al. |
| 5,716,385 A | 2/1998 | Mittal et al. |
| 5,720,768 A | 2/1998 | Verboven-Nelissen |
| 5,727,558 A | 3/1998 | Hakki et al. |
| 5,735,876 A | 4/1998 | Kroll et al. |
| 5,738,096 A | 4/1998 | Ben-Haim |
| 5,738,105 A | 4/1998 | Kroll |
| 5,741,211 A | 4/1998 | Renirie et al. |

(56) References Cited

U.S. PATENT DOCUMENTS

| | | |
|---|---|---|
| 5,741,791 A | 4/1998 | Olsen |
| 5,749,906 A | 5/1998 | Kieval et al. |
| 5,755,740 A | 5/1998 | Nappholz |
| 5,777,607 A | 7/1998 | Koolen |
| 5,779,661 A | 7/1998 | Stephen et al. |
| 5,782,876 A | 7/1998 | Flammang |
| 5,782,881 A | 7/1998 | Lu et al. |
| 5,783,951 A | 7/1998 | Inoue et al. |
| 5,790,106 A | 8/1998 | Hirano et al. |
| 5,790,107 A | 8/1998 | Kasser et al. |
| 5,792,189 A | 8/1998 | Gray et al. |
| 5,792,198 A | 8/1998 | Nappholz |
| 5,792,208 A | 8/1998 | Gray |
| 5,792,210 A | 8/1998 | Wamubu et al. |
| 5,795,304 A | 8/1998 | Sun et al. |
| 5,797,967 A | 8/1998 | KenKnight |
| 5,800,464 A | 9/1998 | Kieval |
| 5,807,234 A | 9/1998 | Bui et al. |
| 5,807,306 A | 9/1998 | Shapland et al. |
| 5,814,079 A | 9/1998 | Kieval |
| 5,824,016 A | 10/1998 | Ekwall |
| 5,825,352 A | 10/1998 | Bisset et al. |
| 5,836,994 A | 11/1998 | Bourgeois |
| 5,837,006 A | 11/1998 | Ocel et al. |
| 5,841,078 A | 11/1998 | Miller et al. |
| 5,854,881 A | 12/1998 | Yoshida et al. |
| 5,861,014 A | 1/1999 | Familoni |
| 5,865,787 A | 2/1999 | Shapland et al. |
| 5,868,141 A | 2/1999 | Ellias |
| 5,871,506 A | 2/1999 | Mower |
| 5,891,185 A | 4/1999 | Freed |
| 5,906,607 A | 5/1999 | Taylor et al. |
| 5,911,223 A | 6/1999 | Weaver et al. |
| 5,913,876 A | 6/1999 | Taylor et al. |
| 5,914,465 A | 6/1999 | Allen et al. |
| 5,919,216 A | 7/1999 | Houben et al. |
| 5,920,309 A | 7/1999 | Bisset et al. |
| 5,925,070 A | 7/1999 | King et al. |
| 5,927,284 A | 7/1999 | Borst et al. |
| 5,938,669 A | 8/1999 | Klaiber et al. |
| 5,954,761 A | 9/1999 | Machek et al. |
| 5,956,020 A | 9/1999 | D'Amico et al. |
| 5,961,871 A | 10/1999 | Bible et al. |
| 5,962,246 A | 10/1999 | Ladner et al. |
| 5,979,449 A | 11/1999 | Steer |
| 5,991,649 A | 11/1999 | Garfield et al. |
| 5,995,872 A | 11/1999 | Bourgeois |
| 6,002,594 A | 12/1999 | Ledin et al. |
| 6,006,134 A | 12/1999 | Hill et al. |
| 6,023,640 A | 2/2000 | Ross |
| 6,026,326 A | 2/2000 | Bardy |
| 6,026,626 A | 2/2000 | Fisher |
| 6,032,074 A | 2/2000 | Collins |
| 6,032,672 A | 3/2000 | Taylor |
| 6,037,882 A | 3/2000 | Levy |
| 6,041,252 A | 3/2000 | Walker et al. |
| 6,041,258 A | 3/2000 | Cigaina et al. |
| 6,057,374 A | 5/2000 | Huntington et al. |
| 6,066,163 A | 5/2000 | John |
| 6,067,470 A | 5/2000 | Mower |
| 6,067,991 A | 5/2000 | Forsell |
| 6,071,305 A | 6/2000 | Brown et al. |
| 6,075,520 A | 6/2000 | Inoue et al. |
| 6,083,249 A | 7/2000 | Familoni |
| 6,086,582 A | 7/2000 | Altman et al. |
| 6,091,992 A | 7/2000 | Bourgeois |
| 6,092,528 A | 7/2000 | Edwards |
| 6,093,167 A | 7/2000 | Houben et al. |
| 6,096,361 A | 8/2000 | Yamane et al. |
| 6,104,955 A | 8/2000 | Bourgeois |
| 6,115,635 A | 9/2000 | Bourgeois |
| 6,122,536 A | 9/2000 | Sun et al. |
| 6,128,007 A | 10/2000 | Seybold et al. |
| 6,129,685 A | 10/2000 | Howard |
| 6,132,372 A | 10/2000 | Essen-Moller |
| 6,133,906 A | 10/2000 | Geaghan |
| 6,135,978 A | 10/2000 | Houben et al. |
| 6,135,987 A | 10/2000 | Tsai et al. |
| 6,136,019 A | 10/2000 | Mower |
| 6,141,586 A | 10/2000 | Mower |
| 6,141,587 A | 10/2000 | Mower |
| 6,151,586 A | 11/2000 | Brown |
| 6,178,351 B1 | 1/2001 | Mower |
| 6,185,452 B1 | 2/2001 | Schulman et al. |
| 6,216,039 B1 | 4/2001 | Bourgeois |
| 6,216,045 B1 | 4/2001 | Black et al. |
| 6,233,484 B1 | 5/2001 | Ben-Haim et al. |
| 6,233,487 B1 | 5/2001 | Mika et al. |
| 6,236,887 B1 | 5/2001 | Ben-Haim et al. |
| 6,239,389 B1 | 5/2001 | Allen et al. |
| 6,243,607 B1 | 6/2001 | Mintchev et al. |
| 6,249,697 B1 | 6/2001 | Asano et al. |
| 6,261,280 B1 | 7/2001 | Houben et al. |
| 6,278,443 B1 | 8/2001 | Amro et al. |
| 6,285,906 B1 | 9/2001 | Ben-Haim et al. |
| 6,292,693 B1 | 9/2001 | Darvish et al. |
| 6,292,704 B1 | 9/2001 | Malonek et al. |
| 6,295,470 B1 | 9/2001 | Mower |
| 6,296,693 B1 | 10/2001 | McCarthy |
| 6,298,254 B2 | 10/2001 | Tamada |
| 6,298,268 B1 | 10/2001 | Ben-Haim et al. |
| 6,317,631 B1 | 11/2001 | Ben-Haim et al. |
| 6,330,476 B1 | 12/2001 | Ben-Haim |
| 6,334,073 B1 | 12/2001 | Levine |
| 6,337,995 B1 | 1/2002 | Mower |
| 6,341,235 B1 | 1/2002 | Mower |
| 6,343,232 B1 | 1/2002 | Mower |
| 6,363,279 B1 | 3/2002 | Ben-Haim et al. |
| 6,363,937 B1 | 4/2002 | Hovda |
| 6,381,495 B1 | 4/2002 | Jenkins |
| 6,392,636 B1 | 5/2002 | Ferrari et al. |
| 6,405,732 B1 | 6/2002 | Edwards |
| 6,411,842 B1 | 6/2002 | Cigaina et al. |
| 6,411,847 B1 | 6/2002 | Mower |
| 6,415,178 B1 | 7/2002 | Ben-Haim et al. |
| 6,417,846 B1 | 7/2002 | Lee |
| 6,424,864 B1 | 7/2002 | Matsuura |
| 6,427,089 B1 | 7/2002 | Knowlton |
| 6,433,069 B1 | 8/2002 | Oeltjen et al. |
| 6,449,511 B1 | 9/2002 | Mintchev et al. |
| 6,452,514 B1 | 9/2002 | Philipp |
| 6,453,199 B1 | 9/2002 | Kobozev |
| 6,454,699 B1 | 9/2002 | Forsell |
| 6,463,323 B1 | 10/2002 | Conrad-Vlasak |
| 6,463,324 B1 | 10/2002 | Ben-Haim et al. |
| 6,473,069 B1 | 10/2002 | Gerpheide |
| 6,476,766 B1 | 11/2002 | Cohen |
| 6,498,944 B1 | 12/2002 | Ben-Haim et al. |
| 6,504,530 B1 | 1/2003 | Wilson et al. |
| 6,505,745 B1 | 1/2003 | Anderson |
| 6,507,093 B2 | 1/2003 | Kaneda et al. |
| 6,535,764 B2 | 3/2003 | Imran |
| RE38,119 E | 5/2003 | Mower |
| 6,558,345 B1 | 5/2003 | Houben et al. |
| 6,564,101 B1 * | 5/2003 | Zikria ............................ 607/40 |
| 6,567,700 B1 | 5/2003 | Turcott et al. |
| 6,570,557 B1 | 5/2003 | Westerman et al. |
| 6,571,127 B1 | 5/2003 | Ben-Haim et al. |
| 6,572,542 B1 | 6/2003 | Houben et al. |
| 6,583,676 B2 | 6/2003 | Krah et al. |
| 6,584,348 B2 | 6/2003 | Glukhovsky |
| 6,587,093 B1 | 7/2003 | Shaw et al. |
| 6,587,721 B1 | 7/2003 | Prutchi et al. |
| 6,591,137 B1 | 7/2003 | Fischell et al. |
| 6,594,515 B2 | 7/2003 | Watson |
| 6,600,953 B2 | 7/2003 | Flesler et al. |
| 6,605,039 B2 | 8/2003 | Houben et al. |
| 6,606,523 B1 | 8/2003 | Jenkins |
| 6,609,025 B2 | 8/2003 | Barrett et al. |
| 6,611,258 B1 | 8/2003 | Tanaka et al. |
| 6,612,983 B1 | 9/2003 | Marchal |
| 6,615,084 B1 | 9/2003 | Cigaina |
| 6,630,123 B1 | 10/2003 | Woltering et al. |
| 6,633,280 B1 | 10/2003 | Matsumoto et al. |

(56) References Cited

U.S. PATENT DOCUMENTS

| | | | |
|---|---|---|---|
| 6,634,895 B2 | 10/2003 | Agro |
| 6,652,444 B1 | 11/2003 | Ross |
| 6,658,297 B2 | 12/2003 | Loeb |
| 6,667,740 B2 | 12/2003 | Ely et al. |
| 6,684,104 B2 | 1/2004 | Gordon et al. |
| 6,690,156 B1 | 2/2004 | Weiner et al. |
| 6,690,963 B2 | 2/2004 | Ben-Haim et al. |
| 6,735,477 B2 | 5/2004 | Levine |
| 6,745,079 B2 | 6/2004 | King |
| 6,754,536 B2 | 6/2004 | Swoyer |
| 6,762,752 B2 | 7/2004 | Perski et al. |
| 6,781,577 B2 | 8/2004 | Shigetaka |
| 6,810,286 B2 | 10/2004 | Donovan et al. |
| 6,826,428 B1 | 11/2004 | Chen |
| 6,832,114 B1 | 12/2004 | Whitehurst et al. |
| 6,852,110 B2 | 2/2005 | Roy et al. |
| 6,853,862 B1 | 2/2005 | Marchal et al. |
| 6,869,431 B2 | 3/2005 | Maguire |
| 6,876,885 B2 | 4/2005 | Swoyer |
| 6,895,279 B2 | 5/2005 | Loeb et al. |
| 6,918,906 B2 | 7/2005 | Long |
| 6,919,205 B2 | 7/2005 | Brighton |
| 6,939,349 B2 | 9/2005 | Fleischman |
| 6,947,792 B2 | 9/2005 | Ben-Haim et al. |
| 6,949,081 B1 | 9/2005 | Chance |
| 6,952,613 B2 | 10/2005 | Swoyer et al. |
| 6,993,391 B2 | 1/2006 | Flesler et al. |
| 7,006,871 B1 | 2/2006 | Darvish et al. |
| 7,027,863 B1 | 4/2006 | Prutchi et al. |
| 7,043,295 B2 | 5/2006 | Starkebaum |
| 7,054,690 B2 | 5/2006 | Imran |
| 7,062,318 B2 | 6/2006 | Ben-Haim et al. |
| 7,076,305 B2 | 7/2006 | Imran et al. |
| 7,076,306 B2 | 7/2006 | Marchal et al. |
| 7,092,753 B2 | 8/2006 | Darvish et al. |
| 7,120,497 B2 | 10/2006 | Ben-Haim et al. |
| 7,167,748 B2 | 1/2007 | Ben-Haim et al. |
| 7,171,263 B2 | 1/2007 | Darvish et al. |
| 7,190,997 B1 | 3/2007 | Darvish et al. |
| 7,218,963 B2 | 5/2007 | Ben-Haim et al. |
| 7,221,978 B2 | 5/2007 | Ben-Haim et al. |
| 7,440,806 B1 | 10/2008 | Whitehurst et al. |
| 7,460,907 B1 | 12/2008 | Darvish et al. |
| 7,502,649 B2 * | 3/2009 | Ben-Haim et al. ............ 607/40 |
| 7,599,736 B2 | 10/2009 | DiLorenzo |
| 7,840,262 B2 | 11/2010 | Mika et al. |
| 7,966,071 B2 | 6/2011 | Ben-Haim et al. |
| 2001/0011543 A1 | 8/2001 | Forsell |
| 2002/0026141 A1 | 2/2002 | Houben et al. |
| 2002/0032444 A1 | 3/2002 | Mische |
| 2002/0052632 A1 | 5/2002 | Ben-Haim et al. |
| 2002/0065455 A1 | 5/2002 | Ben-Haim et al. |
| 2002/0081732 A1 | 6/2002 | Bowlin et al. |
| 2002/0103424 A1 | 8/2002 | Swoyer et al. |
| 2002/0123771 A1 | 9/2002 | Ideker et al. |
| 2002/0161414 A1 | 10/2002 | Flesler et al. |
| 2002/0162836 A1 | 11/2002 | Taino et al. |
| 2002/0165589 A1 | 11/2002 | Imran |
| 2002/0183682 A1 | 12/2002 | Darvish et al. |
| 2002/0183686 A1 | 12/2002 | Darvish et al. |
| 2003/0018367 A1 | 1/2003 | DiLorenzo |
| 2003/0028221 A1 | 2/2003 | Zhu et al. |
| 2003/0040777 A1 | 2/2003 | Shemer et al. |
| 2003/0045919 A1 | 3/2003 | Swoyer |
| 2003/0055464 A1 | 3/2003 | Darvish et al. |
| 2003/0055465 A1 | 3/2003 | Ben-Haim et al. |
| 2003/0055466 A1 | 3/2003 | Ben-Haim et al. |
| 2003/0055467 A1 | 3/2003 | Ben-Haim et al. |
| 2003/0066536 A1 | 4/2003 | Forsell |
| 2003/0100889 A1 | 5/2003 | Duverger et al. |
| 2003/0144708 A1 | 7/2003 | Starkebaum |
| 2003/0167476 A1 | 9/2003 | Conklin |
| 2003/0181958 A1 | 9/2003 | Doubak, III |
| 2003/0188899 A1 | 10/2003 | Chao et al. |
| 2003/0195600 A1 | 10/2003 | Tronnes et al. |
| 2003/0208212 A1 | 11/2003 | Cigaina |
| 2003/0208242 A1 | 11/2003 | Harel et al. |
| 2003/0211475 A1 | 11/2003 | Roberts |
| 2003/0220678 A1 | 11/2003 | Tronnes |
| 2004/0044376 A1 | 3/2004 | Flesler et al. |
| 2004/0059393 A1 | 3/2004 | Policker et al. |
| 2004/0088023 A1 | 5/2004 | Imran |
| 2004/0095333 A1 | 5/2004 | Morag et al. |
| 2004/0105040 A1 | 6/2004 | Oh et al. |
| 2004/0106954 A1 | 6/2004 | Whitehurst et al. |
| 2004/0107004 A1 | 6/2004 | Levine et al. |
| 2004/0134904 A1 | 7/2004 | Clemen |
| 2004/0138710 A1 | 7/2004 | Shemer et al. |
| 2004/0147816 A1 | 7/2004 | Policker et al. |
| 2004/0155871 A1 | 8/2004 | Perski et al. |
| 2004/0158138 A1 | 8/2004 | Kilcoyne |
| 2004/0158289 A1 | 8/2004 | Girouard et al. |
| 2004/0162469 A1 | 8/2004 | Imran |
| 2004/0162595 A1 | 8/2004 | Foley |
| 2004/0167583 A1 | 8/2004 | Knudson et al. |
| 2004/0193184 A1 | 9/2004 | Laufer |
| 2004/0193229 A1 | 9/2004 | Starkebaum et al. |
| 2004/0230273 A1 | 11/2004 | Cates et al. |
| 2004/0232140 A1 | 11/2004 | Kanzaki et al. |
| 2004/0236316 A1 | 11/2004 | Danitz |
| 2004/0243190 A1 | 12/2004 | Ben-Haim et al. |
| 2004/0243211 A1 | 12/2004 | Colliou et al. |
| 2004/0249421 A1 | 12/2004 | Harel et al. |
| 2005/0020965 A1 | 1/2005 | Rioux |
| 2005/0021101 A1 | 1/2005 | Chen et al. |
| 2005/0033375 A1 | 2/2005 | Marchal et al. |
| 2005/0033396 A1 | 2/2005 | Ospyka |
| 2005/0055038 A1 | 3/2005 | Kelleher et al. |
| 2005/0065505 A1 | 3/2005 | Ryan |
| 2005/0065553 A1 | 3/2005 | Ben Ezra et al. |
| 2005/0075654 A1 | 4/2005 | Kelleher |
| 2005/0090873 A1 | 4/2005 | Imran |
| 2005/0095227 A1 | 5/2005 | Rosenzweig et al. |
| 2005/0096514 A1 | 5/2005 | Starkebaum |
| 2005/0107829 A1 | 5/2005 | Edwards |
| 2005/0143784 A1 | 6/2005 | Imran |
| 2005/0149142 A1 | 7/2005 | Starkebaum |
| 2005/0164925 A1 | 7/2005 | Jakubowski et al. |
| 2005/0183732 A1 | 8/2005 | Edwards |
| 2005/0192542 A1 | 9/2005 | Dev et al. |
| 2005/0192615 A1 | 9/2005 | Torre et al. |
| 2005/0203500 A1 | 9/2005 | Saadat |
| 2005/0209653 A1 | 9/2005 | Herbert et al. |
| 2005/0222638 A1 | 10/2005 | Foley et al. |
| 2006/0036126 A1 | 2/2006 | Ross et al. |
| 2006/0064037 A1 | 3/2006 | Shalon |
| 2006/0074459 A1 | 4/2006 | Flesler et al. |
| 2006/0079475 A1 | 4/2006 | Zhang et al. |
| 2006/0085045 A1 | 4/2006 | Harel et al. |
| 2006/0097991 A1 | 5/2006 | Hotelling et al. |
| 2006/0142803 A1 | 6/2006 | Mintchev |
| 2006/0173238 A1 | 8/2006 | Starkebaum |
| 2006/0184207 A1 | 8/2006 | Darvish et al. |
| 2006/0247718 A1 | 11/2006 | Starkebaum |
| 2006/0264699 A1 | 11/2006 | Gertner |
| 2007/0016262 A1 | 1/2007 | Gross et al. |
| 2007/0027487 A1 | 2/2007 | Mika et al. |
| 2007/0027490 A1 | 2/2007 | Ben-Haim et al. |
| 2007/0027493 A1 | 2/2007 | Ben-Haim et al. |
| 2007/0060812 A1 | 3/2007 | Harel et al. |
| 2007/0060971 A1 | 3/2007 | Glasberg et al. |
| 2007/0088393 A1 | 4/2007 | Ben-Haim et al. |
| 2007/0156177 A1 | 7/2007 | Harel et al. |
| 2007/0161851 A1 | 7/2007 | Takizawa et al. |
| 2007/0162079 A1 | 7/2007 | Shemer et al. |
| 2007/0171211 A1 | 7/2007 | Perski et al. |
| 2007/0179556 A1 | 8/2007 | Ben Haim et al. |
| 2007/0185540 A1 | 8/2007 | Ben-Haim et al. |
| 2007/0239216 A9 | 10/2007 | Shemer et al. |
| 2007/0293901 A1 | 12/2007 | Rousso et al. |
| 2008/0046062 A1 | 2/2008 | Camps et al. |
| 2008/0051849 A1 | 2/2008 | Ben-Haim et al. |
| 2008/0058879 A1 | 3/2008 | Ben-Haim et al. |
| 2008/0058889 A1 | 3/2008 | Ben-Haim et al. |

(56) References Cited

U.S. PATENT DOCUMENTS

| | | |
|---|---|---|
| 2008/0058891 A1 | 3/2008 | Ben-Haim et al. |
| 2008/0065159 A1 | 3/2008 | Ben-Haim et al. |
| 2008/0065163 A1 | 3/2008 | Ben-Haim et al. |
| 2008/0065164 A1 | 3/2008 | Ben-Haim et al. |
| 2008/0065168 A1 | 3/2008 | Bitton et al. |
| 2008/0077174 A1 | 3/2008 | Mische |
| 2008/0140142 A1 | 6/2008 | Darvish et al. |
| 2008/0188837 A1 | 8/2008 | Belsky et al. |
| 2009/0062893 A1 | 3/2009 | Spehr et al. |
| 2009/0088816 A1 | 4/2009 | Harel |
| 2009/0131993 A1 | 5/2009 | Rousso et al. |
| 2009/0204063 A1 | 8/2009 | Policker |
| 2009/0209985 A1* | 8/2009 | Khalili .......................... 606/157 |
| 2009/0281449 A1 | 11/2009 | Thrower et al. |
| 2009/0292324 A1 | 11/2009 | Rousso et al. |
| 2010/0016923 A1 | 1/2010 | Rousso et al. |
| 2010/0228313 A1 | 9/2010 | Starkebaum et al. |

FOREIGN PATENT DOCUMENTS

| | | |
|---|---|---|
| EP | 0148687 | 7/1985 |
| EP | 0156593 | 10/1985 |
| EP | 0250931 | 1/1988 |
| EP | 0268379 | 5/1988 |
| EP | 0314078 | 5/1989 |
| EP | 0421780 | 4/1991 |
| EP | 0481684 | 4/1992 |
| EP | 0503839 | 9/1992 |
| EP | 0528751 | 2/1993 |
| EP | 0220916 | 4/1994 |
| EP | 0727241 | 8/1996 |
| EP | 0996482 | 5/2000 |
| EP | 1036545 | 9/2000 |
| EP | 1263498 | 12/2002 |
| EP | 1 447 052 | 8/2004 |
| EP | 1447632 | 8/2004 |
| EP | 0910429 | 3/2005 |
| EP | 1515102 | 3/2005 |
| GB | 1394171 | 5/1975 |
| GB | 2033587 | 5/1980 |
| GB | 2280377 | 2/1995 |
| JP | 62-112530 | 5/1987 |
| JP | 62-275471 | 11/1987 |
| JP | 04-117967 | 4/1992 |
| JP | 04-282168 | 10/1992 |
| JP | 04-365493 | 12/1992 |
| JP | 06-169998 | 6/1994 |
| JP | 06-193884 | 7/1994 |
| JP | 06-506619 | 7/1994 |
| JP | 06-310268 | 11/1994 |
| JP | 07-503865 | 4/1995 |
| JP | 07-126600 | 5/1995 |
| JP | 07-144024 | 6/1995 |
| JP | 07-508662 | 9/1995 |
| JP | 08-064359 | 3/1996 |
| JP | 08-243176 | 9/1996 |
| JP | 09-229372 | 9/1997 |
| JP | 2001-086967 | 4/2001 |
| JP | 2003319945 | 11/2003 |
| RU | 386634 | 6/1973 |
| RU | 553977 | 5/1977 |
| RU | 0553977 | 5/1977 |
| RU | 0709078 | 1/1980 |
| RU | 0831131 | 5/1981 |
| RU | 831131 | 5/1981 |
| RU | 1039506 | 9/1983 |
| RU | 1147408 | 3/1985 |
| RU | 2014844 | 6/1994 |
| RU | 1827793 | 5/1995 |
| RU | 2055606 | 3/1996 |
| RU | 2075980 | 3/1997 |
| RU | 2077273 | 4/1997 |
| RU | 2078547 | 5/1997 |
| RU | 2260451 | 10/2001 |
| WO | WO 91/19534 | 12/1991 |
| WO | WO 92/00716 | 1/1992 |
| WO | WO 92/13592 | 8/1992 |
| WO | WO 93/02743 | 2/1993 |
| WO | WO 93/02745 | 2/1993 |
| WO | WO 93/08874 | 5/1993 |
| WO | WO 93/18820 | 9/1993 |
| WO | WO 94/01172 | 1/1994 |
| WO | WO 94/17855 | 8/1994 |
| WO | WO 95/02995 | 2/1995 |
| WO | WO 95/08316 | 3/1995 |
| WO | WO 96/05768 | 2/1996 |
| WO | WO 96/10358 | 4/1996 |
| WO | WO 96/16696 | 6/1996 |
| WO | WO 97/15227 | 1/1997 |
| WO | WO 97/06849 | 2/1997 |
| WO | WO 97/24981 | 7/1997 |
| WO | WO 97/24983 | 7/1997 |
| WO | WO 97/25098 | 7/1997 |
| WO | WO 97/25101 | 7/1997 |
| WO | WO 97/26042 | 7/1997 |
| WO | WO 97/27900 | 7/1997 |
| WO | WO 97/29679 | 8/1997 |
| WO | WO 97/29682 | 8/1997 |
| WO | WO 97/29684 | 8/1997 |
| WO | WO 97/29700 | 8/1997 |
| WO | WO 97/29701 | 8/1997 |
| WO | WO 97/29709 | 8/1997 |
| WO | 97/41921 | 11/1997 |
| WO | WO 98/10828 | 3/1998 |
| WO | WO 98/10829 | 3/1998 |
| WO | WO 98/10830 | 3/1998 |
| WO | WO 98/10831 | 3/1998 |
| WO | WO 98/10832 | 3/1998 |
| WO | WO 98/11840 | 3/1998 |
| WO | WO 98/15317 | 4/1998 |
| WO | WO 98/19719 | 5/1998 |
| WO | WO 98/56378 | 12/1998 |
| WO | WO 98/57701 | 12/1998 |
| WO | WO 99/03533 | 1/1999 |
| WO | WO 99/06105 | 2/1999 |
| WO | WO 99/09971 | 3/1999 |
| WO | WO 99/55360 | 4/1999 |
| WO | WO 99/24110 | 5/1999 |
| WO | WO 99/29307 | 6/1999 |
| WO | WO 99/59548 | 11/1999 |
| WO | WO 00/01443 | 1/2000 |
| WO | WO 00/04947 | 2/2000 |
| WO | WO 00/16741 | 3/2000 |
| WO | WO 00/27475 | 5/2000 |
| WO | WO 00/42914 | 7/2000 |
| WO | WO 00/12525 | 9/2000 |
| WO | WO 00/53257 | 9/2000 |
| WO | WO 00/61223 | 10/2000 |
| WO | WO 00/74773 | 12/2000 |
| WO | WO 01/24871 | 4/2001 |
| WO | 01/41671 | 6/2001 |
| WO | WO 01/49367 | 7/2001 |
| WO | WO 01/52931 | 7/2001 |
| WO | WO 01/66183 | 9/2001 |
| WO | 01/83019 | 11/2001 |
| WO | WO 01/91854 | 12/2001 |
| WO | WO 01/93950 | 12/2001 |
| WO | WO 01/93951 | 12/2001 |
| WO | WO 02/10791 | 2/2002 |
| WO | WO 02/23953 | 3/2002 |
| WO | WO 02/053093 | 7/2002 |
| WO | 02/082968 | 10/2002 |
| WO | WO 02/082968 | 10/2002 |
| WO | 02/089655 | 11/2002 |
| WO | 03/020365 | 3/2003 |
| WO | WO 03/045493 | 5/2003 |
| WO | WO 2004/021858 | 3/2004 |
| WO | 2004/043280 | 5/2004 |
| WO | WO 2004/059393 | 7/2004 |
| WO | 2004/066903 | 8/2004 |
| WO | 2004/069330 | 8/2004 |
| WO | WO 2004/070396 | 8/2004 |
| WO | WO 2004/080533 | 9/2004 |

(56) References Cited

FOREIGN PATENT DOCUMENTS

| WO | 2004/091361 | 10/2004 |
|---|---|---|
| WO | 2004/096337 | 11/2004 |
| WO | WO 2004/112563 | 12/2004 |
| WO | WO 2004/112883 | 12/2004 |
| WO | 2005/007237 | 1/2005 |
| WO | WO 2005/007232 | 1/2005 |
| WO | 2005/009288 | 2/2005 |
| WO | 2005/016181 | 2/2005 |
| WO | WO 2005/023081 | 3/2005 |
| WO | 2005/037152 | 4/2005 |
| WO | 2005/041749 | 5/2005 |
| WO | WO 2005/087310 | 9/2005 |
| WO | WO 2005/106333 | 11/2005 |
| WO | WO 2005/114369 | 12/2005 |
| WO | WO 2006/018851 | 2/2006 |
| WO | 2006/035446 | 4/2006 |
| WO | 2006/045075 | 4/2006 |
| WO | WO 2006/073671 | 7/2006 |
| WO | WO 2006/087712 | 8/2006 |
| WO | WO 2006/087717 | 8/2006 |
| WO | WO 2006/097934 | 9/2006 |
| WO | WO 2006/097935 | 9/2006 |
| WO | WO 2006/102626 | 9/2006 |
| WO | WO 2006/119467 | 9/2006 |
| WO | 2006/118790 | 11/2006 |
| WO | WO 2006/119467 | 11/2006 |
| WO | 2006/129321 | 12/2006 |
| WO | 2007/080595 | 7/2007 |
| WO | WO 2007/091255 | 8/2007 |
| WO | WO 2007/096877 | 8/2007 |
| WO | WO 2007/096878 | 8/2007 |
| WO | WO 2008/007368 | 1/2008 |
| WO | 2008/117296 | 10/2008 |
| WO | 2008/139463 | 11/2008 |
| ZA | 97/06341 | 2/1998 |

OTHER PUBLICATIONS

Applicant-Initiated Interview Summary Dated Feb. 18, 2014 From the US Patent and Trademark Office Re. U.S. Appl. No. 10/570,576.
Communication Pursuant to Article 94(3) EPC Dated Jun. 18, 2013 From the European Patent Office Re.: Application No. 04745004.4.
Official Action Dated Jun. 14, 2013 From the US Patent and Trademark Office Re. U.S. Appl. No. 10/526,708.
Official Action Dated Jul. 2, 2013 From the US Patent and Trademark Office Re.: U.S. Appl. No. 10/570,576.
Ajumobi AB et al., "Diabetic Gastroparesis: Evaluation and Management," Hospital Physician, Mar. 2008, pp. 27-35.
Bohdjalian A et al., "Improvement in glycemic control in morbidly obese type 2 diabetic subjects by gastric stimulation," Obes Surg 19(9):1221-7 (Sep. 2009) (Epub Jul. 3, 2009).
Bohdjalian A et al., "One-year experience with Tantalus: a new surgical approach to treat morbid obesity," Obes Surg. 16(5):627-34 (May 2006).
Favretti F et al., "Treatment of morbid obesity with the Transcend® Implantable Gastric Stimulator (IGS®): A prospective survey," Obesity Surgery, 14, 666-670 (2004). Abstract.
Ghigo E et al., "Ghrelin: more than a natural GH secretagogue and/or an orexigenic factor," Clinical Endocrinology 62(1):1-17 (Jan. 2005; published online Nov. 17, 2004).
Lin Z et al., "Treatment of diabetic gastroparesis by high-frequency gastric electrical stimulation," Diabetes Care 27:1071-1076 (2004).
Sanmiguel CP et al., "Gastric Electrical Stimulation with the TANTALUS® System in Obese Type 2 Diabetes Patients: Effect on Weight and Glycemic Control," J Diabetes Sci Technol 3(4):964-970 (Jul. 2009).
van der Voort et al., "Gastric electrical stimulation results in improved metabolic control is diabetic patients suffering from gastroparesis," Exp Clin Endocrinol Diabetes 113:38-42 (2005).
An International Search Report and a Written Opinion both dated Sep. 2, 2011, which issued during the prosecution of Applicant's PCT/IL2011/000116.
An Office Action dated Sep. 27, 2011, which issued during the prosecution of U.S. Appl. No. 10/599,015.
An Office Action dated Jul. 28, 2008, which issued during the prosecution of the U.S. Appl. No. 11/336,099.
An Office Action dated Nov. 4, 2008, which issued during the prosecution of U.S. Appl. No. 11/336,099.
An Office Action dated Aug. 6, 2009, which issued during the prosecution of U.S. Appl. No. 11/336,099.
An Office Action dated Nov. 15, 2010, which issued during the prosecution of U.S. Appl. No. 11/336,099.
An Office Action dated May 20, 2011, which issued during the prosecution of U.S. Appl. No. 11/336,099.
An Office Action dated Nov. 30, 2011, which issued during the prosecution of U.S. Appl. No. 11/336,099.
Lamb F.S. et al., "Cyclosporine augments reactivity of isolated blood vessels", Life Sciences, 40, pp. 2571-2578, 1987. Abstract.
Johansson B. et al., "Static and dynamic components in the vascular myogenic response to passive changes in length as revealed by electrical and mechanical recordings from the rat portal vein", Circulation Research, 36, pp. 76-83, 1975.
Zelcer E. et al., "Spontaneous electrical activity in pressurized small mesenteric arteries", Blood Vessels, 19, pp. 301-310, 1982.
Schobel H.P. et al., "Preeclampsia—a state of sympathetic overactivity", New England Journal of Medicine, 335, pp. 148-1485, 1996.
Rosenpire A.J. et al., "Pulsed DC Electric Fields Couple to Natural NAD(P)H Oscillations in HT-1080 Fibrosarcoma Cells", Journal of Cell Science, 114(Pt. 8), pp. 1515-1520, Apr. 2001.
M D Robertson, et al, "The influence of the colon on postprandial glucagons-like peptide 1 (7-36) amide concentration in man", Journal of Endocrinology (1999) 161, 25-31.
T Vilsboll and Associates, Research design and methods, Diabetes, vol. 50, Mar. 2001, pp. 610-613.
Daniel J. Drucker, "Development of glucagon-like peptide-1-based pharmaceuticals as therapeutic agents for the treatment of diabetes", Current Pharmaceutical Design, 2001, 7, 1399-1412, Abstract.
Shemerovskii KA, "Effect of feeding on the activity of duodenal smooth muscle in dogs", Biull Eksp Biol Med. Oct. 1978;86(10):394-7. (Abstract only).
Official Action Dated Nov. 14, 2013 From the US Patent and Trademark Office Re. U.S. Appl. No. 11/884,389.
Notice of Allowance Dated Nov. 25, 2013 From the US Patent and Trademark Office Re. U.S. Appl. No. 10/526,708.
Official Action Dated Nov. 27, 2013 From the US Patent and Trademark Office Re. U.S. Appl. No. 10/570,576.
Babsky et al. Translation of Physiology of Man, Moscow Medicine, p. 115, 348-351, 376, Extracts, 1972.
Communication Pursuant to Article 94(3) EPC Dated Oct. 1, 2013 From the European Patent Office Re. Application No. 07110023.4.
Official Action Dated Sep. 12, 2013 From the US Patent and Trademark Office Re. U.S. Appl. No. 10/804,560.
Communication Pursuant to Article 94(3) EPC Dated Jul. 3, 2014 From the European Patent Office Re. Application No. 07110023.4.
Communication to Pursuant to Article 94(3) EPC Dated Jun. 6, 2014 From the European Search Report Re.: Application No. 04770468.9.
Official Action Dated Jun. 4, 2014 From the US Patent and Trademark Office Re. U.S. Appl. No. 10/804,560.
International Search Report and the Written Opinion Dated Oct. 28, 2008 From the International Searching Authority Re. Application No. PCT/IL2008/000646.
Request for Ex Parte Reexamination of US Patent No. 6,236,887—IDS Submitted Sep. 29, 2008 From the US Patent and Trademark Office Re.: U.S. Appl. No. 90/008,707.
Antoni et al. "Polarization Effects of Sinusoidal 50-Cycle Alternating Current on Membrane Potential of Mammalian Cardiac Fibres", Pflueger's Archiv European Journal of Physiology, 314(4): 274-291, 1970. Abstract.
Lin et al. "Effects of Pacing Parameters on Entrainment of Gastric Slow Waves in Patients With Gastroparesis", The American Journal of Physiology, 274(1/Pt 1): G186-G191, Jan. 1998.
Sanmiguel et al. "The TANTALUS® System for Obesity: Effect on Gastric Emptying of Solids and Ghrelin Plasma Levels", Obesity Surgery, 17: 1503-1509, 2007.

(56) References Cited

OTHER PUBLICATIONS

Soffer et al. "Review Article: Gastric Electrical Stimulation for Gastroparesis—Physiological Foundations, Technical Aspects and Clinical Implications", Alimentary Pharmacology & Therapeutics, 30: 681-694, 2009.
Yamada et al. "[Effects of Drug on Electromechanical Activities of the Stomach and Duodenum of Conscious Dogs]", Nihon Heikatsukin Gakkai Zasshi, 19(1): 25-35, Feb. 1983. [Article in Japanese]. Abstract.
Yang et al. "Effect of Two-Channel Gastric Electrical Stimulation With Trains of Pulses on Gastric Motility", World Journal of Gatroenterology, 15(19): 2406-2411, May 2009.
U.S. Appl. No. 90/008,688, filed Jun. 15, 2007, Ben Haim.
U.S. Appl. No. 90/008,689, Ben Haim.
U.S. Appl. No. 90/008,707, filed Jun. 7, 2007, Ben Haim.
U.S. Appl. No. 95/00,032, Ben Haim.
Advisory Action Before the Filing of an Appeal Brief Dated Mar. 22, 2012 From the US Patent and Trademark Office Re. U.S. Appl. No. 11/886,154.
Amended Request for Ex Parte Reexamination of US Patent No. 6,317,631 Dated Aug. 20, 2007 From the US Patent and Trademark Office Re.: U.S. Appl. No. 90/008,689.
Communication Pursuant to Article 94(3) EPC Dated Mar. 2, 2009 From the European Patent Office Re.: Application No. 05853465.2.
Communication Pursuant to Article 94(3) EPC Dated Oct. 10, 2011 From the European Patent Office Re. Application No. 07110023.4.
Communication Pursuant to Article 94(3) EPC Dated Aug. 11, 2010 From the European Patent Office Re. Application No. 99931435.4.
Communication Pursuant to Article 94(3) EPC Dated Aug. 26, 2011 From the European Patent Office Re. Application No. 06759102.4.
Communication Pursuant to Article 94(3) EPC Dated Aug. 26, 2011 From the European Patent Office Re.: Application No. 05853465.2.
Communication Pursuant to Article 94(3) EPC Dated Jan. 27, 2010 From the European Patent Office Re. Application No. 07110023.4.
Communication Pursuant to Article 94(3) EPC Dated Jan. 28, 2009 From the European Patent Office Re.: Application No. 03794043.4.
Communication Pursuant to Article 94(3) EPC Dated Jan. 29, 2009 From the European Patent Office Re.: Application No. 04106247.2.
Communication Pursuant to Article 94(3) EPC Dated Aug. 30, 2012 From the European Patent Office Re. Application No. 07110023.4.
Communication Pursuant to Article 96(2) EPC Dated Mar. 2, 2007 From the European Patent Office Re.: Application No. 97929478.2.
Communication Pursuant to Rules 70(2) and 70a(2) EPC Dated Oct. 12, 2012 From the European Patent Office Re.: Application No. 06711186.4.
Communication to Pursuant to Article 94(3) EPC Dated Mar. 4, 2009 From the European Search Report Re.: Application No. 06759102.4.
Corrected Notice of Allowability Dated Jul. 13, 2012 From the US Patent and Trademark Office Re. U.S. Appl. No. 11/933,168.
Corrected Notice of Allowability Dated Aug. 17, 2012 From the US Patent and Trademark Office Re. U.S. Appl. No. 11/931,724.
European Search Report and the European Search Opinion Dated Jul. 27, 2007 From the European Patent Office Re. Application No. 07110023.4.
Examination Report Dated Mar. 13, 2012 From the Government of India, Patent Office, Intellectual Property Building Re. Application No. 2988/CHENP/2007.
Examination Report Dated May 18, 2011 From the Government of India, Patent Office, Intellectual Property Building Re. Application No. 2988/CHENP/2007.
Examination Report Dated Jun. 26, 2009 From the Government of India, Patent Office Re.: Application No. 1161/CHENP/2006.
Examination Report Dated Nov. 30, 2010 From the Government of India, Patent Office Re. Application No. 212/MUMNP/2006.
Inter Partes Reexamination Communication of Patent US 6,330,476 Dated Sep. 4, 2007 From the US Patent and Trademark Office Re.: U.S. Appl. No. 95/000,032.
International Preliminary Report on Patentability Dated Dec. 1, 2004 From the International Preliminary Examining Authority Re.: Application No. PCT/IL03/00736.
International Preliminary Report on Patentability Dated Nov. 15, 2007 From the International Bureau of WIPO Re.: Application No. PCT/US2006/017281.
International Preliminary Report on Patentability Dated Jun. 21, 2007 From the International Bureau of WIPO Re.: Application No. Jun. 21, 2007.
International Preliminary Report on Patentability Dated Sep. 27, 2007 From the International Bureau of WIPO Re.: Application No. PCT/IL2006/000345.
International Preliminary Report on Patentability Dated Aug. 30, 2007 From the International Bureau of WIPO Re.: Application No. PCT/IL2006/000204.
International Search Report and the Written Opinion Dated May 12, 2006 From the International Searching Authority Re.: Application No. PCT/US05/44557.
International Search Report and the Written Opinion Dated Oct. 16, 2006 From the International Searching Authority Re.: Application No. PCT/US06/17281.
International Search Report and the Written Opinion Dated Sep. 29, 2006 From the International Searching Authority Re.: Application No. PCT/IL06/00204.
International Search Report Dated Sep. 13, 2004 From the International Searching Authority Re.: Application No. PCT/IL03/00736.
Invitation Pursuant to Rule 62a(1) EPC and Rule 63(1) EPC Dated May 5, 2010 From the European Patent Office Re.: Application No. 04719312.3.
Notice of Allowability Dated Jul. 13, 2012 From the US Patent and Trademark Office Re. U.S. Appl. No. 11/933,168.
Notice of Allowance Dated Sep. 7, 2006 From the US Patent and Trademark Office Re.: U.S. Appl. No. 10/804,560.
Notice of Allowance Dated Jul. 11, 2012 From the US Patent and Trademark Office Re. U.S. Appl. No. 11/550,560.
Notice of Allowance Dated May 11, 2011 From the US Patent and Trademark Office Re.: U.S. Appl. No. 10/237,263.
Notice of Allowance Dated Jan. 14, 2011 From the US Patent and Trademark Office Re.: U.S. Appl. No. 11/550,560.
Notice of Allowance Dated May 15, 2012 From the US Patent and Trademark Office Re.: U.S. Appl. No. 11/932,149.
Notice of Allowance Dated Jul. 16, 2012 From the US Patent and Trademark Office Re. U.S. Appl. No. 11/931,889.
Notice of Allowance Dated May 16, 2012 From the US Patent and Trademark Office Re. U.S. Appl. No. 11/886,154.
Notice of Allowance Dated Jul. 18, 2012 From the US Patent and Trademark Office Re.: U.S. Appl. No. 11/931,724.
Notice of Allowance Dated Jun. 20, 2012 From the US Patent and Trademark Office Re. U.S. Appl. No. 11/933,168.
Notice of Allowance Dated Jun. 27, 2012 From the US Patent and Trademark Office Re.: U.S. Appl. No. 11/932,064.
Notice of Allowance Dated May 27, 2010 From the US Patent and Trademark Office Re.: U.S. Appl. No. 10/549,216.
Notice of Allowance Dated Dec. 28, 2010 From the US Patent and Trademark Office Re.: U.S. Appl. No. 11/932,064.
Notice of Allowance Dated Nov. 29, 2010 From the US Patent and Trademark Office Re.: U.S. Appl. No. 10/237,263.
Notice of Allowance Dated Aug. 31, 2012 From the US Patent and Trademark Office Re. U.S. Appl. No. 11/318,845.
Notice of Allowance Dated Aug. 31, 2012 From the US Patent and Trademark Office Re. U.S. Appl. No. 12/910,943.
Notice of Non-Compliant Amendment Dated Jun. 1, 2011 From the US Patent and Trademark Office Re. U.S. Appl. No. 11/886,154.
Notice of Non-Compliant Amendment Dated Dec. 12, 2011 From the US Patent and Trademark Office Re. U.S. Appl. No. 11/792,811.
Notice of Non-Compliant Amendment Dated Jul. 15, 2011 From the US Patent and Trademark Office Re. U.S. Appl. No. 11/886,154.
Notification of Reasons of Rejection Dated Sep. 29, 2008 From the Japanese Patent Office Re.: Application No. 2004-534013 and Its Translation Into English.
Office Action Dated Dec. 4, 2009 From the State Intellectual Property Office of the People's Republic of China Re.: Application No. 03824661.9 and Its Translation Into English.
Office Action Dated Nov. 7, 2008 From the State Intellectual Property Office of the People's Republic of China Re.: Application No. 03824661.9 and Its Translation Into English.

(56) References Cited

OTHER PUBLICATIONS

Office Action Dated Jan. 8, 2010 From the State Intellectual Property Office (SIPO) of the People's Republic of China Re.: Application No. 200480012687.5 and Its Translation Into English.
Office Action Dated May 8, 2009 From the State Intellectual Property Office of the People's Republic of China Re.: Application No. 03824661.9 and Its Translation Into English.
Office Action Dated Oct. 12, 2004 From the Israeli Patent Office Re.: Application No. 128955.
Office Action Dated Apr. 13, 2010 From the State Intellectual Property Office of the People's Republic of China Re. Application No. 200480027293.3 and Its Translation Into English.
Office Action Dated Jul. 13, 2009 From the State Intellectual Property Office of the People's Republic of China Re.: Application No. 200480027283.3 and Its Translation Into English.
Office Action Dated Dec. 15, 2008 From the State Intellectual Property Office (SIPO) of the People's Republic of China Re.: Application No. 200480012687.5 and Its Translation Into English.
Office Action Dated Jan. 18, 2012 From the State Intellectual Property Office (SIPO) of the People's Republic of China Re.: Application No. 200480012687.5 and Its Translation Into English.
Office Action Dated Nov. 25, 2010 From the State Intellectual Property Office (SIPO) of the People's Republic of China Re.: Application No. 200480012687.5 and Its Translation Into English.
Official Action Dated Aug. 1, 2007 From the US Patent and Trademark Office Re.: U.S. Appl. No. 90/008,312.
Official Action Dated Jun. 1, 2009 From the US Patent and Trademark Office Re.: U.S. Appl. No. 10/039,845.
Official Action Dated Nov. 1, 2011 From the US Patent and Trademark Office Re.: U.S. Appl. No. 10/804,560.
Official Action Dated Oct. 1, 2009 From the US Patent and Trademark Office Re.: U.S. Appl. No. 10/237,263.
Official Action Dated Dec. 2, 2009 From the US Patent and Trademark Office Re.: U.S. Appl. No. 11/932,149.
Official Action Dated Dec. 3, 2009 From the US Patent and Trademark Office Re.: U.S. Appl. No. 11/318,845.
Official Action Dated Jan. 3, 2011 From the US Patent and Trademark Office Re.: U.S. Appl. No. 11/932,149.
Official Action Dated Jul. 3, 2012 From the US Patent and Trademark Office Re. U.S. Appl. No. 12/910,943.
Official Action Dated Nov. 3, 2009 From the US Patent and Trademark Office Re.: U.S. Appl. No. 11/931,724.
Official Action Dated Sep. 3, 2009 From the US Patent and Trademark Office Re.: U.S. Appl. No. 10/804,560.
Official Action Dated Dec. 4, 2009 From the US Patent and Trademark Office Re.: U.S. Appl. No. 11/884,389.
Official Action Dated Feb. 4, 2010 From the US Patent and Trademark Office Re.: U.S. Appl. No. 10/039,845.
Official Action Dated Jan. 4, 2011 From the US Patent and Trademark Office Re.: U.S. Appl. No. 11/318,845.
Official Action Dated Jan. 4, 2012 From the US Patent and Trademark Office Re. U.S. Appl. No. 11/673,812.
Official Action Dated Dec. 5, 2008 From the US Patent and Trademark Office Re.: U.S. Appl. No. 11/550,560.
Official Action Dated Jan. 5, 2010 From the US Patent and Trademark Office Re.: U.S. Appl. No. 11/802,685.
Official Action Dated May 5, 2010 From the US Patent and Trademark Office Re.: U.S. Appl. No. 11/884,389.
Official Action Dated Nov. 5, 2009 From the US Patent and Trademark Office Re.: U.S. Appl. No. 10/549,216.
Official Action Dated Oct. 5, 2010 From the US Patent and Trademark Office Re.: U.S. Appl. No. 10/039,845.
Official Action Dated Dec. 6, 2011 From the US Patent and Trademark Office Re.: U.S. Appl. No. 11/318,845.
Official Action Dated Jan. 6, 2010 From the US Patent and Trademark Office Re. U.S. Appl. No. 11/933,168.
Official Action Dated Jan. 6, 2011 From the US Patent and Trademark Office Re.: U.S. Appl. No. 11/931,724.
Official Action Dated Jan. 6, 2012 From the US Patent and Trademark Office Re. U.S. Appl. No. 11/933,168.
Official Action Dated Mar. 6, 2009 From the US Patent and Trademark Office Re.: U.S. Appl. No. 11/931,889.
Official Action Dated Mar. 6, 2009 From the US Patent and Trademark Office Re.: U.S. Appl. No. 11/932,064.
Official Action Dated Oct. 6, 2009 From the US Patent and Trademark Office Re.: U.S. Appl. No. 11/550,560.
Official Action Dated Aug. 8, 2007 From the US Patent and Trademark Office Re.: U.S. Appl. No. 10/804,560.
Official Action Dated Dec. 8, 2008 From the US Patent and Trademark Office Re.: U.S. Appl. No. 10/804,560.
Official Action Dated Jun. 8, 2011 From the US Patent and Trademark Office Re. U.S. Appl. No. 11/566,775.
Official Action Dated Nov. 8, 2011 From the US Patent and Trademark Office Re.: U.S. Appl. No. 11/931,889.
Official Action Dated Oct. 8, 2009 From the US Patent and Trademark Office Re. U.S. Appl. No. 11/566,775.
Official Action Dated Oct. 8, 2009 From the US Patent and Trademark Office Re.: U.S. Appl. No. 10/116,201.
Official Action Dated Aug. 9, 2011 From the US Patent and Trademark Office Re.: U.S. Appl. No. 11/932,149.
Official Action Dated Dec. 9, 2010 From the US Patent and Trademark Office Re. U.S. Appl. No. 11/566,775.
Official Action Dated Jul. 9, 2007 From the US Patent and Trademark Office Re.: U.S. Appl. No. 10/237,263.
Official Action Dated Mar. 10, 2011 From the US Patent and Trademark Office Re.: U.S. Appl. No. 11/884,389.
Official Action Dated May 10, 2012 From the US Patent and Trademark Office Re. U.S. Appl. No. 10/599,015.
Official Action Dated Oct. 10, 2008 From the US Patent and Trademark Office Re. U.S. Appl. No. 09/980,748.
Official Action Dated Jun. 11, 2010 From the US Patent and Trademark Office Re.: U.S. Appl. No. 11/550,560.
Official Action Dated Jun. 11, 2010 From the US Patent and Trademark Office Re.: U.S. Appl. No. 11/932,064.
Official Action Dated May 11, 2011 From the US Patent and Trademark Office Re.: U.S. Appl. No. 10/804,560.
Official Action Dated Oct. 11, 2011 From the US Patent and Trademark Office Re.: U.S. Appl. No. 11/919,491.
Official Action Dated Sep. 11, 2008 From the US Patent and Trademark Office Re.: U.S. Appl. No. 10/237,263.
Official Action Dated Sep. 11, 2009 From the US Patent and Trademark Office Re. U.S. Appl. No. 09/980,748.
Official Action Dated Jun. 12, 2012 From the US Patent and Trademark Office Re. U.S. Appl. No. 11/573,722.
Official Action Dated May 12, 2011 From the US Patent and Trademark Office Re.: U.S. Appl. No. 10/039,845.
Official Action Dated Sep. 12, 2008 From the US Patent and Trademark Office Re.: U.S. Appl. No. 10/039,845.
Official Action Dated Jan. 13, 2011 From the US Patent and Trademark Office Re.: U.S. Appl. No. 11/931,889.
Official Action Dated May 13, 2011 From the US Patent and Trademark Office Re. U.S. Appl. No. 11/933,168.
Official Action Dated Oct. 13, 2010 From the US Patent and Trademark Office Re.: U.S. Appl. No. 10/237,263.
Official Action Dated Oct. 13, 2010 From the US Patent and Trademark Office Re.: U.S. Appl. No. 11/919,491.
Official Action Dated Sep. 13, 2007 From the US Patent and Trademark Office Re.: U.S. Appl. No. 10/237,263.
Official Action Dated Apr. 14, 2011 From the US Patent and Trademark Office Re.: U.S. Appl. No. 11/932,149.
Official Action Dated Dec. 14, 2010 From the US Patent and Trademark Office Re.: U.S. Appl. No. 11/884,389.
Official Action Dated Jul. 14, 2008 From the US Patent and Trademark Office Re.: U.S. Appl. No. 10/526,708.
Official Action Dated Sep. 14, 2009 From the US Patent and Trademark Office Re.: U.S. Appl. No. 11/931,889.
Official Action Dated Sep. 14, 2011 From the US Patent and Trademark Office Re. U.S. Appl. No. 11/886,154.
Official Action Dated Dec. 15, 2010 From the US Patent and Trademark Office Re.: U.S. Appl. No. 10/804,560.
Official Action Dated Dec. 15, 2011 From the US Patent and Trademark Office Re. U.S. Appl. No. 12/910,943.

(56) References Cited

OTHER PUBLICATIONS

Official Action Dated Feb. 15, 2012 From the US Patent and Trademark Office Re. U.S. Appl. No. 11/802,685.
Official Action Dated Jul. 15, 2008 From the US Patent and Trademark Office Re.: U.S. Appl. No. 10/116,201.
Official Action Dated Apr. 16, 2010 From the US Patent and Trademark Office Re. U.S. Appl. No. 11/566,775.
Official Action Dated Apr. 16, 2010 From the US Patent and Trademark Office Re.: U.S. Appl. No. 11/566,775.
Official Action Dated Feb. 17, 2012 From the US Patent and Trademark Office Re.: U.S. Appl. No. 11/932,149.
Official Action Dated Jun. 17, 2010 From the US Patent and Trademark Office Re.: U.S. Appl. No. 10/549,216.
Official Action Dated Apr. 18, 2007 From the US Patent and Trademark Office Re.: U.S. Appl. No. 10/804,560.
Official Action Dated Aug. 18, 2009 From the US Patent and Trademark Office Re.: U.S. Appl. No. 10/570,576.
Official Action Dated Jan. 18, 2012 From the US Patent and Trademark Office Re. U.S. Appl. No. 11/886,154.
Official Action Dated Jul. 18, 2007 From the US Patent and Trademark Office Re.: U.S. Appl. No. 10/039,845.
Official Action Dated Jul. 19, 2007 From the US Patent and Trademark Office Re.: U.S. Appl. No. 10/526,708.
Official Action Dated Jun. 19, 2008 From the US Patent and Trademark Office Re.: U.S. Appl. No. 10/237,263.
Official Action Dated Dec. 20, 2011 From the US Patent and Trademark Office Re.: U.S. Appl. No. 10/039,845.
Official Action Dated Feb. 21, 2012 From the US Patent and Trademark Office Re. U.S. Appl. No. 10/116,201.
Official Action Dated Jan. 21, 2009 From the US Patent and Trademark Office Re.: U.S. Appl. No. 10/570,576.
Official Action Dated Jul. 21, 2010 From the US Patent and Trademark Office Re.: U.S. Appl. No. 11/802,685.
Official Action Dated May 21, 2007 From the US Patent and Trademark Office Re. U.S. Appl. No. 09/980,748.
Official Action Dated May 21, 2010 From the US Patent and Trademark Office Re. U.S. Appl. No. 10/116,201.
Official Action Dated Mar. 22, 2011 From the US Patent and Trademark Office Re. U.S. Appl. No. 11/886,154.
Official Action Dated Dec. 23, 2010 From the US Patent and Trademark Office Re. U.S. Appl. No. 09/980,748.
Official Action Dated Jun. 23, 2009 From the US Patent and Trademark Office Re.: U.S. Appl. No. 10/549,216.
Official Action Dated Dec. 24, 2008 From the US Patent and Trademark Office Re.: U.S. Appl. No. 10/237,263.
Official Action Dated Feb. 24, 2009 From the US Patent and Trademark Office Re.: U.S. Appl. No. 11/318,845.
Official Action Dated Jan. 24, 2011 From the US Patent and Trademark Office Re.: U.S. Appl. No. 11/919,491.
Official Action Dated Mar. 25, 2010 From the US Patent and Trademark Office Re.: U.S. Appl. No. 10/804,560.
Official Action Dated Sep. 25, 2009 From the US Patent and Trademark Office Re.: U.S. Appl. No. 10/526,708.
Official Action Dated Jun. 26, 2008 From the US Patent and Trademark Office Re.: U.S. Appl. No. 11/536,794.
Official Action Dated May 26, 2010 From the US Patent and Trademark Office Re.: U.S. Appl. No. 11/318,845.
Official Action Dated Oct. 26, 2012 From the US Patent and Trademark Office Re. U.S. Appl. No. 11/336,099.
Official Action Dated Apr. 27, 2010 From the US Patent and Trademark Office Re.: U.S. Appl. No. 10/570,576.
Official Action Dated Aug. 27, 2012 From the US Patent and Trademark Office Re.: U.S. Appl. No. 11/919,491.
Official Action Dated Mar. 27, 2008 From the US Patent and Trademark Office Re.: U.S. Appl. No. 10/804,560.
Official Action Dated Sep. 27, 2010 From the US Patent and Trademark Office Re.: U.S. Appl. No. 10/804,560.
Official Action Dated Apr. 28, 2011 From the US Patent and Trademark Office Re. U.S. Appl. No. 11/931,889.
Official Action Dated Apr. 28, 2011 From the US Patent and Trademark Office Re.: U.S. Appl. No. 11/931,889.
Official Action Dated Aug. 28, 2009 From the US Patent and Trademark Office Re.: U.S. Appl. No. 11/802,685.
Official Action Dated Aug. 28, 2009 From the US Patent and Trademark Office Re.: U.S. Appl. No. 11/932,064.
Official Action Dated Feb. 28, 2008 From the US Patent and Trademark Office Re. U.S. Appl. No. 09/980,748.
Official Action Dated Jun. 28, 2010 From the US Patent and Trademark Office Re.: U.S. Appl. No. 11/931,889.
Official Action Dated Apr. 29, 2009 From the US Patent and Trademark Office Re. U.S. Appl. No. 09/980,748.
Official Action Dated Sep. 29, 2010 From the US Patent and Trademark Office Re. U.S. Appl. No. 11/933,168.
Official Action Dated Apr. 30, 2010 From the US Patent and Trademark Office Re.: U.S. Appl. No. 11/931,724.
Official Action Dated Apr. 30, 2010 From the US Patent and Trademark Office Re.: U.S. Appl. No. 11/932,149.
Official Action Dated Aug. 30, 2006 From the US Patent and Trademark Office Re. U.S. Appl. No. 09/980,748.
Official Action Dated Aug. 30, 2012 From the US Patent and Trademark Office Re. U.S. Appl. No. 12/160,616.
Official Action Dated Oct. 30, 2012 From the US Patent and Trademark Office Re. U.S. Appl. No. 12/160,616.
Official Action Dated Aug. 31, 2007 From the US Patent and Trademark Office Re.: U.S. Appl. No. 11/536,794.
Official Action Dated Aug. 31, 2010 From the US Patent and Trademark Office Re.: U.S. Appl. No. 11/550,560.
Official Action Dated Jul. 31, 2008 From the US Patent and Trademark Office Re.: U.S. Appl. No. 11/318,845.
Official Action Dated Mar. 31, 2010 From the US Patent and Trademark Office Re.: U.S. Appl. No. 10/237,263.
Official Action Dated Mar. 31, 2011 From the US Patent and Trademark Office Re. U.S. Appl. No. 11/673,812.
Pre-Appeal Brief Request for Review Dated Aug. 9, 2011 From the US Patent and Trademark Office Re. U.S. Appl. No. 11/933,168.
Request for Ex Parte Reexamination of Patent No. 6,363,279—IDS Submitted Dec. 31, 2007 From the US Patent and Trademark Office Re.: U.S. Appl. No. 90/008,688.
Request for Ex Parte Reexamination of Patent No. 6,363,279—Notice of Intent to Issue Reexamination Certificate Dated Mar. 18, 2009 From the US Patent and Trademark Office Re.: U.S. Appl. No. 90/008,688.
Request for Ex Parte Reexamination of Patent No. 6,363,279—Official Action Dated Jun. 20, 2008 From the US Patent and Trademark Office Re.: U.S. Appl. No. 90/008,688.
Request for Ex Parte Reexamination of Patent No. 6,363,279—Order Granting Request Dated Nov. 5, 2007 From the US Patent and Trademark Office Re.: U.S. Appl. No. 90/008,688.
Request for Ex Parte Reexamination of Patent No. 6,363,279 Dated Jun. 8, 2007 From the US Patent and Trademark Office Re.: U.S. Appl. No. 90/008,688.
Request for Ex Parte Reexamination of Patent No. 6,363,279, Response to Official Action Dated Jun. 20, 2008 Submitted Aug. 20, 2008 From the US Patent and Trademark Office Re.: U.S. Appl. No. 90/008,688.
Request for Ex Parte Reexamination of US Patent No. 6,236,887—IDS Submitted Oct. 17, 2007 From the US Patent and Trademark Office Re.: U.S. Appl. No. 90/008,707.
Request for Ex Parte Reexamination of US Patent No. 6,236,887—Notice of Intent to Issue Ex Parte Examination Certificate Dated Mar. 19, 2009 From the US Patent and Trademark Office Re.: U.S. Appl. No. 90/008,707.
Request for Ex Parte Reexamination of US Patent No. 6,236,887—Official Action and IDS Considered Dated Jun. 20, 2008 From the US Patent and Trademark Office Re.: U.S. Appl. No. 90/008,707.
Request for Ex Parte Reexamination of US Patent No. 6,236,887—Official Action Granting Request for Ex Parte Examination Dated Aug. 17, 2007 From the US Patent and Trademark Office Re.: U.S. Appl. No. 90/008,707.
Request for Ex Parte Reexamination of US Patent No. 6,236,887 Dated Jun. 13, 2007 From the US Patent and Trademark Office Re.: U.S. Appl. No. 90/008,707.

(56) References Cited

OTHER PUBLICATIONS

Request for Ex Parte Reexamination of US Patent No. 6,298,268—Certificate of Reexamination Issued Mar. 7, 2006, U.S. Appl. No. 90/006,788.
Request for Ex Parte Reexamination of US Patent No. 6,298,268—IDS Considered Feb. 22, 2005, U.S. Appl. No. 90/006,788.
Request for Ex Parte Reexamination of US Patent No. 6,298,268—Notice of Intent to Issue Certificate of Reexamination Dated Mar. 29, 2005, U.S. Appl. No. 90/006,788.
Request for Ex Parte Reexamination of US Patent No. 6,298,268 Dated Oct. 10, 2003, U.S. Appl. No. 90/006,788.
Request for Ex Parte Reexamination of US Patent No. 6,298,268 Order Granting Request for Ex Parte Reexamination Dated Dec. 19, 2003, U.S. Appl. No. 90/006,788.
Request for Ex Parte Reexamination of US Patent No. 6,317,631—Amendment in Response to Official Action Dated Jun. 20, 2008, Filed Aug. 20, 2008 From the US Patent and Trademark Office Re.: U.S. Appl. No. 90/008,689.
Request for Ex Parte Reexamination of US Patent No. 6,317,631—IDS Dated Sep. 26, 2008 From the US Patent and Trademark Office Re.: U.S. Appl. No. 90/008,689.
Request for Ex Parte Reexamination of US Patent No. 6,317,631—IDS Dated Dec. 31, 2007 From the US Patent and Trademark Office Re.: U.S. Appl. No. 90/008,689.
Request for Ex Parte Reexamination of US Patent No. 6,317,631—Notice of Intent to Issue Certificate of Reexamination Dated Mar. 18, 2009 From the US Patent and Trademark Office Re.: U.S. Appl. No. 90/008,689.
Request for Ex Parte Reexamination of US Patent No. 6,317,631—Official Action Dated Jun. 20, 2008, U.S. Appl. No. 90/008,689.
Request for Ex Parte Reexamination of US Patent No. 6,317,631—Order Granting Reexamination Dated Nov. 5, 2007, U.S. Appl. No. 90/008,689.
Request for Ex Parte Reexamination of US Patent No. 6,317,631—IDS Dated Jun. 8, 2007, U.S. Appl. No. 90/008,689.
Request for Ex Parte Reexamination of US Patent No. 6,330,476—IDS Dated May 31, 2006.
Request for Ex Parte Reexamination of US Patent No. 6,330,476—Comments by 3rd Party Requestor, Response Thereto and Official Action Issued Jul. 16, 2008, U.S. Appl. No. 95/000,032.
Request for Ex Parte Reexamination of US Patent No. 6,330,476—Communication of Right to Appeal dated Jul. 16, 2008, U.S. Appl. No. 95/000,032.
Request for Ex Parte Reexamination of US Patent No. 6,330,476—IDS Filed May 4, 2007, U.S. Appl. No. 95/000,032.
Request for Ex Parte Reexamination of US Patent No. 6,330,476—Official Action by USPTO Issued Mar. 23, 2004, U.S. Appl. No. 95/000,032.
Request for Ex Parte Reexamination of US Patent No. 6,330,476—Order Granting Request for Reexamination Dated Mar. 23, 2004 From the US Patent and Trademark Office Re.: U.S. Appl. No. 95/000,032.
Request for Ex Parte Reexamination of US Patent No. 6,330,476 Dated Dec. 31, 2003 From the US Patent and Trademark Office Re.: U.S. Appl. No. 95/000,032.
Request for Ex Parte Reexamination of US Patent No. 6,463,324—Amendment in Response to Official Action Dated Aug. 1, 2007 Filed Oct. 1, 2007 From the US Patent and Trademark Office Re.: U.S. Appl. No. 90/008,312.
Request for Ex Parte Reexamination of US Patent No. 6,463,324—Certificate of Reexamination Dated Apr. 29, 2008 From the US Patent and Trademark Office Re.: U.S. Appl. No. 90/008,312.
Request for Ex Parte Reexamination of US Patent No. 6,463,324—Official Action—Notice of Intent to Reexamine Dated Jan. 24, 2008 From the US Patent and Trademark Office Re.: U.S. Appl. No. 90/008,312.
Request for Ex Parte Reexamination of US Patent No. 6,463,324—Official Action Dated Aug. 1, 2007 From the US Patent and Trademark Office Re.: U.S. Appl. No. 90/008,312.
Request for Ex Parte Reexamination of US Patent No. 6,463,324—Official Action, Interview Summary and References Considered Dated Nov. 6, 2007 From the US Patent and Trademark Office Re.: U.S. Appl. No. 90/008,312.
Request for Ex Parte Reexamination of US Patent No. 6,463,324 Dated Nov. 1, 2006 From the US Patent and Trademark Office Re.: U.S. Appl. No. 90/008,312.
Summons to Attend Oral Proceedings Pursuant to Rule 115(1) EPC Dated Jul. 4, 2011 From the European Patent Office Re.: Application No. 03794043.4.
Summons to Attend Oral Proceedings Pursuant to Rule 115(1) EPC Dated Dec. 22, 2008 From the European Patent Office Re.: Application No. 97929480.8.
Supplemental Response Dated Apr. 18, 2011 to Response of Apr. 10, 2011 to Official Action of Jan. 6, 2011 From the US Patent and Trademark Office Re.: U.S. Appl. No. 11/931,724.
Supplemental Response Dated Mar. 28, 2010 After an Interview of Mar. 4, 2010 From the US Patent and Trademark Office Re. U.S. Appl. No. 10/237,263.
Supplementary European Search Report and the European Search Opinion Dated Sep. 25, 2012 From the European Patent Office Re.: Application No. 06711186.4.
Supplementary European Search Report and the European Search Opinion Dated Nov. 28, 2008 From the European Patent Office Re.: Application No. 006759102.4.
Supplementary European Search Report and the European Search Opinion Dated Nov. 28, 2008 From the European Patent Office Re.: Application No. 05853465.2.
Supplementary European Search Report Dated Jun. 7, 2010 From the European Patent Office Re. Application No. 04770468.9.
Supplementary European Search Report Dated Jan. 12, 2011 From the European Patent Office Re. Application No. 05718889.8.
Supplementary Notice of Allowability Dated Nov. 22, 2006 From the US Patent and Trademark Office Re.: U.S. Appl. No. 10/804,560.
Supplementary Partial European Search Report Dated Nov. 4, 2010 From the European Patent Office Re. Application No. 04719312.3.
Translation of Decision of Rejection Dated Apr. 22, 2009 From the Japanese Patent Office Re.: Application No. 2004-534013.
Translation of Notice of Reasons for Rejection Dated Jul. 18, 2006 From the Japanese Patent Office Re.: Application No. 09-529637.
Translation of Notice of Reasons for Rejection Dated Apr. 27, 2010 From the Japanese Patent Office Re.: Application No. 2007-206282.
Translation of Notification of Reasons of Rejection Dated Apr. 12, 2010 From the Japanese Patent Office Re.: Application No. 2006-525265.
Translation of Office Action Dated Aug. 3, 2011 From the State Intellectual Property Office (SIPO) of the People's Republic of China Re.: Application No. 200480012687.5.
Translation of Office Action Dated Sep. 12, 2008 From the State Intellectual Property Office of the People's Republic of China Re.: Application No. 200480032636.9.
Translation of Office Action Dated Apr. 20, 2011 From the State Intellectual Property Office (SIPO) of the People's Republic of China Re.: Application No. 200480012687.5.
USPTO Public Print Out of Interference File Content of Interference Dated Apr. 4, 2011 From the US Patent and Trademark Office Re. Interference No. 105,765.
USPTO Public Print Out of Interference File Content of Interference Dated Apr. 4, 2011 From the US Patent and Trademark Office Re. Interference No. 105,768.
Adeghate et al. "Effect of Electrical Field Stimulation on Insulin and Glucagon Secretion From the Pancreas of Normal and Diabetic Rats", Hormone and Metabolic Research, 33(5): 281-289, May 2001. Abstract.
Antman et al. "Treatment of 150 Cases of Life-Threatening Digitalis Intoxication With Digoxin-Specific Fab Antibody Fragments", Circulation, 81(6): 1744-1752, 1990.
Bakker et al. "Beneficial Effects of Biventricular Pacing of Congestive Heart Failure", Pace, 17(Part II): 318, 1994.
Bargheer et al. "Prolongation of Monophasic Action Potential Duration and the Refractory Period in the Human Heart by Tedisamil, A New Potassium-Blocking Agent", Journal European Heart, 15(10): 1409-1414, 1994, Abstract.

(56) References Cited

OTHER PUBLICATIONS

Bergsten et al. "Synchronous Oscillations of Cytoplasmic Ca2+ and Insulin Release in Glucose-Stimulated Pancreatic Islets", The Journal of Biological Chemistry, 269(12): 8749-8753, Mar. 25, 1994.
Bers "Excitation Contraction Coupling and Cardiac Contractile Force", Internal Medicine, 237(2): 17, 1991, Abstract.
Blank et al. "Initial Interactions in Electromagnetic Field-Induced Biosynthesis", Journal of Cellular Physiology, 199: 359-363, 2004.
Borst et al. "Coronary Artery Bypass Grafting Without Cardiopulmonary Bypass and Without Interuption of Native Coronary Flow Using A Novel Anastomosis Site Restraining Device (Octupus)", Journal of the American College of Cardiology, 27(6): 1356-1364, 1996. Abstract only!.
Bouaziz et al. "Direct Electrical Stimulation of Insulin Secretion by Intact Murine Islets of Langerhans Through the Culture Support", Electromagnetic Biology and Medicine, 17(2): 171-184, 1998. Abstract.
Bronzino "Biomedical Engineering Handbook", IEEE Press/CRC Press, Chap. 82.5: 1288, 1995.
Burfeind et al "The Effects of Mechanical Cardiac Stabilization on Left Ventricular Performance", Europeari Journal of Cardio-Thoracic Surgery, 14: 285-289, 1998.
Cano et al. "Dose-Dependent Reversal of Dixogin-Inhibited Activity of an In-Vitro Na+K+ATPase Model by Digoxin-Specific Antibody", Toxicology Letters, 85(2): 107-1011, 1996.
Cazeau et al. "Multisite Pacing for End-Stage Heart Failure: Early Experience", Pacing and Clinical Electrophysiology, 19(11/Pt.2): 1748-1757, 1996. Abstract.
Cheng et al. "Calcium Sparks: Elementary Events Underlying Excitation-Contraction Coupling in Heart Muscle", Science, 262(5134): 740-744, 1993. Abstract.
Cooper "Postextrasystolic Potention. Do We Really Know What It Means and How to Use It?", Circulation, 88: 2962-2971, 1993.
Coulton et al. "Magnetic Fields and Intracellular Calcium; Effects on Lymphocytes Exposed to Conditions for 'Cyclotron Resonance'", Phys. Med. Biol., 38: 347-360, 1993, Abstract.
Devedeux et al. "Uterine Electromyography: A Critical Review", American Journal of Obstetric Gynecology, 169(6): 1636-1653, 1993.
Dillion "Optial Recordings in the Rabbit Heart Show That Defibrillation Strength Shocks Prolong the Duration of Depolarization and the Refractory Period", Circulation Research, 69: 842-856, 1991.
Dillon "Synchronized Repolarization After Defibrillation Shocks. A Possible Component of the Defibrillation Process Demonstration by Optical Recordings in Rabbit Heart", Circulation, 85(5): 1865-1878, 1992.
Erol-Yilmaz et al. "Reversed Remodelling of Dilated Left Sided Cardiomyopathy After Upgrading from VVIR to VVIR Biventricular Pacing", Europace, 4: 445-449, 2002.
Fain et al. "Improved Internal Defibrillation Efficacy With a Biphasic Waveform", American Heart Journal, 117(2): 358-364, 1989, Abstract.
Fleg et al. "Impact of Age on the Cardiovasvular Response to Dynamic Upright Exercise in Healthy Men and Women", Journal of Applied Physiologyl, 78: 890-900, 1995, Abstract.
Fleischhauer et al. "Electrical Resistances of Interstitial and Microvascular Space as Determinants of the Extracellular Electrical Field and Velocity of Propagation in Ventricular Myocardium", Circulation, 92: 587-594, 1995.
Foster et al. "Acute Hemodynamic Effects of Atrio—Biventricular Padng in Humans", The Society of Thoracic Surgeons, 59: 294-300, 1995, Abstract.
Franz "Bridging the Gap Between Basic Clinical Electrophysiology: What Can Be Learned From Monophasic Action Potential Recordings?", Journal Cardiovasc Electrophysiology, 5(8): 699-710, 1994, Abstract.
Franz "Method and Theory of Monophasic Action Potential Recording", Progress in Cardiovascular Diseases, 33(6): 347-368, 1991. Abstract.

Fromer et al. "Ultrarapid Subthreshold Stimulation for Termination of Atriventricular Node Reentrant Tachycardia", Journal of the American College Cardiology, 20: 879-883, 1992.
Fu et al. "System identification of Electrically Coupled Smooth Music Cells: The Passive Electrically Coupled Smooth Muscle Cells: The Passive Electrical Properties", IEEE Transactions on Biomedical Engineering, 38(11): 1130-1140, 1991.
Gardner "Natriuretic Peptides: Markers or Modulators of Cardiac Hypertrophy?", Trends in Endocrinology and Metabolism, 14(9): 411-416, Nov. 2003.
Gill et al. "Refractory Period Extension During Ventricular Pacing at Fibrillatory Pacing Rates", Pacing and Clinical Elctrophysiology, 20(3): 647-653, 1997, Abstract.
Gilmour Jr. et al. "Dynamics of Circus Movement Re-Entry Across Canine Purkinje Fibre-Muscle Junctions", The Journal of Physiology, 476(3): 473-485, 1994.
Gilmour Jr. et al. "Overdrive Suppression of Conduction at the Canine Purkinje-Muscle Junction", Circulation, 76(6): 1388-1396, 1987.
Gold et al. "Evidence That Glucose 'Marks' Beta Cells Resulting in Preferential Release of Newly Synthesized Insulin", Science, 218(4567): 56-58, Oct. 1, 1982. Abstract.
Gomis et al. "Oscillatory Patterns of Electrical Activity in Mouse PancreaticIslets of Langerhans Recorded in Vivo", Pfl?gers Archiv European Journal of Physiology, 432(3): 510-515, 1996.
Gussoni et al. "Dystrophin Expression in the MDX Mouse Restored by Stem Cell Transplantation", Nature, 401(6751): 390-394, 1999.
Ham et al. "Classification of Cardiac Arrhythmias Using Fuzzy Artmap", IEEE Transactions on Biomedical Engineering, 43(4): 425-429, 1996, Abstract.
Hammond et al. "Motor Innervation of the Cricopharyngeus Muscle by the Recurrent Lanryngeal Nerve", Journal of Applied Physiology, JAP, 83: 89-94, 1997.
Highfill et al. "Large-Scale Production of Murine Bone Marrow Cells in an Airlift Packed Bed Bioreactor", Biotechnology and Bioengineering, 50(5): 514-520, 1996.
Hinke et al. "Dipeptidyl Peptidase IV (DPIV/CD26) Degradation of Glucagon. Characterization of Glucagon Degradation Products and DPIV-Resistant Analogs", The Journal of Biological Chemistry, 275(6): 3827-3834, Feb. 11, 2000.
Hoffman et al. "Effects of Postextrasystolic Potentiation on Normal and Failing Hearts", Bulletin of the New York Academy of Medicine, 41(5): 498-534, 1965.
Holst et al. "Nervous Control of Pancreatic Endocrine Secretion in Pigs. I. Insulin and Glucagon Responses to Electrical Stimulation of the Vagus Nerves", Acta Physiologica Scandinavica, 111(1): 1-7, Jan. 1981. Abstract.
Holst et al. "Nervous Control of Pancreatic Endocrine Secretion in Pigs. II. The Effect of Pharmacological Blocking Agents on the Response to Vagal Stimulation", Acta Physiologica Scandinavica, 111(1): 9-14, 1981. Abstract.
Horner et al. "Electrode for Recording Direction of Activation, Conduction Velocity and Monophasic Action Potential of Myocardium", American Journal of Physiology, 272(4): H1917-H1927, 1997. Abstract.
Jaremko et al. "Advances Towards the Implantable Artifical Pancreas for Treatment of Diabetes", Diabetes Care, 21(3): 444-450, 1998.
Josephson "Clinical Cardiac Electrophysiology: Techniques and Interpertations", Lea & Febiger, 2nd Ed., 2 P., 1991.
King et al. "The Inotropic Action of Paired Pulse Stimulation in the Normal and Failing Heart: An Experimental Study", Cardiovascular Research, 2: 122-129, 1968.
Knisley et al. "Effect of Field Stimulation on Cellular Repolarization in Rabbit Myocardium. Implications for Reentry Induction", Circulation Research, 70(4): 707-715, Apr. 1992.
Knisley et al. "Prolongation and Shortening of Action Potentials by Electrical Shocks in Frog Ventricular Muscle", American Journal of Physiology, 266(6): H2348-H2358, 1994, Abstract.
Koller et al. "Relation Between Repolarization and Refractoriness During Programmed Electrical Stimulation in the Human Right Ventricle", Circulation, 91(9): 2378-2384, 1995, Abstract.
Kurose et al. "Glucagon, Insulin and Somatostatin Secretion in Response to Sympathetic Neural Activation in Streptozotocin-In-

(56) References Cited

OTHER PUBLICATIONS duced Diabetic Rats. A Study With the Isolated Perfused Rat Pancreas in Vitro", Diabetologia, 35(11): 1035-1041, Nov. 1992. Abstract.
Langberg et al. "Identification of Ventricular Tachycardia With Use of the Morphology of the Endocardial Electrogram", Circulation, 77(6): 1363-1369, 1988.
Lindstroem et al. "Intracellular Calcium Oscillations in A T-Cell Line After Exposure to Extremely-Low-Frequency Magnetic Fields With Variable Frequencies and Flux Densities", Bioelectromagnetics, 16(1): 41-47, 1995. Abstract.
Loginov et al. "Effects of an Impulse Electromagnetic Field on Calcium Ion Accumulation in the Sarcoplasmic . . . ", Kosm. Biol. Aviakosm. Med., 15: 51-53, 1991.
Lubart et al. "Effect of Light on Calcium Transport in Bull Sperm Cells", Journal of Photochemistry and Photobiology B, Biology, 15(4): 337-341, Sep. 15, 1992. Abstract.
Luiken et al. "Contraction-Induced Fatty Acid Translocase/CD36 Translocation in Rat Cardiac Myocytes Is Mediated Through AMP-Activated Protein Kinase Signaling", Diabetes, 52: 1627-1634, 2003.
Magnus et al. "Model of Beta-Cell Mitochondrial Calcium Handling and Electrical Activity. II. Mitochondrial Variables", American Journal of Physiology, Cell Physiology, 274(43): C1174-C1184, 1998.
Matheny et al. "Vagus Nerve Stimulation as a Method to Temporarily Slow or Arrest the Heart", Annals of Thoracic Surgery, 63(6): S28-29, 1997, Abstract.
McVeigh et al. "Noninvasive Measurement of Transmural Gradients in Myocardial Strain With MR Imaging", Radiology, 180(3): 677, 679-684, 1991.
Mercando et al. "Automated Detection of Tachycardias by Antitachycardia Devices", Cardiac Electrophysiology: From Cell to Bedside, Chap.100: 943-948, 2004.
Meurer et al. "Properties of Native and in Vitro Glycosylated Forms of the Glucogan-Like Peptide-1 Receptor Antagonist Exendin(9-39)", Metabolism: Clinical and Experimental, 48(6): 716-724, Jun. 1999. Abstract.
Misler et al. "Electrophysiology of Stimulus-Secretion Coupling in Human Beta-Cells", Diabetes, 41(10): 1221-1228, Oct. 1992. Abstract.
Moran et al. "Digoxin-Specific Fab Fragments Impair Renal Function in the Rat", Journal of Pharmacy and Pharmacology, 46(10): 854-856, 1994, Abstract.
Morse et al. "A Guide to Cardiac Pacemakers, Defibrillators and Related Products", Droege Computing Services, Inc., vol. 1, Nov. 19, 1996.
Nadal et al. "Homologous and Heterologous Asynchronicity Between Identified ?-, ?- and ?- Cells Within Intact Islets of Langerhans in the Mouse", Journal of Physiology, 517(Pt.1): 85-93, 1999.
Nannini et al. "Muscle Recruitment With Intrafascicular Electrodes", IEEE Transactions on Biomedical Engineering, 38: 769-776, 1991, Abstract.
Ohinata et al. "Proadrenomedullin N-Terminal 20 Peptide (PAMP) Elevates Blood Glucose Levels Via Bombesin Receptor in Mice", FEBS Letters, 473(2): 207-211, May 2000. Abstract.
Palti et al. "Islets of Langerhans Generate Wavelike Electric Activity Modulated by Glucose Concentration", Diabetes, 45(5): 595-601, May 1996. Abstract.
Park et al. "Significant Cholinergic Role in Secretin-Stimulated Exocrine Secretion in Isolated Rat Pancreas", American Journal of Physiology, AJP—Gastrointestinal and Liver Physiology, 274(2): G413-G418, Feb. 1998.
Patterson et al. "Therapeutic Angiogenesis: The New Electrophysiology?", Circulation, 99(20): 2614-2616, 1999.
Paul et al. "Automatic Recognition of Ventricular Arrhythmias Using Temporal Electrogram Analysis", PACE, 14: 1265-1273, 1991.
Pokrovsky et al. "Physiology of Man", 1: 82-83, 94, 2: 42, 54, (1997).
Porksen et al. "Section 6: Pulsatile and Phasic Insulin Release in Normal and Diabetic Man. Pulsatile Insulin Secretion: Detection, Regulation, and Role in Diabetes", Diabetes, 51(Suppl.1): S245-S254, Feb. 2002.
Pumir et al. "Control of Rotating Waves in Cardiac Muscle: Analysis of the Effect of Electric Fields", Proceedings of the Royal Society B: Biological Sciences, 257(1349): 129-134, 1994. Abstract.
Ranjan et al. "Electrical Stimulation of Cardiac Myocytes", Annals of Biomedical Engineering, 23(6): 812-821, 1995, Abstract.
Rivera et al. "Regulation of Protein Secretion Through Controlled Aggregation in the Endoplasmic Reticulum", Science, 287(5454): 826-830, Feb. 4, 2000. Abstract.
Saksena et al. "Prevention of Recurrent Atrial Fibrillation With Chronic Dual-Site Right Atrial Pacing", Journal of the American College of Cardiology, 28(3): 687-694, 1996, Abstract.
Sakuma et al. "A Model Analysis of Aftereffects of High-Intensity DC Stimulation on Action Potential of Ventricular Muscle", IEEE Transactions on Biomedical Engineering, 45(2): 258-267, 1998.
San Mauro et al. "Nerves of the Heart: A Comprehensive Review With A Clinical Point of View", Neuroanatomy, 8: 28-31, 2009.
Saveliev et al. "Guidebook on Clinical Endoscopy", Moscow Medicine, p. 21, 35, Extract, 1985.
Schirra et al. "Exendin(9-39) Amide Is an Antagonist of Glucagon-Like Peptide-1(7-36) Amide in Humans", Journal of Clinical Investigation, 101(7): 1421-1430, Apr. 1998.
Schirra et al. "Mechanisms of the Antidiabetic Action of Subcutaneous Glucagon-Like Peptide-1 (17-36) Amide in Non-Insulin Dependent Diabetes Mellitus", Journal of Endocrinology Ltd., 156(1): 177-186, Jan. 1998. Abstract.
Schwartz et al. "Exposure of Frog Hearts to CW or Amplitude-Modified VHF Fields: Selective Efflux of Calcium Ions at 16 Hz", Bioelectromagnetics, 11(4): 349-358, 1990, Abstract.
Serre et al. "Exendin-(9-39) Is an Inverse Agonist of the Murine Glucagon-Like Peptide-1 Receptor: Implications for Basal Intracellular Cyclic Adenosine 3',5'-Monophosphate Levels and ?-Cells Glucose Competence", Endocrinology, 139(11): 4448-4454, 1998.
Shah et al. "Impact of Lack of Suppression of Glucagon on Glucose Tolerance in Humans", American Journal of Physiology, AJP—Endocrinology and Metabolism, 277(2 Pt.1): E283-E290, 1999.
Shmit et al. "Physiology of Man", Moscow Medicine, Mir, 1: 78, 1996.
Shuba et al. "Physiology of Vessel Smooth Muscles", Kiev Naukova Dumka, 142: 11-15, 142, 1988.
Shumaik et al. "Oleander Poisoning: Treatment With Digoxin-Specific Fab Antibody Fragments", Annals of Emergency Medicine, 17(7): 732-735, 1988.
Singh et al. "Effects of Islet Hormones on Nerve-Mediated and Acetylcholine-Evoked Secretory Responses in the Isolated Pancreas of Normal and Diabetic Rats", International Journal of Molecular Medicine, 1(3): 627-634, Mar. 1998. Abstract.
Skale et al. "Inhibition of Premature Ventricular Extrastimuli by Subthreshold Conditioning Stimuli", Journal of the American College of Cardiology, 6: 133-140, 1985. Abstract.
Solomonow et al. "Control of Muscle Contractile Force Through Indirect High-Frequency Stimulation", American Journal of Physical Medicine, 62(2): 71-82, Apr. 1983. Abstract.
Soria et al. "Cytosolic Calcium Oscillations and Insulin Release in Pancreatic Islets of Langerhans", Diabetes & Metabolism, 24: 37-40, 1998.
Stevenson et al. "Electrophysiologic Characteristics of Ventricular Tachycardia or Fibrillation in Relation to Age of Myocardial Infarction", The American Journal of Cardiology, 57(6): 387-391, Feb. 15, 1986. Abstract.
Sukhorukov et al. "The Effect of Electrical Deformation Forces on the Electropermeabilization of Erythrocyte Membranes in Low-and High-Conductivity Media", The Journal of Membrane Biology, 163(3): 235-245, 1998. Abstract.
Sutton et al. "The Foundation of Cardiac Pacing, Part I: An Illustrated Practical Guide to Basic Pacing", The Bakken Research Center Series, Chap.4: 50-59, 1991.
Sutton et al. "What Is A Pacemaker?", The Foundations of Cardiac Pacing, Part I: An Illustrated Practical Guide to Basic Pacing, Chap. 4.5: 73-74, 1991.

(56) References Cited

OTHER PUBLICATIONS

Sweeny et al. "Countershock Strength-Duration Relationship for Myocardial Refractory Period Extension", Academic Emergency Medicine, 2(1): 57-62, 1995, Abstract.
Sweeny et al. "Refractory Interval After Transcardiac Shocks During Ventricular Fibrillation", Circulation, 94(11): 2947-2952, 1996.
Sweeny et al. "Ventricular Refractory Period Extension Caused by Defibrillation Shocks", Circulation, 82(3): 965-972, 1990.
Swerdlow et al. "Cardiovascular Collapse Caused by Electrocardiographically Silent 60-Hz Intracardiac Leakage Current: Implications for Electrical Safety", Circulation, 99: 2559-2564, 1999.
Talit et al. "The Effect of External Cardiac Pacing on Stroke Volume", Pace, 13(5): 598-602, 1990. Abstract.
Taniguchi et al. "Inhomogeneity of Cellular Activation Time and Vmax in Normal Myocardial Tissue Under Electrical Field Stimulation", Am. J. Physiol., 267: H694-H705, 1994, Abstract.
Thakor et al. "Effect of Varying Pacing Waveform Shapes on Propagation and Hemodynamics in the Rabbit Heart", The Americal Journal of Cardiology, 79(6A): 36-43, 1997, Abstract.
Todd et al. "Subcutaneous Glucagon-Like Peptide I Improves Postprandial Glycaemic Control Over A 3-Week Period in Patients With Early Type 2 Diabetes", Clinical Science, 95: 325-329, 1998.
Tsong "Electroporation of Cell Membranes", Biophysical Journal, 60: 297-306, 1991.
Valdeolmillos et al. "In Vivo Synchronous Membrane Potential Oscillations in Mouse Pancreatic Beta-Cells: Lack of Co-Ordination Between Islets", Journal of Physiology, 493(1): 9-18, 1996.
Van Riper et al. "Electrical Field Stimulation-Mediated Relaxation of a Rabbit Middle Cerebral Artery. Evidence of a Cholinergic Endothelium-Dependent Component", Circulation Research, 70(6): 1104-1112, Jun. 1992.
Venier et al. "Electrophysiologic Basis for T Wave Alternans as an Index of Vulnerability to Ventricular Fibrillation", Journal of Cardiovascular Electrophysiology, 5(5): 445-461, 1994. Abstract.
Wang et al. "Islet Amyloid Polypeptide Tonally Inhibits Beta-, Alpha-, and Delta-Cell Secretion in Isolated Rat Pancreatic Islets", American Journal of Physiology, AJP—Endocrinology and Metabolism, 276(1 Pt.1): E19-E24, 1999.
Webster "Design of Cardiac Pacemakers", IEEE Press, P. xi-xiii, 1995.
Webster "Electrodes, Leads, and Biocompatibility", Design of Cardiac Pacemakers, IEEE Press, p. 141-144, 1995.
Wessale et al. "Stroke Volume and the Three Phase Cardiac Output Rate Relationship With Ventricular Pacing", PACE, 13: 673-680, 1990.
Windle et al. "Subthreshold Conditioning Stimuli Prolong Human Ventricular Refractoriness", American Journal of Cardiology, 57(6): 381-386, 1986. Abstract.
Wirtzfeld et al. "Physiological Pacing: Present Status and Future Developments", Pace, 10(Part I): 41-57, 1987. Abstract.
Wright et al. "Structure of Fab hGR-2 F6, A Competitive Antagonist of the Glucagon Receptor", Acta Crystallographica, Section D, Biological Crystallography, 56(Pt.5): 573-580, May 2000. Abstract.
Xue et al. "Neural-Network-Based Adaptive Matched Filtering for QRS Detection", IEEE Transactions on Biomedical Engineering, 39(4): 317-329, 1992. Abstract.
Yokoyama "The Phase of Supernormal Excitation in Relation to the Strength of Subthreshold Stimuli", Japanese Heart Journal, 17(3): 315-325, May 1976.
Yonemura et al. "Amelioration of Diabetes Mellitus in Partially Depancreatized Rats by Poly(ADP-Ribose) Synthetase Inhibitors. Evidence of Islet B-Cell Regeneration", Diabetes, 33(4): 401-404, Apr. 1984. Abstract.
Zhou et al. "Prevention of Action Potentials During Extracellular Electrical Stimulation of Long Duration", Journal of Cardiovascular & Electrophysiology, 8(7): 779-789, 1997. Abstract.
Zipes et al. "Cardiac Electrophysiology—From Cell to Bedside", Saunders Co., 4th Ed., 1990.
Communication Pursuant to Article 94(3) EPC Dated Mar. 11, 2008 From the European Patent Office Re.: Application No. 06127216.7.
Communication Under Rule 71(3) EPC Dated Oct. 7, 2008 From the European Patent Office Re.: Application No. 06127216.7.
Notice of Allowance Dated Aug. 9, 2010 From the US Patent and Trademark Office Re.: U.S. Appl. No. 11/736,183.
Notice of Allowance Dated Feb. 15, 2011 From the US Patent and Trademark Office Re.: U.S. Appl. No. 11/932,963.
Notice of Allowance Dated Apr. 19, 2010 From the US Patent and Trademark Office Re.: U.S. Appl. No. 11/932,812.
Notice of Allowance Dated Mar. 29, 2012 From the US Patent and Trademark Office Re.: U.S. Appl. No. 11/736,183.
Notice of Reason for Rejection Dated Jun. 12, 2007 From the Japanese Patent Office Re.: Application No. 2000-502823.
Notice of Reasons for Rejection Dated Oct. 3, 2006 From the Japanese Patent Office Re.: Application No. 2000-502823.
Office Action Dated Nov. 29, 2004 From the Israeli Patent Office Re.: Application No. 133902.
Official Action Dated Mar. 8, 2010 From the US Patent and Trademark Office Re.: U.S. Appl. No. 11/736,183.
Official Action Dated Dec. 11, 2009 From the US Patent and Trademark Office Re.: U.S. Appl. No. 11/932,881.
Official Action Dated Sep. 15, 2009 From the US Patent and Trademark Office Re.: U.S. Appl. No. 11/736,183.
Official Action Dated Jun. 22, 2010 From the US Patent and Trademark Office Re.: U.S. Appl. No. 11/736,183.
Official Action Dated Feb. 23, 2010 From the US Patent and Trademark Office Re.: U.S. Appl. No. 11/932,963.
Official Action Dated Jun. 26, 2009 From the US Patent and Trademark Office Re.: U.S. Appl. No. 11/932,812.
Official Action Dated Jun. 28, 2010 From the US Patent and Trademark Office Re.: U.S. Appl. No. 11/932,963.
Official Action Dated Aug. 31, 2011 From the US Patent and Trademark Office Re.: U.S. Appl. No. 11/736,183.
Requisition by the Examiner Dated Sep. 5, 2008 From the Canadian Intellectual Property Office Re.: Application No. 2,296,632.
Requisition by the Examiner Dated Jul. 14, 2004 From the Canadian Intellectual Property Office Re.: Application No. 2,296,632.
Requisition by the Examiner Dated Nov. 23, 2006 From the Canadian Intellectual Property Office Re.: Application No. 2,296,632.
Antoni et al. "Polarization Effects of Sinusoidal 50-Cycle Alternating Current on Membrane Potential of Mammalian Cardiac Fibres", Pfl?gers Archiv European Journal of Physiology, 314(4): 274-291, 1970. Abstract.
Babsky et al. Translation of Physiology of Man, Moscow Medicine, p. 115, 348-351, 376, Extracts, (1972).
Devedeux et al. "Uterine Electromyography: A Critical Review", American Journal of Obstetric Gynecology, 169: 1636-1653, 1993.
Holst et al. "Nervous Contril of Pancreatic Endocrine Secretion in Pigs. I. Insulin and Glucagon Responses to Electrical Stimulation of the Vagus Nerves", Acta Physiologica Scandinavica, 111(1): 1-7, Jan. 1981. Abstract.
Holst et al. "Nervous Control of Pancreatic Endocrine Secretion in Pigs. II. The Effect of Pharmacological Blocking Agents on the Response to Vagal Stimulation", Acta Physiologica Scandinavica, 111 (1): 9-14, Jan. 1981. Abstract.
Pokrovsky et al. Physiology of Man, 1: 82-83, 94, 2: 42, 54, (1997).
Saveliev et al. Guidebook on Clinical Endoscopy, p. 21, 35, Extract, (1985).
Shmit et al. Physiology of Man, 1: 78, 1996.
Shuba et al. Physiology of Vessel Smooth Muscles, p. 11-15, 142, 1988.
Van Riper et al. "Electrical Field Stimulation—Mediated Relaxation of A Rabbit Middle Cerebral Artery. Evidence of a Cholinergic Endothelium-Dependent Component", Circulation Research, 70: 1104-1112, 1992.

\* cited by examiner

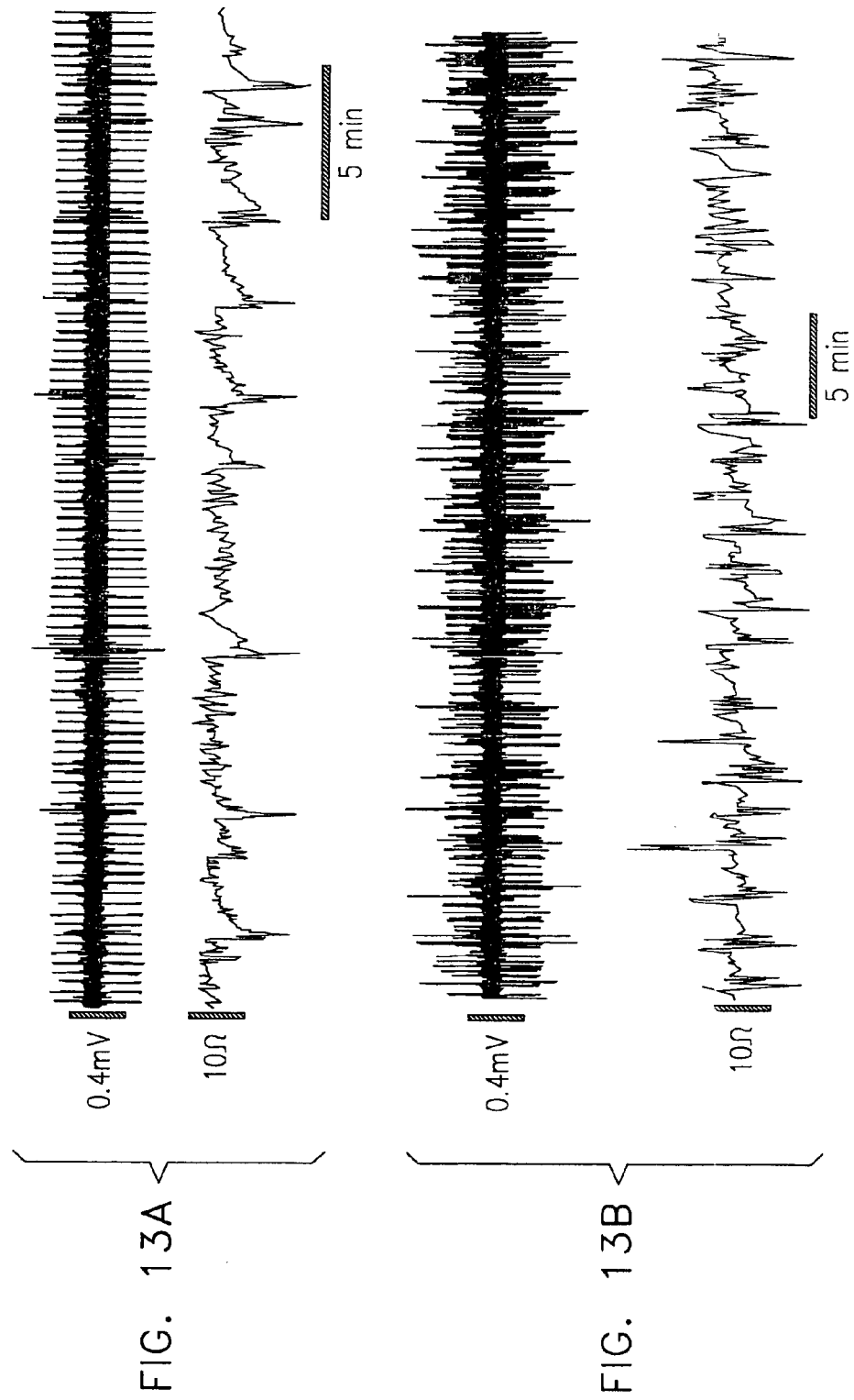

GASTROINTESTINAL ELECTRICAL THERAPY

CROSS-REFERENCE TO RELATED APPLICATIONS

The present application is the U.S. National Stage of International Application No. PCT/IL2011/000116, filed Feb. 1, 2011, which claims priority from (a) US Provisional Application Ser. No. 61/300,292, filed Feb. 1, 2010, entitled, "Electrical stimulation for treating gastroparesis and other conditions," and (b) US Provisional Application Ser. No. 61/406,774, filed Oct. 26, 2010, entitled, "Gastric electrical therapy for improving blood glucose level," each of which Applications is assigned to the assignee of the present application and is incorporated herein by reference.

FIELD OF THE APPLICATION

The present invention relates generally to techniques for electrical stimulation, and specifically to apparatus and methods for gastrointestinal stimulation for treating medical conditions.

BACKGROUND OF THE APPLICATION

Diabetes mellitus includes a cluster of diseases distinguished by chronic hyperglycemia that result from the body's failure to produce and/or use insulin, a hormone produced by β-cells in the pancreas that plays a vital role in metabolism. Symptoms include increased thirst and urination, hunger, weight loss, chronic infections, slow wound healing, fatigue, and blurred vision. Diabetes can also comprise abnormalities of carbohydrate, fat, and protein metabolism attributed to the deficient action of insulin on target tissues resulting from insulin insensitivity or lack of insulin.

Type 2 diabetes is the most common form of diabetes, which typically develops as a result of a relative, rather than absolute, insulin deficiency, in combination with the body's failure to use insulin properly (also known in the art as "insulin resistance"). Type 2 diabetes often manifests in persons, including children, who are overweight. Other risk factors include high cholesterol, high blood pressure, ethnicity, and genetic factors, such as a family history of diabetes. The majority of patients with type 2 diabetes are obese, and obesity itself may cause or aggravate insulin resistance.

Gastroparesis is a condition characterized by delayed gastric emptying and associated upper gastrointestinal (GI) symptoms. Paresis of the stomach causes food to remain in the stomach for a longer period of time than normal. Diabetic gastroparesis affects many patients who suffer from diabetes.

U.S. Pat. No. 6,600,953 to Flesler et al., which is incorporated herein by reference, describes apparatus for treating a condition such as obesity. The apparatus includes a set of one or more electrodes, which are adapted to be applied to one or more respective sites in a vicinity of a body of a stomach of a patient. A control unit is adapted to drive the electrode set to apply to the body of the stomach a signal, configured such that application thereof increases a level of contraction of muscle tissue of the body of the stomach, and decreases a cross-sectional area of a portion of the body of the stomach for a substantially continuous period greater than about 3 seconds.

PCT Patent Publication WO 99/03533 to Ben-Haim et al., entitled, "Smooth muscle controller," and U.S. patent application Ser. No. 09/481,253 in the national phase thereof, both of which are incorporated herein by reference, describe apparatus and methods for applying signals to smooth muscle so as to modify the behavior thereof. In particular, apparatus for controlling the stomach is described in which a controller applies an electrical field to electrodes on the stomach wall so as to modify the reaction of muscle tissue therein to an activation signal, while not generating a propagating action potential in the tissue.

U.S. Pat. No. 6,571,127 to Ben-Haim et al., which is incorporated herein by reference, describes methods of increasing contractile force and/or the motility of a GI tract. A first method comprises selecting a portion of the GI tract and applying a non-excitatory electric field to the portion, which field increases the force of contraction at the portion.

Sanmiguel C P et al., in an article entitled, "Gastric Electrical Stimulation with the TANTALUS® System in Obese Type 2 Diabetes Patients: Effect on Weight and Glycemic Control," J Diabetes Sci Technol 3(4):964-970 (July 2009), which is incorporated herein by reference, describes gastric electrical stimulation (GES) using the TANTALUS® System, which consists of an implantable pulse generator connected to gastric electrodes. The system is designed to automatically detect when eating starts and only then deliver sessions of gastric electrical stimulation (GES) with electrical pulses that are synchronized to the intrinsic antral slow waves. The authors report the effect of this type of GES on weight loss and glucose control in fourteen overweight/obese subjects with type 2 diabetes mellitus (T2DM), on oral antidiabetes medication. Gastric electrical stimulation was initiated four weeks after implantation. Weight, HbAlc, fasting blood glucose, blood pressure, and lipid levels were assessed during the study period. Eleven subjects reached the 6-month treatment period endpoint. Gastric electrical stimulation was well tolerated by all subjects. In those patients completing 6 months of therapy, HbAlc was reduced significantly from 8.5±0.7% to 7.6±1%, p<0.01. Weight was also significantly reduced from 107.7±21.1 to 102.4±20.5 kg, p<0.01. The improvement in glucose control did not correlate with weight loss (R2=0.05, p=0.44). A significant improvement was noted in blood pressure, triglycerides, and cholesterol (low-density lipoprotein only). The authors conclude that short-term therapy with the TANTALUS System improves glucose control, induces weight loss, and improves blood pressure and lipids in obese T2DM subjects on oral antidiabetes therapy.

Sanmiguel C P et al., in an article entitled, "The TANTALUS™ System for obesity: effect on gastric emptying of solids and ghrelin plasma levels," Obesity Surgery 17:1503-1509 (2007), which is incorporated herein by reference, describes gastric electrical stimulation, using the implantable TANTALUS System, as a treatment for obesity. The system is described as delivering nonstimulatory electrical signals synchronized with gastric slow waves, resulting in stronger contractions. The study tested the effect of GES on gastric emptying of solids and on ghrelin and insulin blood levels in obese subjects.

UltraFlex Implantable Gastric Lead data sheet (MetaCure (USA), Orangeburg, N.Y.), which is incorporated herein by reference, provides information regarding this lead.

The following references, all of which are incorporated herein by reference, may be of interest:

U.S. Pat. No. 6,317,631 to Ben-Haim et al.
U.S. Pat. No. 6,415,178 to Ben-Haim et al.
U.S. Pat. No. 6,947,792 to Ben-Haim et al.
U.S. Pat. No. 6,993,391 to Flesler et al.
U.S. Pat. No. 7,120,497 to Ben-Haim et al.
U.S. Pat. No. 7,218,963 to Ben-Haim et al.
U.S. Pat. No. 7,221,978 to Ben-Haim et al.
U.S. Pat. No. 7,502,649 to Ben-Haim et al.

US Patent Application Publication 2002/0161414 to Flesler et al.

US Patent Application Publication 2003/0055464 to Darvish et al.

US Patent Application Publication 2007/0027493 to Ben-Haim et al.

US Patent Application Publication 2007/0092446 to Haddad et al.

US Patent Application Publication 2007/0179556 to Ben-Haim et al.

US Patent Application Publication 2008/0065168 to Bitton et al.

US Patent Application Publication 2009/0281449 to Thrower et al.

PCT Publication WO 97/25098 to Ben-Haim et al.
PCT Publication WO 00/53257 to Darwish et al.
PCT Publication WO 01/66183 to Darvish et al.
PCT Publication WO 01/91854 to Harel et al.
PCT Publication WO 02/053093 to Policker et al.
PCT Publication WO 02/082968 to Policker et al.
PCT Publication WO 03/045493 to Harel et al.
PCT Publication WO 04/112563 to Ben-Haim et al.
PCT Publication WO 04/112883 to Glasberg et al.
PCT Publication WO 04/021858 to Harel et al.
PCT Publication WO 05/007232 to Ben-Haim et al.
PCT Publication WO 05/087310 to Harel et al.
PCT Publication WO 06/018851 to Kliger et al.
PCT Publication WO 06/087712 to Ben-Haim et al.
PCT Publication WO 06/102626 to Policker et al.
PCT Publication WO 06/129321 to Policker et al.
PCT Publication WO 07/080,595 to Levi et al.
PCT Publication WO 08/117,296 to Spehr et al.
PCT Publication WO 08/139,463 to Policker et al.

Bohdjalian A et al., "One-year experience with Tantalus: a new surgical approach to treat morbid obesity," Obes Surg. 16(5):627-34 (May 2006)

Bohdjalian A et al., "Improvement in glycemic control in morbidly obese type 2 diabetic subjects by gastric stimulation," Obes Surg 19(9):1221-7 (September 2009) (Epub 2009 Jul. 3)

SUMMARY OF THE APPLICATION

In some embodiments of the present invention, gastrointestinal (GI) apparatus is provided for applying electrical stimulation to a GI tract of a patient. The apparatus comprises a set of one or more electrode contact surfaces which are applied to one or more sites of the GI tract, such as the stomach, e.g., sites of a fundus of the stomach. A control unit drives the electrode set to apply an electrical signal to the stomach that improves a blood glucose level of the patient, such as normalizes the level, acutely and/or chronically (i.e., over an extended period of time, such as at least three months). Typically, the apparatus applies the stimulation chronically, i.e., on a long-term basis, such as for at least three months. The apparatus is configured to treat a condition of the patient, such as diabetes (type 2 or type 1), metabolic syndrome, impaired glucose tolerance (IGT), impaired fasting glycemia (IPG), gastroparesis, or another condition or co-morbidity, such as hypertension and/or hyperlipidemia. This improvement in blood glucose level is sometimes accompanied by a reduction in the patient's body weight.

For some applications, the control unit applies the stimulation (i.e., the therapy) continuously, for example at least once every minute throughout a 24-hour period, such as at least once every second, or at least several times every second (e.g., at least 10 times every second) throughout the 24-hour period. For other applications, the control unit applies the stimulation (i.e., the therapy) intermittently. For example, the stimulation may be applied during a plurality of periods of time, each of which has a duration of at least one minute, such as at least one hour, alternating with intermittent reduced-stimulation periods (typically non-stimulation periods), e.g., having durations of at least one minute, such as at least one hour. Optionally, the commencement or cessation of signal application may be based on an external or sensed input (e.g., detection of eating). It is noted that during both continuous and intermittent stimulation, the waveform of the signal is itself not necessarily continuous. For example, the signal may include multiple bursts or pulses. As used in the present application, including in the claims, "eating" is to be understood as including eating and/or drinking of solids, liquids, and/or solid/liquid mixtures, unless specifically otherwise indicated.

The control unit is typically configured to apply stimulation during at least one period each day (i.e., each 24-hour period), such as at least two, three, or ten periods per day. For some applications, the control unit is configured to apply the stimulation upon detecting eating of the patient (i.e., either solids or liquids), and/or upon detecting eating of certain types of food (e.g., solid foods, rather than liquid foods, and/or high-caloric foods, rather than low- or non-caloric food). Alternatively or additionally, for some applications the control unit is configured to modify one or more parameters of the stimulation upon detecting eating and/or eating of certain foods. For example, stimulation may be inhibited upon detection of eating. The control unit may use techniques for detecting eating and/or characterizing ingested foods that are described in one or more of the patents and/or patent application publications incorporated by reference hereinbelow.

As used in the present application, including in the claims, "chronically improving" a blood glucose level means effecting a reduction in a level of HbA1c, and "normalizing" a blood glucose level means reducing the HbA1c level below a threshold value clinically considered normal, such as below 7%, or below 6%.

The chronic improvement in blood glucose level may, for example, be mediated by (a) reduced insulin resistance, (b) a reduction in fasting glucose levels, (c) a reduction in a rise in glucose level in response to eating, (d) a reduction in postprandial glucose levels, (e) an improvement in hormone levels, such as hormones related to (e.g., secreted by) the gastrointestinal system (e.g., insulin levels, ghrelin levels, glucagon levels, pancreatic polypeptide levels, and/or glucagon-like peptide-1 (GLP-1) levels), (f) modulation of absorption of nutrients, and/or (g) an effect of the stimulation on food ingestion, processing, and/or digestion. As used in the present application, including in the claims, the "gastrointestinal system" comprises the stomach (including the fundus and the antrum), the pancreas, the small intestine (including the duodenum, jejunum, and ileum), the large intestine, the liver, and the gall bladder. Application of the signals described herein, in accordance with applications of the present invention, may cause some or all of these mediating mechanisms. In addition, the inventors hypothesize that at least a portion of the improvement in blood glucose (chronic or acute) caused by application of the signal may be mediated by modulation of secretion of ghrelin, which generates signals for metabolic balance, and may affect blood pressure. Furthermore, it has been suggested that ghrelin, which is believed to be secreted by endocrine cells in the stomach, may play a role in the etiology of type 2 diabetes (see, for example, Ghigo E et al., "Ghrelin: more than a natural GH secretagogue and/or an orexigenic factor," Clinical Endocrinology 62(1): 1-17 (January 2005; published online Nov. 17, 2004)). For some applications, the electrical signal described herein is configured to modulate (increase or decrease) ghrelin secretion by the stomach (e.g., by endocrine cells in the stomach).

The chronic improvement in blood glucose level is typically observable within three months of commencement of application of the stimulation, such as within 2-3 months, e.g., within one month or 3 weeks. As is well known in the art, HbAlc reflects long-term glucose levels over the preceding 6- to 12-week period.

As used in the present application, including in the claims, "improving" a blood glucose level means reducing a level of blood glucose (such as during fasting or eating), and/or reducing a rise in glucose level in response to eating. The improvement may persist on either on a long-term basis, or on a short-term basis (e.g., on an acute basis). For some applications, the improvement may occur as a result of short-term application of the signal (e.g., for less than 3 months, e.g., less than one week, or less than one hour). Alternatively or additionally, for some applications, the improvement may occur as a result of longer-term application of the signal, e.g., for at least one month, or chronic application of the signal, such as for at least 3 months.

In some applications of the present invention, a method is provided for treating a human patient, comprising applying an electrical signal (current and/or voltage) to at least one fundic site of the patient, and configuring one or more parameters of the electrical signal to improve a blood glucose level of the patient, such as normalize the level, in order to treat the patient. For some applications, the method further comprises identifying that the patient suffers from diabetes (type 2 or type 1, and which may include obesity), or metabolic syndrome (which may include obesity), and the electrical signal is applied in response to the identifying. Techniques for identifying that a patient suffers from diabetes (type 2 or type 1), metabolic syndrome, and/or obesity (i.e., diagnosing diabetes, metabolic syndrome, and/or obesity) are well known in the art, and thus are not described herein. Alternatively or additionally, the method further comprises identifying that the patient might benefit from an improved blood glucose level (e.g., because the patient suffers from poor blood glucose level control, for example, as indicated by a glucose tolerance test and/or elevated HbAlc). The electrical signal is applied in response to the identifying. Alternatively or additionally, the method further comprises identifying that the patient might experience an improvement in a blood glucose level in response to applying the signal, and applying the signal in response to the identifying. Further alternatively or additionally, the method further comprises identifying that application of the electrical signal to the at least one fundic site of the patient might chronically improve a blood glucose level of the patient, and applying the signal in response to the identifying.

For some applications, the electrical signal is configured to chronically improve the blood glucose level over a period of at least three months, such as by causing an improved response to eating, e.g., reduced postprandial glucose levels, and, consequently, a reduction in HbAlc of the patient. For some applications, one or more parameters of the electrical signal are configured to effect a reduction in HbAlc of at least 0.5 percentage points (i.e., from x % to (x-0.5) %, e.g., from 7.5% to 7%), such as at least 1 percentage point, or at least 1.5 percentage points.

Optionally, the method further comprises assessing blood glucose level control by measuring the level of HbAlc, either by the GI apparatus, another device in communication with the GI apparatus, and/or using conventional laboratory techniques. (Optionally, HbAlc is alternatively or additionally expressed as estimated Average Glucose (eAG), as recommended by the American Diabetes Association (ADA) and the American Association for Clinical Chemistry (AACC).) For some applications, blood glucose level improvement is assessed by measuring the blood glucose level.

For some applications, the stimulation techniques described herein are alternatively or additionally used to apply electrical stimulation to a non-gastric site of the gastrointestinal (GI) tract, such as the duodenum, intestine, colon, and/or esophagus.

In some embodiments of the present invention, gastrointestinal apparatus comprises a set of one or more electrodes which are applied to one or more sites of the gastrointestinal (GI) tract of a patient, such as the stomach. A control unit drives the electrode set to apply signals to the GI tract, and configures the signals pace peristaltic movement of material through the GI tract. The signals include a non-excitatory signal, such as an Excitable-Tissue Control (ETC) signal, and in addition, for some applications, an excitatory pacing signal. The pacing signal initiates contraction of the muscle of the GI tract by generating slow waves (propagating action potentials) in the muscle, while the non-excitatory signal modulates, e.g., increases, the contraction of the muscle, while not generating slow waves in the tissue. For some applications, the non-excitatory signal modulates contraction forces induced by the pacing signal, while for other applications, the non-excitatory signal modulates contraction forces occurring naturally in the GI tract.

For some applications, such stimulation is applied to the stomach, and configured to treat gastroparesis (e.g., diabetic, idiopathic, ischemic, or post-operative) by at least one of the following: increasing gastric emptying, better controlling the activation cycle, causing better electro-mechanical coupling, and causing better contraction force. In addition, such stimulation may alleviate symptoms of gastroparesis, such as nausea, dizziness, and vomiting. Such alleviation may be mediated by increased gastric emptying and/or by a neural pathway.

For some applications, such stimulation is applied to control gastric emptying and GI motility for improved metabolic treatment by affecting the time in which food is digested in the stomach, and affecting the timing in which food is forwarded for further processing and absorption in the duodenum and intestine. Such control may treat obesity and diabetes (either type 2 or type 1).

For some applications, such stimulation is applied to treat arrhythmia, diarrhea, or symptoms of irritable bowel syndrome. For example, the stimulation may be applied to nerve fibers, and/or to the intestine, either on demand, or continuously, or per a pre-defined schedule, or in response to detection of arrhythmic behavior.

For some applications, such stimulation is applied to treat symptoms of gastro-esophageal reflux disease (GERD) by stimulating the esophagus or the esophageal sphincter.

In the context of the present patent application and in the claims, the use of a non-excitatory signal to modify the response of one or more cells to electrical activation thereof, without inducing action potentials in the cells, is referred to as Excitable-Tissue Control (ETC).

Alternatively, the non-excitatory signal comprises the non-excitatory field described in the above-mentioned U.S. Pat. No. 6,947,792 to Ben-Haim et al., which is configurable to increase or decrease the force of muscle contraction. Further alternatively, the non-excitatory signal comprises a fencing signal, which fences the propagation of activity, such as described in the above-mentioned U.S. Pat. Nos. 6,415,178 and 7,218,963 to Ben-Haim et al. Such a reduction in activity may, for example, be used to treat arrhythmia, diarrhea, or irritable bowel syndrome.

There is therefore provided, in accordance with an application of the present invention, apparatus for treating a human patient, the apparatus including:

one or more electrode contact surfaces, which are configured to be applied to a fundus of the patient; and a control unit, configured to drive the one or more electrode contact surfaces to apply an electrical signal to the fundus that chronically improves a blood glucose level of the patient, in order to treat the patient, without calculating an impedance of tissue of the fundus based on a sensed parameter that varies in response to the electrical signal, for detecting eating by the patient or a characteristic of food eaten by the patient.

There is further provided, in accordance with an application of the present invention, apparatus for treating a human patient, the apparatus including:

a set of one or more implantable electrode contact surfaces, configured to be applied to a fundus of the patient; and a control unit, configured to:

during first and second modes of operation, drive the electrode contact surfaces to apply an electrical signal to the fundus that chronically improves a blood glucose level of the patient, in order to treat the patient, and during the first mode of operation, and not during the second mode of operation, sense a parameter that varies in response to the applied electrical signal, and calculate, based on the sensed parameter, an impedance of tissue of the fundus.

For some applications, the control unit is configured to operate in the second mode of operation for a greater total amount of time than in the first mode of operation.

There is still further provided, in accordance with an application of the present invention, apparatus for treating a human patient, the apparatus including:

a set of one or more implantable electrode contact surfaces, configured to be applied to a fundus of the patient; and a control unit, configured to:

drive the electrode contact surfaces to apply, during a plurality of signal application time periods, an electrical signal to the fundus that chronically improves a blood glucose level of the patient, in order to treat the patient, sense a parameter that varies in response to the applied electrical signal, and calculate, based on the sensed parameter, an impedance of tissue of the fundus, and withhold sensing the parameter for a duration of at least one second following at least a portion of the signal application time periods.

There is additionally provided, in accordance with an application of the present invention, apparatus for treating a human patient, the apparatus including:

a set of one or more implantable electrode contact surfaces, configured to be applied to a fundus of the patient; and a control unit, configured to:

drive the electrode contact surfaces to apply an electrical signal to the fundus that chronically improves a blood glucose level of the patient, in order to treat the patient, wherein the electrical signal includes a plurality of pulses, and during application of less than 50% of the pulses:

sense a parameter that varies in response to the applied electrical signal, and calculate, based on the sensed parameter, an impedance of tissue of the fundus.

For some applications, the control unit is configured to sense the parameter and calculate the impedance during application of less than 10% of the pulses, such as less than 2% of the pulses. For some of the applications described above, the control unit is configured to configure one or more parameters of the electrical signal responsively to the calculated impedance. For some applications, the control unit is configured to apply the electrical signal in a series of pulses, and to set a duration of the pulses at least in part responsively to the calculated impedance.

There is yet additionally provided, in accordance with an application of the present invention, apparatus for treating a human patient, the apparatus including:

a set of one or more implantable electrode contact surfaces, configured to be applied to a fundus of the patient; and a control unit, configured to:

during signal-application periods, drive the electrode contact surfaces to apply an electrical signal to the fundus that chronically improves a blood glucose level of the patient, in order to treat the patient, and provide reduced-signal-application periods, which alternate with the signal-application periods, and during which the electrode contact surfaces apply the electrical signal having an average energy that is less than 20% of the average energy of the electrical signal applied during the signal-application periods, wherein the control unit is configured to provide one or more reduced-signal-application periods during every 24-hour period, each of which reduced-signal-application periods has a duration of at least 30 minutes.

For some applications, the reduced-signal-application periods are non-signal-application periods, and the control unit is configured to withhold driving the electrode contact surfaces to apply the electrical signal during the non-signal-application periods. For some applications, the control unit is configured to drive the electrode contact surfaces, during the signal-application periods, to apply the electrical signal as a plurality of pulses alternating with inter-pulse gaps.

For some applications, the control unit is configured to set a duration of at least one of the signal-application periods every 24 hours to be at least 10 minutes. For some applications, the control unit is configured to provide the reduced-signal-application periods in accordance with a predetermined schedule. For some applications, the control unit is configured to sense eating by the patient, and to apply the electrical signal during the signal-application periods in response to the sensed eating. For some applications, the control unit is configured to sense eating by the patient, and to provide the reduced-signal-application periods in response to the sensed eating. For some applications, the control unit is configured to provide the signal-application periods only during a plurality of hours during nighttime. For some applications, the control unit is configured to provide the signal-application periods only during a plurality of hours during daytime.

There is also provided, in accordance with an application of the present invention, apparatus for treating a human patient, the apparatus including:

a set of one or more implantable electrode contact surfaces, configured to be applied to a fundus of the patient; and a control unit, configured to drive the electrode contact surfaces to apply an electrical signal to the fundus that chronically improves a blood glucose level of the patient, in order to treat the patient, without the control unit applying, or generating a signal for applying, any additional glucose-control or weight-control therapy to the patient.

For some applications, the apparatus does not include any electrode contact surfaces that are configured to be applied to an antrum of the patient.

There is further provided, in accordance with an application of the present invention, apparatus for treating a human patient, the apparatus including:
a set of one or more implantable electrode contact surfaces, configured to be applied to a fundus of the patient; and
a control unit, configured to drive the electrode contact surfaces to apply an electrical signal to the fundus that chronically improves a blood glucose level of the patient, in order to treat the patient, without calculating an impedance of tissue of the fundus based on a sensed parameter that varies in response to the electrical signal.

There is still further provided, in accordance with an application of the present invention, apparatus for treating a human patient, the apparatus including:
a set of one or more implantable electrode contact surfaces, at least a portion of which are configured to be applied to a fundus of the patient; and
a control unit, configured to drive (a) the one or more electrode contact surfaces using no more than 5 J over a 24-hour period, and (b) the portion of the electrode contact surfaces to apply an electrical signal to the fundus that chronically improves a blood glucose level of the patient, in order to treat the patient.

For some applications, the control unit is configured to drive the one or more electrode contact surfaces using no more than 2 J over the 24-hour period.

There is additionally provided, in accordance with an application of the present invention, apparatus for treating a human patient, the apparatus including:
a set of one or more implantable electrode contact surfaces, configured to be applied to a fundus of the patient; and
a control unit, configured to drive the electrode contact surfaces to apply an electrical signal to the fundus that chronically improves a blood glucose level of the patient, in order to treat the patient,
wherein the control unit is sized such that at least one line that passes from edge to edge of the control unit through a center of gravity thereof has a length of no more than 2 cm.

For example, the length may be no more than 1 cm.

For any of the applications described above, the apparatus may include exactly one electrode structure that includes the one or more electrical contact surfaces. For some applications, the electrode contact surfaces include exactly one electrode contact surface. Alternatively, for some applications, the electrode contact surfaces include exactly two electrode contact surfaces. For some applications, the electrode structure further includes one or more insulated cables. For some applications, the apparatus includes exactly one connector, which connects one or more of the insulated cables to the control unit. For some applications, the one or more insulated cables include exactly one bifurcated insulated cable, having exactly two bifurcated ends and exactly one non-bifurcated end, each of the electrode contact surfaces are coupled to one of the bifurcated ends, and the non-bifurcated end is coupled to the control unit. For some applications, the exactly one of the insulated cables includes a plurality of insulated wires. For some applications, the one or more insulated cables include exactly one multifurcated insulated cable, having at least three multifurcated ends and exactly one non-multifurcated end, each of the electrode contact surfaces are coupled to one of the multifurcated ends, and the non-multifurcated end is coupled to the control unit. For some applications, the exactly one of the insulated cables includes a plurality of insulated wires. For some applications, one end of exactly one of the insulated cables is coupled to the control unit. For some applications, the exactly one of the insulated cables includes a plurality of insulated wires.

For some applications, the electrode structure includes a corkscrew-shaped electrode mount, which is configured to be implanted in a wall of the fundus, and which includes the one or more electrode contact surfaces, at respective sites of the electrode mount. For some applications, the electrode structure includes one or more wireless microstimulators. For some applications, the electrode structure includes exactly one wireless microstimulator. For some applications, the electrode structure is at least partially flexible.

For some applications, the one or more electrode contact surfaces include a plurality of electrode contact surfaces, and the electrode structure is configured to constrain motion of the electrode contact surfaces so as to define a greatest possible distance between closest respective portions of any two of the electrode contact surfaces, which distance is no more than 10 cm.

For any of the applications described above, the control unit may be configured to configure the electrical signal such that the signal, if applied to an antrum of the patient, would not effect an improvement in a blood glucose level of the patient. For any of the applications described above, the apparatus may be configured to be implantable in the patient for long-term application of the electrical signal. For any of the applications described above, the electrode contact surfaces may be configured to be applied in physical contact with muscle tissue of the fundus. For some applications, the electrode contact surfaces are configured to be positioned within the muscle tissue. For any of the applications described above, the apparatus may be configured to treat diabetes of the patient, such as type 2 diabetes of the patient. For any of the applications described above, the apparatus may be configured to treat metabolic syndrome of the patient. For any of the applications described above, the control unit may be configured to configure one or more parameters of the electrical signal to cause a reduction in a fasting glucose blood level of the patient. For any of the applications described above, the control unit may be configured to configure one or more parameters of the electrical signal to cause a reduction in postprandial glucose level of the patient.

For any of the applications described above, the control unit may be configured to configure one or more parameters of the electrical signal to cause an improvement in a level at least one hormone selected from the group consisting of: at least one hormone associated with glycemic control, and at least one hormone associated with a metabolic disorder. For some applications, the improvement in the level of the at least one hormone includes a normalization of at least one element selected from the group consisting of: secretion of the at least one hormone, expression of the at least one hormone, and a blood level of the at least one hormone. For some applications, the hormone is associated with the glycemic control. For some applications, the hormone is associated with the metabolic disorder. For some applications, the control unit is configured to configure the one or more parameters of the electrical signal to simultaneously cause the improvement in levels of a plurality of hormones. For some applications, the at least one hormone is secreted by a stomach of the patient, such as by the fundus, or by an antrum of the stomach. For some applications, the at least one hormone is secreted by a duodenum of the patient. For some applications, the at least one hormone is secreted by a pancreas of the patient.

For some applications, the improvement is an improvement in a postprandial level of the at least one hormone.

Alternatively or additionally, the improvement is an improvement in a fasting level of the at least one hormone.

For some applications, the improvement includes an improvement (e.g., an increase) in a postprandial level of insulin. For some applications, the improvement includes an improvement (e.g., a decrease) in a postprandial level of ghrelin. For some applications, the improvement includes an improvement (e.g., a decrease) in a fasting level of ghrelin. For some applications, the improvement includes an improvement (e.g., a decrease) in a postprandial level of glucagon. For some applications, the improvement includes an improvement (e.g., an increase) in a postprandial level of pancreatic polypeptide. For some applications, the improvement includes an improvement (e.g., an increase) in a fasting level of pancreatic polypeptide. For some applications, the improvement includes an improvement (e.g., an increase) in a postprandial level of glucagon-like peptide-1 (GLP-1).

For any of the applications described above, the control unit may be configured to configure one or more parameters of the electrical signal to cause an improvement (e.g., an increase) in a postprandial level of C-peptide.

For any of the applications described above, the control unit may be configured to configure one or more parameters of the electrical signal to not cause hypoglycemia of the patient. For some applications, the control unit is configured to configure the one or more parameters of the signal to not cause the hypoglycemia, without measuring the blood glucose level of the patient.

For any of the applications described above, the control unit may be configured to apply the signal in a series of pulses having an energy per pulse of no more than 5 microjoules. For any of the applications described above, the control unit may be configured to apply the signal in a series of pulses having an average energy per pulse of no more than 5 microjoules. For any of the applications described above, the control unit may be configured to apply the signal having an instantaneous power of no more than 100 milliwatts. For any of the applications described above, the control unit may be configured to apply the signal in a series of pulses, at least one of which pulses has a duration of between 2 microseconds and 5 milliseconds. For any of the applications described above, the control unit may be configured to apply the signal in a series of pulses, at least one of which pulses has an amplitude of between 5 mA and 35 mA.

There is yet additionally provided, in accordance with an application of the present invention, a method for treating a human patient, including:
implanting one or more electrode contact surfaces in contact with a fundus of the patient;
providing a control unit coupled to the electrode contact surfaces; and
activating the control unit to drive the electrode contact surfaces to apply an electrical signal to at least one fundic site of the patient that chronically improves a blood glucose level of the patient, in order to treat the patient, without calculating an impedance of tissue of the fundus based on a sensed parameter that varies in response to the electrical signal, for sensing eating by the patient or a characteristic of food eaten by the patient.

For some applications, activating includes configuring the control unit to apply the signal to the at least one fundic site at least intermittently during a period having a duration of at least one week, without applying any electrical signals to any antral sites of the patient during the period.

There is also provided, in accordance with an application of the present invention, a method for treating a human patient, including:

endoscopically making one or more incisions through a fundic wall of the patient;
via exactly one of the one or more incisions, implanting one or more electrode contact surfaces in contact with a fundus of the patient;
providing a control unit coupled to the electrode contact surfaces; and
activating the control unit to drive the electrode contact surfaces to apply an electrical signal to at least one fundic site of the patient that chronically improves a blood glucose level of the patient, in order to treat the patient.

For some applications, providing the control unit includes implanting the control unit in a body of the patient via the exactly one of the one or more incisions. For some applications, providing the control unit includes providing the control unit sized such that at least one line that passes from edge to edge of the control unit through the center of gravity thereof has a length of no more than 2 cm, such as no more than 1 cm. For some applications, making the one or more incisions and implanting include making the one or more incisions and implanting during a surgical implantation procedure having a duration of no more than 45 minutes.

There is further provided, in accordance with an application of the present invention, a method for treating a human patient, including:
identifying that application of an electrical signal to at least one fundic site of the patient might chronically improve a blood glucose level of the patient; and
in response to identifying:
  implanting one or more electrode contact surfaces in contact with a fundus of the patient;
  providing a control unit coupled to the electrode contact surfaces; and
  activating the control unit to drive the electrode contact surfaces to apply the electrical signal to the at least one fundic site of the patient that chronically improves the blood glucose level of the patient, in order to treat the patient.

There is still further provided, in accordance with an application of the present invention, a method for treating a human patient, including:
identifying that the patient might experience a chronic improvement in a blood glucose level in response to application of an electrical signal to at least one fundic site of the patient;
in response to identifying:
  implanting one or more electrode contact surfaces in contact with a fundus of the patient;
  providing a control unit coupled to the electrode contact surfaces; and
  activating the control unit to drive the electrode contact surfaces to apply the electrical signal to the at least one fundic site of the patient that chronically improves the blood glucose level of the patient, in order to treat the patient.

There is additionally provided, in accordance with an application of the present invention, a method for treating a human patient, including:
implanting one or more electrode contact surfaces in contact with a fundus of the patient;
providing a control unit coupled to the electrode contact surfaces; and
activating the control unit to:
during first and second modes of operation, drive the electrode contact surfaces to apply an electrical signal to at least one fundic site of the patient, and configuring one or more parameters of the electrical signal to chronically improve a blood glucose level of the patient, in order to treat the patient, and during the first mode, and not during the second mode, sense a parameter that varies in response to the applied electrical signal, and calculate, based on the sensed parameter, an impedance of tissue of the fundus.

There is yet additionally provided, in accordance with an application of the present invention, a method for treating a human patient, including:

implanting one or more electrode contact surfaces in contact with a fundus of the patient;

providing a control unit coupled to the electrode contact surfaces; and activating the control unit to:

drive the electrode contact surfaces to apply, during a plurality of signal application time periods, an electrical signal to at least one fundic site of the patient that chronically improves a blood glucose level of the patient, in order to treat the patient, sense a parameter that varies in response to the applied electrical signal, and calculate, based on the sensed parameter, an impedance of tissue of the fundus, and withhold sensing the parameter for a duration of at least one second following at least a portion of the signal application time periods.

There is also provided, in accordance with an application of the present invention, a method for treating a human patient, including:

implanting one or more electrode contact surfaces in contact with a fundus of the patient;

providing a control unit coupled to the electrode contact surfaces; and activating the control unit to:

drive the electrode contact surfaces to apply an electrical signal to at least one fundic site of the patient, which electrical signal includes a plurality of pulses, and configure one or more parameters of the electrical signal to chronically improve a blood glucose level of the patient, in order to treat the patient, and during application of less than 50% of the pulses, sense a parameter that varies in response to the applied electrical signal, and calculate, based on the sensed parameter, an impedance of tissue of the fundus.

For some applications, activating includes configuring the control unit to sense the parameter and calculate during application of less than 10% of the pulses, such as less than 2% of the pulses.

For some applications, activating includes configuring the control unit to configure the one or more parameters of the electrical signal responsively to the calculated impedance. For some applications, activating includes configuring the control unit to apply the electrical signal in a series of pulses, and to set a duration of the pulses at least in part responsively to the calculated impedance.

There is further provided, in accordance with an application of the present invention, a method for treating a human patient, including:

implanting one or more electrode contact surfaces in contact with a fundus of the patient;

providing a control unit coupled to the electrode contact surfaces; and activating the control unit to:

during signal-application periods, drive the electrode contact surfaces to apply an electrical signal to at least one fundic site of the patient that chronically improves a blood glucose level of the patient, in order to treat the patient, and provide reduced-signal-application periods, which alternate with the signal-application periods, and during which the electrode contact surfaces apply the electrical signal having an average energy current that is less than 20% of the average energy of the electrical signal applied during the signal-application periods, wherein the control unit provides one or more reduced-signal-applications periods during every 24-hour period, each of which reduced-signal-application periods has a duration of at least 30 minutes.

For some applications, the reduced-signal-application periods are non-signal-application periods, and wherein activating includes configuring the control unit to withhold applying the electrical signal during the non-signal-application periods. For some applications, activating includes configuring the control unit to apply the electrical signal as a plurality of pulses alternating with inter-pulse gaps. For some applications, activating includes configuring the control unit to set a duration of at least one of the signal-application periods every 24 hours to be at least 10 minutes. For some applications, activating includes configuring the control unit to provide the reduced-signal-application periods in accordance with a predetermined schedule. For some applications, activating includes configuring the control unit to sense eating by the patient, and to apply the electrical signal in response to the sensed eating. For some applications, activating includes configuring the control unit to sense eating by the patient, and to provide the reduced-signal-application periods in response to the sensed eating. For some applications, activating includes configuring the control unit to provide the signal-application periods only during a plurality of hours during nighttime. For some applications, activating includes configuring the control unit to provide the signal-application periods only during a plurality of hours during daytime.

There is still further provided, in accordance with an application of the present invention, a method for treating a human patient, including:

implanting one or more electrode contact surfaces in contact with a fundus of the patient;

providing a control unit coupled to the electrode contact surfaces; and activating the control unit to drive the electrode contact surfaces to apply an electrical signal to at least one fundic site of the patient that chronically improves a blood glucose level of the patient, in order to treat the patient, without the control unit applying, or generating a signal for applying, any additional glucose-control or weight-control therapy to the patient.

For some applications, the method does not include activating the control unit to apply any electrical signals to an antrum of the patient.

There is additionally provided, in accordance with an application of the present invention, a method for treating a human patient, including:

implanting one or more electrode contact surfaces in contact with a fundus of the patient;

providing a control unit coupled to the electrode contact surfaces; and activating the control unit to:

drive the electrode contact surfaces to apply an electrical signal to at least one fundic site of the patient, without calculating an impedance of tissue of the fundus based on a sensed parameter that varies in response to the electrical signal, and configure one or more parameters of the electrical signal to chronically improve a blood glucose level of the patient, in order to treat the patient.

There is yet additionally provided, in accordance with an application of the present invention, a method for treating a human patient, including:

implanting one or more electrode contact surfaces such that at least a portion of the electrode contact surfaces are in contact with a fundus of the patient;

providing a control unit coupled to the electrode contact surfaces; and activating the control unit to drive (a) the one or more electrode contact surfaces using no more than 5 J over a 24-hour period, and (b) the portion of the electrode contact surfaces to apply an electrical signal to the fundus that chronically improves a blood glucose level of the patient, in order to treat the patient.

For some applications, activating includes activating the control unit to drive the one or more electrode contact surfaces using no more than 2 J over the 24-hour period. For any of the applications described above, implanting the one or more electrode contact surfaces may include implanting exactly one implantable electrode structure that includes the one or more electrode contact surfaces. For any of the applications described above, activating may include configuring the control unit to configure the electrical signal such that the signal, if applied to an antrum of the patient, would not effect an improvement in a blood glucose level of the patient. For any of the applications described above, implanting the one or more electrode contact surfaces may include implanting the one or more electrode contact surfaces in physical contact with muscle tissue of the fundic site. For any of the applications described above, implanting the one more electrode contact surfaces may include positioning the one or more electrode contact surfaces within the muscle tissue.

For any of the applications described above, implanting the electrode contact surfaces and activating the control unit may include identifying that the patient suffers from diabetes, such as type 2 diabetes, and implanting and activating in response to the identifying. For any of the applications described above, implanting the electrode contact surfaces and activating the control unit may include identifying that the patient suffers from metabolic syndrome, and implanting and activating in response to the identifying.

For any of the applications described above, implanting the electrode contact surfaces and activating the control unit may include identifying that the patient might benefit from improved blood glucose level control, and implanting and activating in response to the identifying. For any of the applications described above, implanting the electrode contact surfaces and activating the control unit may include identifying that the patient might experience an improvement in the blood glucose level in response to applying the signal, and implanting and activating in response to identifying.

For any of the applications described above, activating may include configuring one or more parameters of the electrical signal to cause a reduction in a fasting glucose blood level of the patient. For any of the applications described above, activating may include configuring one or more parameters of the electrical signal to cause a reduction in postprandial glucose level of the patient.

For any of the applications described above, activating may include configuring one or more parameters of the electrical signal to cause an improvement in a level at least one hormone selected from the group consisting of: at least one hormone associated with glycemic control, and at least one hormone associated with a metabolic disorder. For some applications, the method further includes assessing the level of the at least one hormone after activating the control unit. For some applications, the improvement in the level of the at least one hormone includes a normalization of at least one element selected from the group consisting of: secretion of the at least one hormone, expression of the at least one hormone, and a blood level of the at least one hormone. For some applications, the hormone is associated with the glycemic control. Alternatively or additionally, the hormone is associated with the metabolic disorder. For some applications, configuring includes configuring the one or more parameters of the electrical signal to simultaneously cause the improvement in levels of a plurality of hormones. For some applications, the at least one hormone is secreted by a stomach of the patient. For some applications, the at least one hormone is secreted by the fundus. For some applications, the at least one hormone is secreted by an antrum of the stomach. For some applications, the at least one hormone is secreted by a duodenum of the patient. For some applications, the at least one hormone is secreted by a pancreas of the patient.

For some applications, the improvement includes an improvement (e.g., an increase) in a postprandial level of insulin. For some applications, the improvement includes an improvement (e.g., a decrease) in a postprandial level of ghrelin. For some applications, the improvement includes an improvement (e.g., a decrease) in a fasting level of ghrelin. For some applications, the improvement includes an improvement (e.g., a decrease) in a postprandial level of glucagon. For some applications, the improvement includes an improvement (e.g., an increase) in a postprandial level of pancreatic polypeptide. For some applications, the improvement includes an improvement (e.g., an increase) in a fasting level of pancreatic polypeptide. For some applications, the improvement includes an improvement (e.g., an increase) in a postprandial level of glucagon-like peptide-1 (GLP-1).

For any of the applications described above, activating may include configuring one or more parameters of the electrical signal to cause an improvement (e.g., an increase) in a postprandial level of C-peptide. For some applications, the method further includes assessing the level of C-peptide after activating the control unit.

For any of the applications described above, implanting the electrode contact surfaces and activating the control unit may include identifying that the patient might experience an improvement in a level at least one hormone in response to applying the signal, and implanting and activating in response to identifying, and the at least one hormone is selected from the group consisting of: at least one hormone associated with glycemic control, and at least one hormone associated with a metabolic disorder. For some applications, the improvement in the level of the at least one hormone includes a normalization of at least one element selected from the group consisting of: secretion of the at least one hormone, expression of the at least one hormone, and a blood level of the at least one hormone. For some applications, the at least one hormone is associated with the glycemic control. Alternatively or additionally, the at least one hormone is associated with the metabolic disorder. For some applications, the improvement is a simultaneous improvement in levels of a plurality of hormones. For some applications, the at least one hormone is secreted by a stomach of the patient. For some applications, the at least one hormone is secreted by the fundus. For some applications, the at least one hormone is secreted by an antrum of the stomach. For some applications, the at least one hormone is secreted by a duodenum of the patient. For some applications, the at least one hormone is secreted by a pancreas of the patient.

For some applications, the improvement includes an improvement (e.g., an increase) in a postprandial level of insulin. For some applications, the improvement includes an improvement (e.g., a decrease) in a postprandial level of ghrelin. For some applications, the improvement includes an improvement (e.g., a decrease) in a fasting level of ghrelin. For some applications, the improvement includes an improvement (e.g., a decrease) in a postprandial level of glucagon. For some applications, the improvement includes an improvement (e.g., an increase) in a postprandial level of pancreatic polypeptide. For some applications, the improvement includes an improvement (e.g., an increase) in a fasting level of pancreatic polypeptide. For some applications, the improvement includes an improvement (e.g., an increase) in a postprandial level of glucagon-like peptide-1 (GLP-1).

For any of the applications described above, implanting the electrode contact surfaces and activating the control unit may include identifying that the patient might experience an improvement (e.g., an increase) in a postprandial level of C-peptide in response to applying the signal, and implanting and activating in response to identifying.

For any of the applications described above, the method may further include assessing blood glucose level control by measuring a level of HbA1c of the patient after activating the control unit. For any of the applications described above, the method may further include assessing blood glucose level improvement by measuring the blood glucose level after activating the control unit.

For any of the applications described above, activating may include configuring one or more parameters of the electrical signal to not cause hypoglycemia of the patient. For some applications, configuring the one or more parameters of the electrical signal to not cause the hypoglycemia does not include measuring the blood glucose level of the patient.

For any of the applications described above, activating may include configuring the control unit to apply the signal in a series of pulses having an energy per pulse of no more than 5 microjoules. For any of the applications described above, activating may include configuring the control unit to apply the signal in a series of pulses having an average energy per pulse of no more than 5 microjoules. For any of the applications described above, activating may include configuring the control unit to apply the signal having an instantaneous power of no more than 100 milliwatts. For any of the applications described above, activating may include configuring the control unit to apply the signal in a series of pulses, at least one of which pulses has a duration of between 2 microseconds and 5 milliseconds. For any of the applications described above, activating may include configuring the control unit to apply the signal in a series of pulses, at least one of which pulses has an amplitude of between 5 mA and 35 mA. For any of the applications described above, the activating may include configuring the control unit to apply the signal for at least three months.

There is also provided, in accordance with an application of the present invention, apparatus for treating a human patient, the apparatus including:
one or more electrode contact surfaces, which are configured to be applied to a fundus of the patient; and
a control unit, configured to drive the electrode contact surfaces to apply an electrical signal to the fundus that improves a blood glucose level of the patient, in order to treat the patient, without calculating an impedance of tissue of the fundus based on a sensed parameter that varies in response to the electrical signal, for detecting eating by the patient or a characteristic of food eaten by the patient.

There is further provided, in accordance with an application of the present invention, apparatus for treating a human patient, the apparatus including:
a set of one or more implantable electrode contact surfaces, configured to be applied to a fundus of the patient; and
a control unit, configured to:
during first and second modes of operation, drive the electrode contact surfaces to apply an electrical signal to the fundus that improves a blood glucose level of the patient, in order to treat the patient, and
during the first mode of operation, and not during the second mode of operation, sense a parameter that varies in response to the applied electrical signal, and calculate, based on the sensed parameter, an impedance of tissue of the fundus.

There is still further provided, in accordance with an application of the present invention, apparatus for treating a human patient, the apparatus including:
a set of one or more implantable electrode contact surfaces, configured to be applied to a fundus of the patient; and
a control unit, configured to:
drive the electrode contact surfaces to apply, during a plurality of signal application time periods, an electrical signal to the fundus that improves a blood glucose level of the patient, in order to treat the patient,
sense a parameter that varies in response to the applied electrical signal, and calculate, based on the sensed parameter, an impedance of tissue of the fundus, and
withhold sensing the parameter for a duration of at least one second following at least a portion of the signal application time periods.

There is additionally provided, in accordance with an application of the present invention, apparatus for treating a human patient, the apparatus including:
a set of one or more implantable electrode contact surfaces, configured to be applied to a fundus of the patient; and
a control unit, configured to:
drive the electrode contact surfaces to apply an electrical signal to the fundus that improves a blood glucose level of the patient, in order to treat the patient, wherein the electrical signal includes a plurality of pulses, and
during application of less than 50% of the pulses:
sense a parameter that varies in response to the applied electrical signal, and
calculate, based on the sensed parameter, an impedance of tissue of the fundus.

There is yet additionally provided, in accordance with an application of the present invention, apparatus for treating a human patient, the apparatus including:
a set of one or more implantable electrode contact surfaces, configured to be applied to a fundus of the patient; and
a control unit, configured to:
during signal-application periods, drive the electrode contact surfaces to apply an electrical signal to the fundus that improves a blood glucose level of the patient, in order to treat the patient, and
provide reduced-signal-application periods, which alternate with the signal-application periods, and during which the electrode contact surfaces apply the electrical signal having an average energy that is less than 20% of the average energy of the electrical signal applied during the signal-application periods,
wherein the control unit is configured to provide one or more reduced-signal-application periods during every 24-hour period, each of which reduced-signal-application periods has a duration of at least 30 minutes.

There is also provided, in accordance with an application of the present invention, apparatus for treating a human patient, the apparatus including:
- a set of one or more implantable electrode contact surfaces, configured to be applied to a fundus of the patient; and
- a control unit, configured to drive the electrode contact surfaces to apply an electrical signal to the fundus that improves a blood glucose level of the patient, in order to treat the patient, without the control unit applying, or generating a signal for applying, any additional glucose-control or weight-control therapy to the patient.

There is further provided, in accordance with an application of the present invention, apparatus for treating a human patient, the apparatus including:
- a set of one or more implantable electrode contact surfaces, configured to be applied to a fundus of the patient; and
- a control unit, configured to drive the electrode contact surfaces to apply an electrical signal to the fundus that improves a blood glucose level of the patient, in order to treat the patient, without calculating an impedance of tissue of the fundus based on a sensed parameter that varies in response to the electrical signal.

There is still further provided, in accordance with an application of the present invention, apparatus for treating a human patient, the apparatus including:
- a set of one or more implantable electrode contact surfaces, at least a portion of which are configured to be applied to a fundus of the patient; and
- a control unit, configured to drive (a) the one or more electrode contact surfaces using no more than 5 J over a 24-hour period, and (b) the portion of the electrode contact surfaces to apply an electrical signal to the fundus that improves a blood glucose level of the patient, in order to treat the patient.

There is additionally provided, in accordance with an application of the present invention, apparatus for treating a human patient, the apparatus including:
- a set of one or more implantable electrode contact surfaces, configured to be applied to a fundus of the patient; and
- a control unit, configured to drive the electrode contact surfaces to apply an electrical signal to the fundus that improves a blood glucose level of the patient, in order to treat the patient,
- wherein the control unit is sized such that at least one line that passes from edge to edge of the control unit through a center of gravity thereof has a length of no more than 2 cm.

There is yet additionally provided, in accordance with an application of the present invention, a method for treating a human patient, including:
- implanting one or more electrode contact surfaces in contact with a fundus of the patient;
- providing a control unit coupled to the electrode contact surfaces; and
- activating the control unit to drive the electrode contact surfaces to apply an electrical signal to at least one fundic site of the patient that improves a blood glucose level of the patient, in order to treat the patient, without calculating an impedance of tissue of the fundus based on a sensed parameter that varies in response to the electrical signal, for sensing eating by the patient or a characteristic of food eaten by the patient.

There is also provided, in accordance with an application of the present invention, a method for treating a human patient, including:
- endoscopically making one or more incisions through a fundic wall of the patient;
- via exactly one of the one or more incisions, implanting one or more electrode contact surfaces in contact with a fundus of the patient;
- providing a control unit coupled to the electrode contact surfaces; and
- activating the control unit to drive the electrode contact surfaces to apply an electrical signal to at least one fundic site of the patient that improves a blood glucose level of the patient, in order to treat the patient.

There is further provided, in accordance with an application of the present invention, a method for treating a human patient, including:
- identifying that application of an electrical signal to at least one fundic site of the patient might improve a blood glucose level of the patient; and
- in response to identifying:
  - implanting one or more electrode contact surfaces in contact with a fundus of the patient;
  - providing a control unit coupled to the electrode contact surfaces; and
  - activating the control unit to drive the electrode contact surfaces to apply the electrical signal to the at least one fundic site of the patient that improves the blood glucose level of the patient, in order to treat the patient.

There is still further provided, in accordance with an application of the present invention, a method for treating a human patient, including:
- identifying that the patient might experience a chronic improvement in a blood glucose level in response to application of an electrical signal to at least one fundic site of the patient;
- in response to identifying:
  - implanting one or more electrode contact surfaces in contact with a fundus of the patient;
  - providing a control unit coupled to the electrode contact surfaces; and
  - activating the control unit to drive the electrode contact surfaces to apply the electrical signal to the at least one fundic site of the patient that improves the blood glucose level of the patient, in order to treat the patient.

There is additionally provided, in accordance with an application of the present invention, a method for treating a human patient, including:
- implanting one or more electrode contact surfaces in contact with a fundus of the patient;
- providing a control unit coupled to the electrode contact surfaces; and
- activating the control unit to:
  - during first and second modes of operation, drive the electrode contact surfaces to apply an electrical signal to at least one fundic site of the patient, and configuring one or more parameters of the electrical signal to improve a blood glucose level of the patient, in order to treat the patient, and
  - during the first mode, and not during the second mode, sense a parameter that varies in response to the applied electrical signal, and calculate, based on the sensed parameter, an impedance of tissue of the fundus.

There is yet additionally provided, in accordance with an application of the present invention, a method for treating a human patient, including:

implanting one or more electrode contact surfaces in contact with a fundus of the patient;

providing a control unit coupled to the electrode contact surfaces; and activating the control unit to:

drive the electrode contact surfaces to apply, during a plurality of signal application time periods, an electrical signal to at least one fundic site of the patient that improves a blood glucose level of the patient, in order to treat the patient, sense a parameter that varies in response to the applied electrical signal, and calculate, based on the sensed parameter, an impedance of tissue of the fundus, and withhold sensing the parameter for a duration of at least one second following at least a portion of the signal application time periods.

There is also provided, in accordance with an application of the present invention, a method for treating a human patient, including:

implanting one or more electrode contact surfaces in contact with a fundus of the patient;

providing a control unit coupled to the electrode contact surfaces; and activating the control unit to:

drive the electrode contact surfaces to apply an electrical signal to at least one fundic site of the patient, which electrical signal includes a plurality of pulses, and configure one or more parameters of the electrical signal to improve a blood glucose level of the patient, in order to treat the patient, and during application of less than 50% of the pulses, sense a parameter that varies in response to the applied electrical signal, and calculate, based on the sensed parameter, an impedance of tissue of the fundus.

There is further provided, in accordance with an application of the present invention, a method for treating a human patient, including:

implanting one or more electrode contact surfaces in contact with a fundus of the patient;

providing a control unit coupled to the electrode contact surfaces; and activating the control unit to:

during signal-application periods, drive the electrode contact surfaces to apply an electrical signal to at least one fundic site of the patient that improves a blood glucose level of the patient, in order to treat the patient, and provide reduced-signal-application periods, which alternate with the signal-application periods, and during which the electrode contact surfaces apply the electrical signal having an average energy that is less than 20% of the current of the electrical signal applied during the signal-application periods, wherein the control unit provides one or more reduced-signal-application periods during every 24-hour period, each of which reduced-signal-application periods has a duration of at least 30 minutes.

There is still further provided, in accordance with an application of the present invention, a method for treating a human patient, including:

implanting one or more electrode contact surfaces in contact with a fundus of the patient;

providing a control unit coupled to the electrode contact surfaces; and activating the control unit to drive the electrode contact surfaces to apply an electrical signal to at least one fundic site of the patient that improves a blood glucose level of the patient, in order to treat the patient, without the control unit applying, or generating a signal for applying, any additional glucose-control or weight-control therapy to the patient.

There is additionally provided, in accordance with an application of the present invention, a method for treating a human patient, including:

implanting one or more electrode contact surfaces in contact with a fundus of the patient;

providing a control unit coupled to the electrode contact surfaces; and activating the control unit to:

drive the electrode contact surfaces to apply an electrical signal to at least one fundic site of the patient, without calculating an impedance of tissue of the fundus based on a sensed parameter that varies in response to the electrical signal, and configure one or more parameters of the electrical signal to improve a blood glucose level of the patient, in order to treat the patient.

There is yet additionally provided, in accordance with an application of the present invention, a method for treating a human patient, including:

implanting one or more electrode contact surfaces such that at least a portion of the electrode contact surfaces are in contact with a fundus of the patient;

providing a control unit coupled to the electrode contact surfaces; and activating the control unit to drive (a) the one or more electrode contact surfaces using no more than 5 J over a 24-hour period, and (b) the portion of the electrode contact surfaces to apply an electrical signal to the fundus that improves a blood glucose level of the patient, in order to treat the patient.

There is also provided, in accordance with an application of the present invention, a method including:

applying a pacing signal at a first site of a gastrointestinal (GI) tract of a patient; and applying a non-excitatory signal at a second site of the GI tract, which second site is at least 5 cm distal to the first site.

For some applications, applying the non-excitatory signal includes applying an excitable tissue control (ETC) signal. For some applications, the method further includes identifying that the patient suffers from gastroparesis, and treating the gastroparesis by applying the signals. Alternatively or additionally, the method further includes identifying that the patient suffers from obesity, and treating the obesity by applying the signals. Alternatively or additionally, the method further includes identifying that the patient suffers from a metabolic disorder, and treating the metabolic disorder by applying the signals. For some applications, the first and second sites are on a stomach of the patient. For example, the first site may be on a corpus of the stomach, and the second site may be on an antrum of the stomach. For some applications, the method further includes applying a pacing signal at the second site.

For some applications, applying the non-excitatory signal includes applying the non-excitatory signal at the second site without applying a pacing signal at the second site. For some applications, applying the non-excitatory signal at the second site including sensing an electrical parameter of the GI tract at the second site, and applying the non-excitatory signal responsively to the sensed parameter. For some applications, applying the non-excitatory signal at the second site includes applying the non-excitatory signal at the second site after a predetermined delay after applying the pacing signal at the first site.

For some applications, applying the pacing signal and the non-excitatory signal includes applying the pacing signal and non-excitatory signals at a plurality of sites simultaneously.

For some applications, the method further includes applying a neural modulation signal. For some applications, applying at least one of the pacing signal, the non-excitatory signal, and the neural modulation signal includes adapting the applying in accordance with at least one of an external input by the patient, a predefined schedule, and a determination that eating has occurred.

There is further provided, in accordance with an application of the present invention, apparatus for application to a gastrointestinal (GI) tract of a patient, the apparatus including:

a first set of one or more electrodes, configured to be applied to a first site of the GI tract;

a second set of one or more electrodes, configured to be applied to a second site of the GI tract, which second site is at least 5 cm distal to the first site; and a control unit, configured to drive the first electrode set to apply a pacing signal at the first site, and to drive the second electrode set to apply a non-excitatory signal at the second site.

For some applications, the non-excitatory signal is an excitable tissue control (ETC) signal, and the control unit is configured to drive the second electrode set to apply the ETC signal. For some applications, the first and second sites are on a stomach of the patient. For some applications, the first site is on a corpus of the stomach, and the second site is on an antrum of the stomach. For some applications, the control unit is configured to apply a pacing signal at the second site. For some applications, the control unit is configured to apply the non-excitatory signal at the second site without applying a pacing signal at the second site. For some applications, the control unit is configured to sense an electrical parameter of the GI tract at the second site, and to drive the second electrode set to apply the non-excitatory signal responsively to the sensed parameter. For some applications, the control unit is configured to drive the second electrode set to apply the non-excitatory signal at the second site after a predetermined delay after applying the pacing signal at the first site. For some applications, the control unit is configured to drive the first and second electrode sets to apply the pacing and non-excitatory signals, respectively, at a plurality of sites simultaneously. For some applications, the control unit is configured to further apply a neural modulation signal. For some applications, the control unit is configured to apply at least one of the pacing signal, the non-excitatory signal, and the neural modulation signal by adapting the applying in accordance with at least one of an external input by the patient, a predefined schedule, and a determination that eating has occurred.

The present invention will be more fully understood from the following detailed description of embodiments thereof, taken together with the drawings, in which:

BRIEF DESCRIPTION OF THE DRAWINGS

FIGS. 13A-B are graphs showing experimental results measured in accordance with an application of the present invention.

DETAILED DESCRIPTION OF APPLICATIONS

Figure 1:
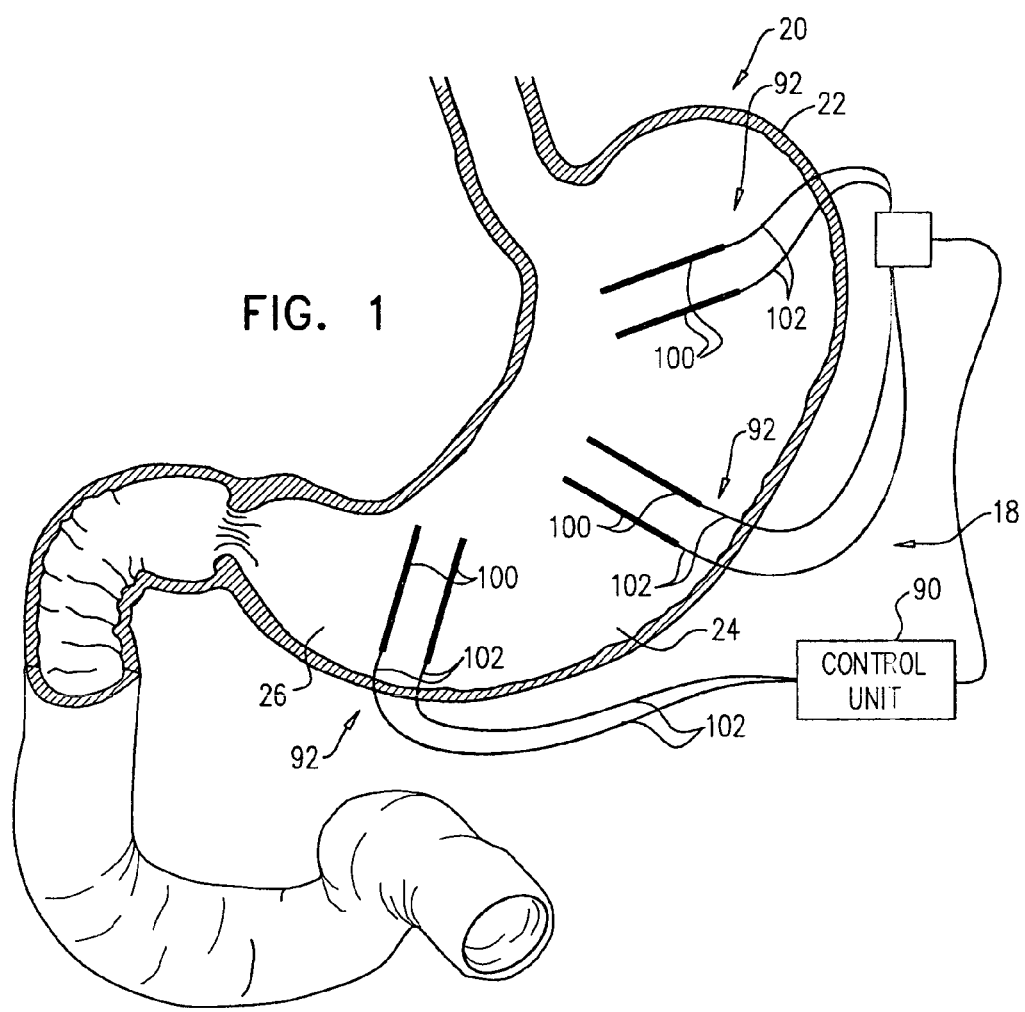
FIG. 1 is a schematic illustration of gastrointestinal apparatus, in accordance with an application of the present invention.

FIG. 1 is a schematic illustration of gastrointestinal (GI) apparatus 18, in accordance with some applications of the present invention. For some applications, apparatus 18 applies electrical stimulation to a stomach 20 of a patient, such as a fundus 22 of the patient. For some applications, apparatus 18 comprises an implantable or external control unit 90, and one or more electrode structures 92, which comprises one or more implantable electrode contact surfaces 100 coupled to control unit 90 by respective leads 102. Leads 102 typically comprises one or more insulated cables, which may comprise a plurality of insulated wires (e.g., twisted insulated wires). Control unit 90 typically comprises a power source, such as one or more rechargeable or non-rechargeable batteries.

Alternatively, the electrode structures 92 comprise one or more implantable wireless microstimulators, such as the BION® microstimulator (Boston Scientific Corporation, Natick, Mass., USA), some features of which are described, for example, in U.S. Pat. No. 5,193,540 to Schulman et al., which is incorporated herein by reference.

Typically, electrode contact surfaces 100 are configured to be coupled to respective sites on or in stomach 20 of a patient. Typically, the electrode contact surfaces are configured to be applied in physical contact with muscle tissue of the stomach (e.g., fundus), such as by being inserted into a muscular layer of the stomach (e.g., fundus). In general, the specific sites on the fundus (and antrum and corpus) shown in the figures are exemplary, and the electrode contact surfaces may be applied to other sites on the stomach. For some applications, a conductive portion of the control unit serves as one of the electrode contact surfaces, or an electrode contact surface remote from the stomach is provided as one of the electrode contact surfaces.

Figure 3:
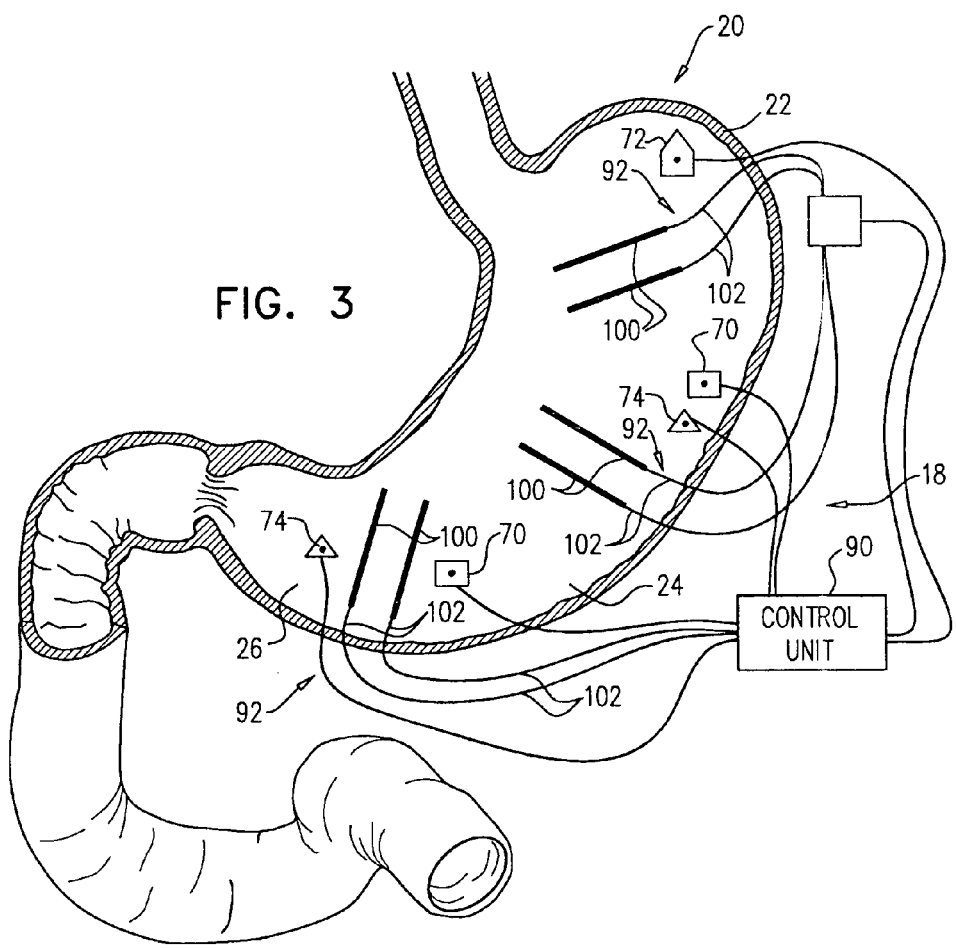
FIG. 3 is a schematic illustration of the gastrointestinal apparatus of FIG. 1 comprising additional electrode contact surfaces and sensors, in accordance with an application of the present invention.

Electrode contact surfaces 100 are typically configured to be coupled to an outer surface of the stomach, an inner surface of the stomach, or a layer of the stomach, such as the serosal layer of stomach 20, and/or inserted into the muscular layer of the stomach, or to a combination of the above. Alternatively, one or more of the electrode contact surfaces are coupled to tissue near the stomach (e.g., the pyloric region, the duodenum, or abdominal muscle in the vicinity of the stomach), which may for example simplify the surgical implantation procedure. Alternatively or additionally, the electrode contact surfaces are coupled elsewhere on the GI tract, or to other suitable locations in or on the patient's body. The number of electrode contact surfaces, as well as the positions thereof, are shown in FIGS. 1 and 3 by way of example, and other sites on stomach 20 or in or on the patient's body are appropriate for electrode contact surface placement in other applications of the present invention.

Different types of electrode structures known in the art are typically selected based on the specific condition of the patient's disorder, and may comprise stitch, coil, screw, patch, basket, needle and/or wire electrodes, or substantially any other electrode known in the art of electrical stimulation or sensing in tissue.

For some applications, each of electrode contact surfaces 100 has a length of between 1 and 25 mm, such as 18 mm, and a diameter of between 0.1 and 5 mm, such as 0.5 mm. For some applications, the electrode contact surfaces comprise a platinum-iridium (Pt/Ir) alloy, and optionally are coated, such as with Titanium Nitride (TiN). For some applications, the electrode contact surfaces are configured to have a current density of at least 0.15 mA/mm$^2$, no more than 1.3 mA/mm$^2$, and/or between 0.15 mA/mm$^2$ and 1.3 mA/mm$^2$.

Figure 6:
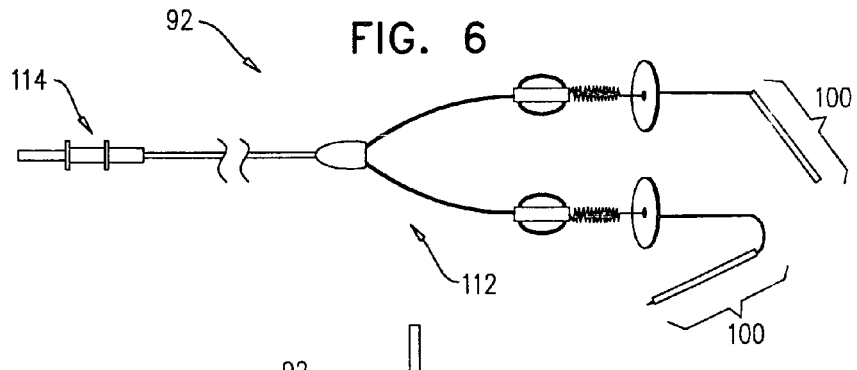
FIG. 6 is a schematic illustration of a bipolar bifurcated electrode structure, in accordance with an application of the present invention.

Reference is made to FIG. 6, which is a schematic illustration of a bipolar bifurcated electrode structure 92, in accordance with an application of the present invention. Electrode structure 92 comprises two electrode contact surfaces 100, a bifurcated lead 112, and a connector 114 for coupling the structure to control unit 90 (such as an IS-1 connector, as is known in the art). In this application, electrode structure 92 may comprise, for example, the UltraFlex Implantable Gastric Lead (MetaCure (USA), Orangeburg, N.Y.).

Figure 8:
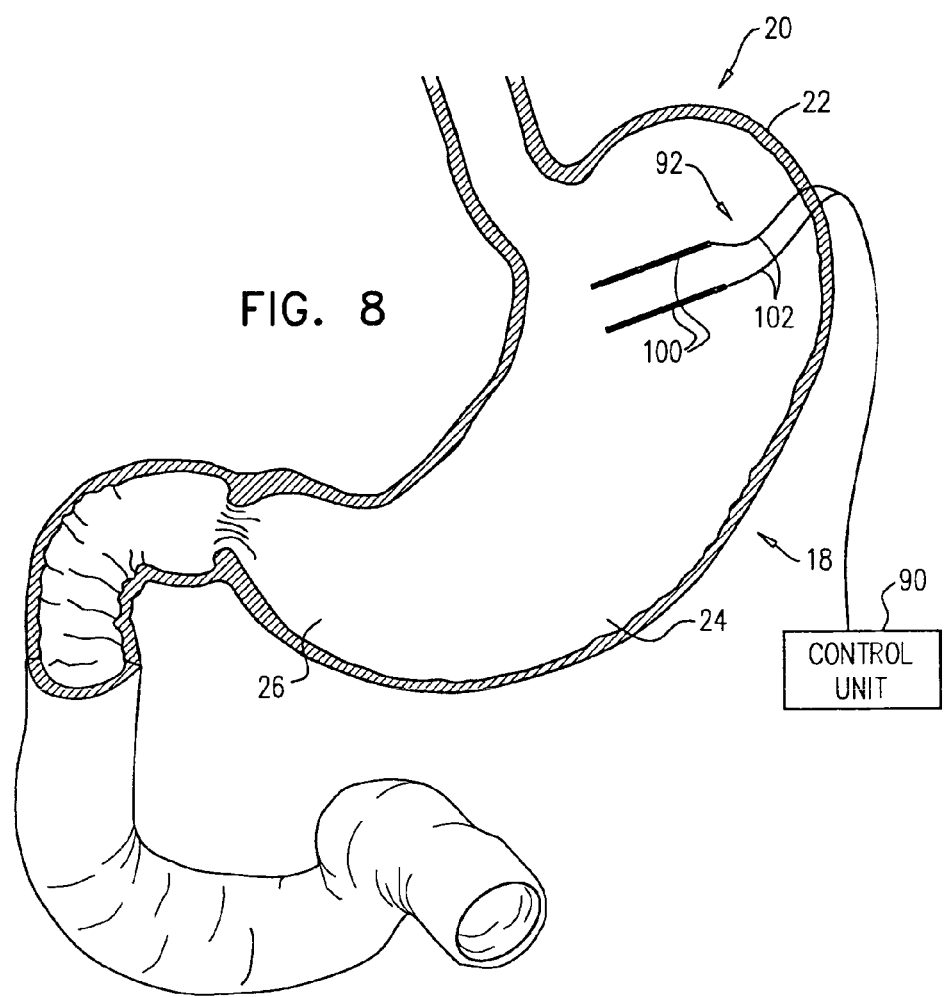
FIG. 8 is a schematic illustration of another configuration of the apparatus of FIG. 1, in accordance with an application of the present invention.

For some applications (as shown in FIG. 8), apparatus 18 comprises exactly one connector 114, which connects one or more of the leads (insulated cables) to control unit 90. For some applications, one end of exactly one of the insulated cables is coupled to the control unit.

For some applications (as shown in FIG. 8), apparatus 18 comprises exactly one bifurcated insulated cable, having exactly two bifurcated ends and exactly one non-bifurcated end, wherein each of the electrode contact surfaces are coupled to one of the bifurcated ends, and wherein the non-bifurcated end is coupled to the control unit. Alternatively, for some applications, apparatus 18 comprises exactly one multifurcated insulated cable, having at least three multifurcated ends and exactly one non-multifurcated end, wherein each of the electrode contact surfaces are coupled to one of the multifurcated ends, and wherein the non-multifurcated end is coupled to the control unit.

For other applications, electrode structure 92 comprises a corkscrew-shaped electrode mount, which is configured to be implanted in a wall of the fundus, and which comprises the one or more electrode contact surfaces, at respective sites of the electrode mount; for example, techniques may be used that are described in US Patent Application Publication 2010/0228105, which is incorporated herein by reference (for example, techniques may be used that are described therein with reference to FIGS. 14A-B).

Reference is again made to FIG. 1. For some applications, electrode structures 92 are bipolar, while for other applications the electrode structures are monopolar. For some applications in which the electrode structures are bipolar, the cathode electrode contact surface and anode electrode contact surface are placed between 1 and 4 cm apart from each other, e.g., between 2 and 4 cm apart. For some applications, the electrode contact surfaces are sutured to the stomach, such as to muscle tissue of the stomach. For some applications, the electrode implantation procedure is performed via laparoscopy or endoscopically. For some applications in which the electrode structures comprise at least one monopolar electrode structure, the return electrode contact surface may comprise a conductive portion of the device or another remotely-placed electrode, for example at least 5 cm away.

Reference is made to FIG. 8, which is a schematic illustration of another configuration of apparatus 18, in accordance with an application of the present invention. For some applications, apparatus 18 comprises exactly one electrode structure 92, which comprises one or more electrode contact surfaces 100, which are configured to be applied to the fundus of the patient. Thus, for these applications, apparatus 18 does not comprise any electrode structures that are applied elsewhere to the stomach, including the antrum. As a result, implantation procedures are substantially simplified. For example, electrode structure 92 and, optionally, control unit 90, may be implanted in a relatively simple endoscopic procedure via the lumen of the stomach. (It is substantially simpler to implant electrode contact surfaces in the fundus than in the antrum.) Typically, such an endoscopic implantation procedure has a duration of less than 45 minutes, such as about 30 minutes (compared to about 2.5 hours for implanting the TANTALUS® System mentioned hereinabove in the Background of the Application). Furthermore, application of the signal described herein only to the fundus may require a relatively low amount of energy, enabling the use of a small battery in the control unit. The control unit thus may be smaller than implantable control units used in some devices (such as the TANTALUS® System), further simplifying the endoscopic implantation procedure. For example, the control unit (e.g., an outer casing thereof) may be sized such that at least one line that passes from edge to edge of the control unit through a center of gravity thereof has a length of no more than 2 cm, such as no more than 1 cm (for example, for applications in which the control unit is generally cylindrical in shape, the line may correspond with the diameter of the control unit). In addition, the shorter and simpler implantation procedure may allow the use of local or twilight anesthesia, rather than the general anesthesia that may be required for implanting some devices (such as the TANTALUS® System) in some circumstances.

For some applications, an implantation procedure comprises endoscopically making one or more incisions (for some application, exactly one incision) through a fundic wall of the patient, and, via exactly one of the one or more incisions, implanting the one or more electrode contact surfaces 100 in contact with the fundus. Typically, to make the one or more incisions, an endoscopic tool is advanced into the stomach via a mouth of the patient. For some applications, control unit 90 is also implanted in a body of the patient via the exactly one incision. The control unit drives the one or more electrode contact surfaces to apply the signal described herein to the fundus. (If one or more additional incisions are made other than the exactly one incision through which the one or more electrode contact surfaces are implanted, these one or more additional incisions may be used, for example, to pass tools outside the stomach for use during the implantation procedure.)

For some applications, endoscopic implantation techniques are used, mutatis mutandis, that are described in above-mentioned PCT Publication WO 07/080,595 or U.S. application Ser. No. 12/160,616 in the national stage thereof, both of which are assigned to the assignee of the present application and incorporated herein by reference.

For some applications, control unit 90 is implantable, and comprises one or more non-rechargeable batteries with a combined capacity of no more than 1 A·h, such as no more than 0.1 A·h. Alternatively, for some applications, the control unit comprises one or more rechargeable batteries with a combined capacity of no more than 5 mA·h (milliamp hours), such as no more than 1 mA·h. Alternatively or additionally, for some applications, the batteries (whether rechargeable or non-rechargeable) have a combined maximum energy discharge over a 24-hour period (such as over all 24-hour periods) of 5 J, such as no more than 2 J. Alternatively or additionally, for some applications, control unit 90 is configured to drive all electrode contact surfaces of apparatus 18 using no more than 5 J (such as no more than 2 J) over a 24-hour period (such as over all 24-hour periods of operation of the apparatus). (For applications in which the control unit comprises one or more rechargeable batteries, the batteries are optionally recharged by wirelessly transmitting energy to the control unit from outside of the body of the patient.)

Figure 7:
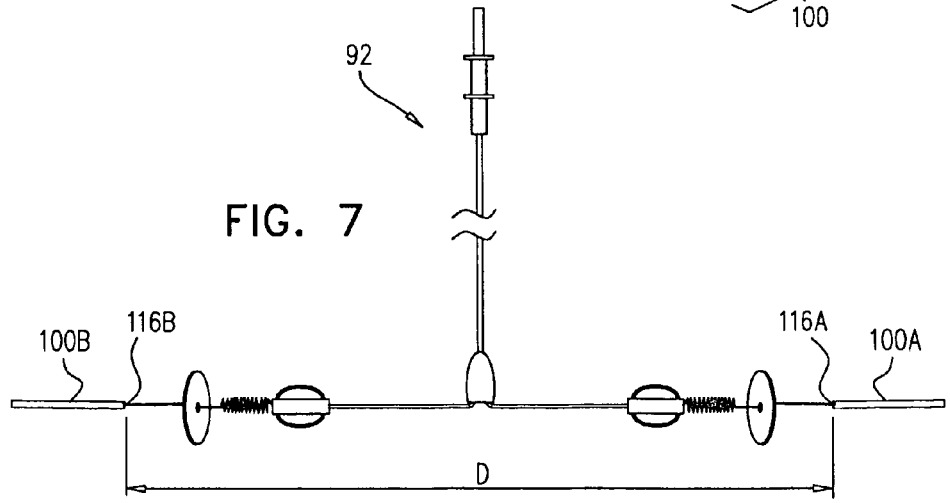
FIG. 7 is a schematic illustration of a configuration of an electrode structure, in accordance with an application of the present invention.

Reference is made to FIG. 7, which is a schematic illustration of a configuration of electrode structure 92, in accordance with an application of the present invention. For some applications in which apparatus 18 comprises exactly one electrode structure 92, electrode structure 92 comprise a plurality of electrode contact surfaces 100. The electrode structure is configured to constrain motion of electrode contact surfaces 100 so as to define a greatest possible distance D between closest respective portions 116 of any two of electrode contact surfaces 100, which distance is no more than 40 cm, such as no more than 30 cm, 20 cm, 10 cm, or 5 cm. (In the example shown in FIG. 7, two electrodes 100A and 100B are provided, having respective closest portions 116A and 116B, respectively.) For some applications, more than one of electrode contact surfaces 100 are arranged along a single lead; for example, the lead may include non-electrically-insulated portions that serves as respective electrode contact surfaces (configuration not shown).

Control unit 90 drives electrode contact surfaces 100 to apply an electrical signal to stomach 20, such as fundus 22, and configures the signal to improve a blood glucose level of the patient, such as normalize the level, acutely and/or chronically, i.e., over a longer period of time, such as a period of time having a duration of at least three months. The electrical signal may be delivered, for example, through circuitry that generates electrical current to flow through at least one of electrode contact surfaces 100 in the vicinity of the target tissue. Alternatively or additionally, the signal may be delivered through circuitry that generates an electric field between at least one of electrode contact surfaces 100 in the vicinity of the target tissue and another of the electrode contact surfaces, a reference surface, and/or a conductive portion of a signal generator (or control unit 90). For some applications, the control unit does not sense eating by the patient (e.g., by detecting swallowing and/or changes in fundic or antral mechanical and/or electrical activity) or a characteristic of food eaten by the patient. (As used in the present application, including the claims, "food" is to be understood as including both solid and liquid food.) For some applications, the control unit is configured to apply the signal to the at least one fundic site at least intermittently during a period having a duration of at least one week, without applying any electrical signals to any antral sites of the patient during the period.

Apparatus 18 is configured to treat a condition of the patient, such as type 2 diabetes, type 1 diabetes, metabolic syndrome, impaired glucose tolerance (IGT), impaired fasting glycemia (IFG), obesity, diabetes (type 2 or type 1) combined with obesity, gastroparesis, or another condition. Control unit 90 typically configures the signal to not cause hypoglycemia. For some applications, the control unit effects this avoidance of hypoglycemia without periodically measuring the blood glucose level of the patient during application in the signal. For these applications, the control unit thus does not modulate any parameters of the signal, and/or withhold applying the signal, responsively to the periodically measured blood glucose level of the patient.

For some applications, control unit 90, the electrode structures (including electrode contact surfaces 100), and the various sensors described herein are implanted in the patient in a manner generally similar to that used to implant gastric pacemakers or other apparatus for stimulating the GI tract which are known in the art. For some applications, implantation techniques may be used that are described in PCT Publication WO 07/080,595, and in U.S. patent application Ser. No. 12/160,616 in the national stage thereof, both of which are incorporated herein by reference. As appropriate, techniques described in one or more of the patents cited in the Background section of the present patent application may be adapted for use with these embodiments of the present invention.

Typically, apparatus 18 is configured to be implantable in the patient for long-term application of the electrical signal.

For some applications, two electrode contact surfaces 100 are placed in or on the anterior wall of the fundus (as shown in FIGS. 1 and 3), and/or two electrode contact surfaces 100 are placed in or on the posterior wall of the fundus (configuration not shown). For some applications, the electrode contact surfaces are placed such that a closer one of the electrode contact surfaces is 1-3 cm (e.g., 2 cm) from the gastroesophageal junction. Optionally, the electrode contact surfaces are placed perpendicular to the long axis of the stomach.

Alternatively, for some applications, one of electrode contact surfaces 100 is placed in or on an anterior wall of fundus 22, and the other electrode contact surface 100 is placed in or on the posterior wall of the fundus (configuration not shown). For some applications, the electrode contact surfaces are coupled to multiple sites along the stomach, such as the anterior side of the antrum or corpus and the posterior site of the antrum or corpus.

For some applications, a single bipolar electrode structure is implanted in the stomach, such as in the fundus (configuration not shown). For example, the bipolar electrode structure may be similar to a cardiac pacing lead, and have a tip and ring on the same body of the lead. The use of a single bipolar electrode structure simplifies the surgical implantation procedure and reduces the cost of the procedure. Alternatively, a single bipolar bifurcated lead 102 is used, and the two electrode contact surfaces of the bifurcated lead are implanted in the stomach, such as in the fundus. For example, the bifurcated lead may have a single lead body that splits into two sub-bodies, each having its own electrode contact surface (such that the lead is Y-shaped), such as shown in FIG. 6. Use of such a bifurcated lead may cause activation of a large portion of the stomach (e.g., fundus) using a single lead.

Further additionally, two leads 102 are provided, each of which comprises a single respective unipolar electrode contact surface 100 (configuration not shown).

Alternatively, for some applications, electrode contact surfaces 100 (or one or more addition sets of electrode contact surfaces) are applied to a corpus 24 of stomach 20, and/or an antrum 26 of the stomach 20. For some applications, three respective bipolar electrode structures are implanted in the fundus, corpus, and antrum, and are activated to apply the signal. For other applications, two respective bipolar electrode structures are implanted in two sites selected from the group consisting of: the fundus, corpus, and antrum (fundus and corpus, fundus and antrum, or antrum and corpus), and are activated to apply the signal. For still other applications, two monopolar electrode structures are implanted in two sites selected from the group consisting of: the fundus, corpus, and antrum (fundus and corpus, fundus and antrum, or antrum and corpus), and are activated to apply the signal between the two sites. The two monopolar electrode structures may share a single lead, or may have separate respective leads. For some applications in which the electrode contact surfaces are implanted in the antrum, the electrode contact surfaces are positioned 1-3 cm (e.g., 2 cm) from the pylorus, and/or the electrode contact surfaces are placed perpendicular to the long axis of the stomach. For some applications in which the electrode contact surfaces are implanted in the corpus, the electrode contact surfaces are placed perpendicular to the long axis of the stomach. For all applications in which one or more electrode contact surfaces are implanted in the corpus, the electrode contact surfaces may be implanted in the greater and/or lesser curvatures thereof.

The electrical signal generated by the control unit may have a variety of parameters and/or properties, including with regard to its shape, duty cycle, frequency, duration, offset, and combination of pulses. For some applications, the control unit drives the electrode contact surfaces to apply the electrical signal as a plurality of pulses. For some applications, the control unit configures one or more of the pulses (such as a majority of the pulses, or all of the pulses) to have one or more of the following parameters:

- a pulse width of at least 1 microsecond, no more than 2 seconds, and/or between 1 microsecond to 2 seconds (e.g., at least 2 microseconds, no more than 5 milliseconds, and/or between 2 microseconds and 5 milliseconds), such as at least 5 microseconds, no more than 100 milliseconds, and/or between 5 microseconds and 100 milliseconds, e.g., at least 10 microseconds, no more than 10 milliseconds, and/or between 10 microseconds and 10 milliseconds, such as at least 15 microseconds, no more than 5 milliseconds, and/or between 15 microseconds and 5 milliseconds, e.g., at least 20 microseconds, no more than 1 millisecond, and/or between 20 microseconds and 1 millisecond, such as at least 25 microseconds, no more than 100 microseconds, and/or between 25 and 100 microseconds, for example, about 30 microseconds;
- a voltage of no more than 10 volts, such as at least 0.5 volts, e.g., at least 1.25 volts, no more than 4.1 volts, and/or between 1.25 and 4.1 volts, e.g., 3.5 volts;
- an amplitude of at least 0.1 mA, no more than 100 mA, and/or between 0.1 mA and 100 mA, typically at least 5 mA (e.g., at least 10 mA), no more than 35 mA, and/or between 5 mA (e.g., 10 mA) and 35 mA (which depends on the tissue impedance) (because an amplitude of greater than between 13 and 15 mA usually (but not always) is felt by the patient, it is generally desirable to limit the amplitude to no more than the sensation threshold of the particular patient). For example, in an extreme case, tissue impedance (electrode-tissue interface impedance) may be as high as 700 ohms; in this case, if voltage of 3.5 volts is applied, the current is 5 mA;
- pulses that are uniphasic or biphasic (with or without a gap between the two phases or consecutive pulses);
- pulses that are substantially square, saw tooth, sinusoidal, exponential, ramping, triangular, capacitor discharge (approximately exponential), having sharp or gradual gradients, symmetric or asymmetrical, or a combination of these properties;
- a pulse frequency of at least 1 Hz, such as at least 10 Hz or 20 Hz, no more than 100 Hz, or at least one pulse per second, five pulses per second, ten pulses per second, or 20 pulses per second, and/or no more than 100 pulses per second;
- an energy per pulse (e.g., an average energy per pulse) of at least 0.05 microjoules, no more than 50 microjoules, and/or between 0.05 and 50 microjoules, such as at least 0.1 microjoules, no more than 5 microjoules, and/or between 0.1 and 5 microjoules; and/or
- an instantaneous power of at least 0.1 milliwatts, no more than 500 milliwatts, and/or between 0.1 milliwatts and 500 milliwatts, such as at least 5 milliwatts, no more than 100 milliwatts, and/or between 5 milliwatts and 100 milliwatts.

For some applications, the control unit generates the electrical signal using no more than 5 J (such as no more than 2 J) over a 24-hour period (such as over all 24-hour periods of operation of the apparatus).

For some applications, the pulses are applied in a plurality of pulse trains, one or more of which trains (such as a majority or all) typically has one or more of the following parameters:

- a total duration of each train of pulses of at least 0.1 seconds, no more than 5 seconds, and/or between 0.1 and 5 seconds, such as at least 0.5 seconds, no more than 2 seconds, and/or between 0.5 and 2 seconds;
- a number of pulses per train of at least 1, no more than 100,000, and/or between 1 and 100,000, such as at least 100, no more than 20,000, and/or between 100 and 20,000; and/or
- biphasic pulses, such as described hereinbelow with reference to FIG. 2.

For some applications in which the pulses are uniphasic, the phase of the pulses alternates from time to time (e.g., once every several seconds (e.g., one minute) to every 24 hours, or once every one or more physiological cycles of the tissue to which the electrode contact surfaces are coupled) between positive and negative pulses. For some applications, a trailing balancing phase is provided after one or more of the pulses. Use of such alternating phases and/or trailing balancing phase may reduce the effect of polarization of the electrode contact surfaces.

Typically, the electrical signal is not synchronized with intrinsic electrical activity of the stomach. Alternatively, the electrical signal is synchronized with intrinsic electrical activity of the stomach. For example, application of the signal may be triggered by gastric electrical and/or mechanical activity, e.g., slow waves.

For some applications, electrode contact surfaces 100 are configured to be applied to the fundus. Control unit 90 is configured to:

- during first and second modes of operation, drive electrode contact surfaces 100 to apply an electrical signal to the fundus that chronically improves a blood glucose level of the patient, in order to treat the patient, and during the first mode of operation, and not during the second mode of operation, sense a parameter that varies in response to the applied electrical signal, and calculate, based on the sensed parameter, an impedance of tissue of the fundus.

For some applications, the control unit is configured to operate in the second mode of operation for a greater total amount of time than in the first mode of operation.

Determining impedance only a portion of the time the device operates (i.e., only during the first mode of operation) reduces energy consumption, which, among other benefits, may reduce the battery size of the control unit, as discussed above.

For some applications, electrode contact surfaces 100 are configured to be applied to the fundus. Control unit 90 is configured to:
  drive electrode contact surfaces 100 to apply, during a plurality of signal application time periods, an electrical signal to the fundus that chronically improves a blood glucose level of the patient, in order to treat the patient,
  sense a parameter that varies in response to the applied electrical signal, and calculate, based on the sensed parameter, an impedance of tissue of the fundus, and
  withhold sensing the parameter for a duration of at least one second following at least a portion of the signal application time periods.

As mentioned above, determining impedance only a portion of the time the device operates (i.e., only during the first mode of operation) reduces energy consumption, which, among other benefits, may reduce the battery size of the control unit, as discussed above.

For some applications, electrode contact surfaces 100 are configured to be applied to the fundus. Control unit 90 is configured to:
  drive electrode contact surfaces 100 to apply an electrical signal to the fundus that chronically improves a blood glucose level of the patient, in order to treat the patient, wherein the electrical signal includes a plurality of pulses, and
  during application of less than 50% (e.g., less than 10%, such as less than 2%) of the pulses: (a) sense a parameter that varies in response to the applied electrical signal, and (b) calculate, based on the sensed parameter, an impedance of tissue of the fundus.

As mentioned above, determining impedance only a portion of the time the device operates (i.e., only during the first mode of operation) reduces energy consumption, which, among other benefits, may reduce the battery size of the control unit, as discussed above.

For some applications, control unit 90 is configured to configure one or more parameters of the electrical signal responsively to the calculated impedance. For example, control unit 90 may be configured to apply the electrical signal in a series of pulses, and to set a duration of the pulses at least in part responsively to the calculated impedance.

For some applications, electrode contact surfaces 100 are configured to be applied to the fundus. Control unit 90 is configured to apply the electrical signal intermittently. Such intermittent signal application generally reduces power consumption, while still achieving the therapeutic goal of chronically (and/or acutely) reducing blood glucose levels. Reduced power consumption, among other benefits, may reduce the battery size of the control unit, as discussed above.

For example, the control unit may be configured to:
  during signal-application periods, drive electrode contact surfaces 100 to apply an electrical signal to the fundus that chronically improves a blood glucose level of the patient, in order to treat the patient, and
  provide reduced-signal-application periods, which alternate with the signal-application periods, and during which electrode contact surfaces 100 apply the electrical signal having an average energy that is less than 20% of the average energy of the electrical signal applied during the signal-application periods.

Typically, the control unit is configured to provide at least one, such at least three, reduced-signal-application periods during every 24-hour period, each of which reduced-signal-application periods has a duration of at least 30 minutes, such as at least 2 hours.

For some applications, the reduced-signal-application periods are non-signal-application periods; the control unit is configured to withhold driving the electrode contact surfaces to apply the electrical signal during the non-signal-application periods.

For some applications, the control unit is configured to drive the electrode contact surfaces, during the signal-application periods, to apply the electrical signal as a plurality of pulses alternating with inter-pulse gaps.

For some applications, the control unit is configured to set a duration of at least one of the signal-application periods every 24 hours to be at least 10 minutes, such as at least 30 minutes, one hour, or 3 hours.

For some applications, the control unit is configured to provide the reduced-signal-application periods in accordance with a predetermined schedule.

For some applications, the control unit is configured to sense eating by the patient, and to apply the electrical signal during the signal-application periods in response to the sensed eating. Alternatively, for some applications, the control unit is configured to sense eating by the patient, and to provide the reduced-signal-application periods in response to the sensed eating.

For some applications, the control unit is configured to provide the signal-application periods only during a plurality of hours during nighttime. Alternatively, for some applications, the control unit is configured to provide the signal-application periods only during a plurality of hours during daytime.

For some applications, implantable electrode contact surfaces 100 are configured to be applied to the fundus. Control unit 90 is configured to drive electrode contact surfaces 100 to apply an electrical signal to the fundus that chronically improves a blood glucose level of the patient, in order to treat the patient, without the control unit applying, or generating a signal for applying, any additional glucose-control or weight-control therapy to the patient. Typically, for these applications, apparatus 18 does not comprise any electrode contact surfaces that are configured to be applied to an antrum of the patient.

For some applications, electrode contact surfaces 100 are configured to be applied to the fundus. Control unit 90 is configured to drive the electrode contact surfaces to apply an electrical signal to the fundus that chronically improves a blood glucose level of the patient, in order to treat the patient, without calculating an impedance of tissue of the fundus based on a sensed parameter that varies in response to the electrical signal. Not determining impedance reduces energy consumption, which, among other benefits, may reduce the battery size of the control unit, as discussed above.

For some applications, control unit 90 is configured to configure the electrical signal such that the signal, if applied to an antrum of the patient, would not effect an improvement in a blood glucose level of the patient.

Figure 2:
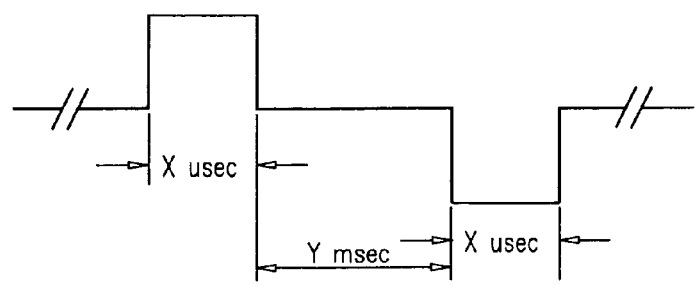
FIG. 2 is a schematic illustration of a portion of a biphasic signal, in accordance with an application of the present invention.

Reference is now made to FIG. 2, which is a schematic illustration of a portion of a biphasic signal, in accordance with an application of the present invention. Each pulse includes a positive phase and a negative phase; the positive phase may precede or follow the negative phase. For some applications, each of the phases has a duration (labeled X in the figure) of at least 1 usec, no more than 500 usec, and/or between 1 and 500 usec, such as at least 10 usec, no more than 100 usec, and/or between 10 and 100 usec, e.g., 30.5 usec or 61 usec (optionally, the duration is selected based on the measured tissue impedance, i.e., electrode-tissue interface impedance). For some applications, the control unit, or a medical worker, sets the duration of the pulses at least in part responsively to measured tissue impedance, i.e., electrode-tissue interface impedance.

For some applications, each pulse includes a gap between the positive and negative phases (labeled Y in the figure), which typically has a duration of between 1 usec and 1 msec. The length of the gap may sometimes be constrained by performance of the circuitry (such as the amount of time necessary to open and close switches necessary for discharging a capacitor into the tissue), but for some applications may be programmable, such as between 0.1 usec and 100 msec, e.g., between 100 usec and 1 msec. For other applications, a gap is not provided between the phases.

For some applications, the biphasic pulses are applied at least 1 time, no more than 100 times, and/or between 1 and 100 times per second, such as at least 5 times, no more than 40 times, and/or between 5 and 40 times per second, e.g., 10 times per second. (The number of phases per second equals twice the number of pulses per second.) The pulses are typically applied continuously when the signal is applied.

For some applications, the control unit applies the signal using a capacitor having a capacitance of between 0.1 nF and 10,000 nF, such as 390 nF. For some applications, the capacitor discharge occurs within between 10 usec and 1 msec, such as about 100 usec, after application of each pulse (assuming a 390 nF capacitance into an approximately 250 ohm load). Circuitry described hereinbelow with reference to FIG. 5 may be used for applying the signal using a capacitor.

For some applications, the control unit is configured to deliver the stimulation during eating, and, optionally, for a specific time after eating, by the patient. The control unit may be configured to detect such eating, such as using sensors and techniques described hereinbelow with reference to FIG. 3, or to receive an input from the patient manually activating the signal application, for example, upon experiencing a severe symptom, such as nausea. Typically, the control unit is configured to deliver the stimulation for a period having a duration of between 0.5 and 4 hours, beginning after commencement of eating. Alternatively, the control unit is configured to apply the stimulation at certain time(s) of day. This approach obviates the need for an eating detection sensor and its associated lead, and also eliminates the need for patient compliance, and an associated external manual controller device.

For some applications, the apparatus is configured to measure the blood glucose level of the patient, and to apply the signal only when the measured blood glucose level is greater than a threshold value. For example, the apparatus may use supplemental sensors 72, described hereinbelow with reference to FIG. 3, for measuring the blood glucose level.

For some applications, the control unit is configured to synchronize the applied electrical stimulation with electrical activity of the stomach, while for other applications, the stimulation is not synchronized with electrical activity of the stomach.

Reference is now made to FIG. 3, which is a schematic illustration of gastric apparatus 18 comprising additional electrode contact surfaces and sensors, in accordance with an application of the present invention. As mentioned above, electrode contact surfaces 100 may function as signal-application electrode contact surfaces. For some applications, electrode contact surfaces 100 may also operate in a sensing mode. In addition, one or more dedicated local sense electrode contact surfaces 74 may also be placed on or in stomach 20, and convey electrical signals to control unit 90 responsive to natural gastric electric activity, such as for detecting slow waves. In addition, one or more mechanical sensors 70 (e.g., accelerometers, force transducers, strain gauges, or pressure gauges) may be coupled to the control unit and are placed on or in the stomach. Alternatively or additionally, one or more supplemental sensors 72 (e.g., pH sensors, blood glucose sensors, intragastric pressure sensors and/or sonometric sensors) may be coupled to the control unit and are placed on or in the GI tract or elsewhere on or in the patient's body. The control unit may modify the waveform applied through electrode contact surfaces 100 responsive to signals from sensors 70 and 72 and local sense electrode contact surfaces 74, as described hereinbelow with reference to FIG. 4. Typically, control unit 90 and the above-mentioned electrode contact surfaces and sensors are permanently or semi-permanently implanted in or coupled to the patient's body.

Techniques for detecting eating may be used that are described in U.S. Pat. No. 7,437,195, U.S. Pat. No. 7,330,753, US Patent Application Publication 2009/0118797, US Patent Application Publication 2009/0281449, and/or PCT Publication WO 08/117,296, all of which are incorporated herein by reference. For some applications, techniques described herein as detecting eating detect any eating (i.e., either solids or liquids), while for other applications, the control unit only applies the glucose-improvement stimulation upon detecting eating of solid foods, such as using the techniques described in these applications incorporated herein by reference. Alternatively or additionally, the control unit is configured to modify one or more parameters of the stimulation upon detecting eating or upon detecting eating of solid foods.

Figure 4:
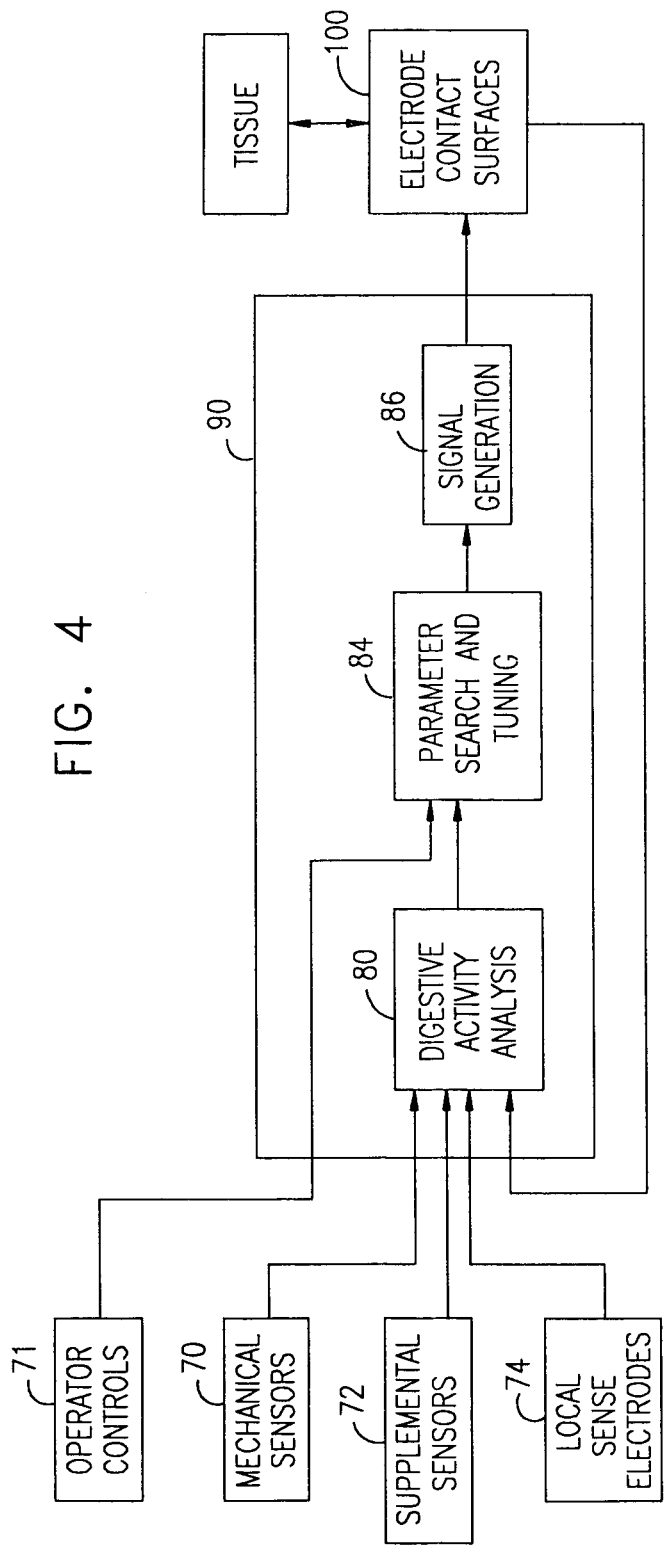
FIG. 4 is a schematic block diagram of a control unit of the gastrointestinal apparatus of FIGS. 1 and 3, in accordance with an application of the present invention.

FIG. 4 is a schematic block diagram of control unit 90, in accordance with an application of the present invention. Mechanical sensors 70, supplemental sensors 72, local sense electrode contact surfaces 74, and electrode contact surfaces 100 may be coupled to provide feedback signals to a digestive activity analysis block 80 of control unit 90. The feedback signals generally provide block 80 with information about various aspects of the stomach's present state (e.g., empty or full) and the stomach's level of activity, so as to enable block 80 to analyze the signals and actuate control unit 90 to modify the electrical energy applied to electrode contact surfaces 100 responsive to the analysis. For some applications, the enhancement signal is adjusted by the control unit responsive to the feedback signals in order to yield a desired response, or an indication by supplemental sensors 72 of maintenance of the patient's blood sugar level within a desired range.

As shown in FIG. 4, digestive activity analysis block 80 typically conveys results of its analysis of the inputs from mechanical sensors 70, supplemental sensors 72, and electrode contact surfaces 100 to a "parameter search and tuning" block 84 of control unit 90, which iteratively modifies characteristics of the electrical energy applied to stomach 20 in order to attain a desired response, such as blood glucose level improvement. For some applications, operating parameters of block 84 are entered, using operator controls 71, by a physician or other human operator of the control unit. Block 84 typically utilizes multivariate optimization and control methods known in the art in order to cause one or more of the aforementioned mechanical, electrical, chemical and/or other measured parameters to converge to desired values.

Typically, desired signal parameters are conveyed by block 84 to a signal generation block 86 of control unit 90, which generates, responsive to the parameters, electrical signals that are applied by electrode contact surfaces 100 to the stomach. Block 86 typically comprises amplifiers, isolation units, and other standard circuitry known in the art of electrical signal generation.

In an initial calibration procedure, parameter search and tuning block 84 typically modifies a characteristic (e.g., timing, magnitude, or shape) of the signal applied through one of electrode contact surfaces 100, and then determines whether a predetermined response generally improves following the modification. For some applications, the calibration procedure is subsequently performed by the physician at intermittent follow-up visits, and/or by unit 90 automatically during regular use of apparatus 18 (e.g., daily).

For some applications, during the initial calibration procedure, the locations of one or more of electrode contact surfaces 100 are varied while the signal is applied therethrough, so as to determine optimum placement of the electrode contact surfaces. In a series of calibration steps, each electrode contact surface is moved over an area of stomach 20, and an appropriate response of the stomach is measured. After the physician considers that a sufficient number of sites have been investigated to characterize the area, the electrode contact surface is returned to the site yielding the best response. Subsequently, other electrode contact surfaces, placed on, in, or near the stomach are moved according to the same protocol, so as to achieve substantially optimum placement of some or all of the electrode contact surfaces.

Figure 5:
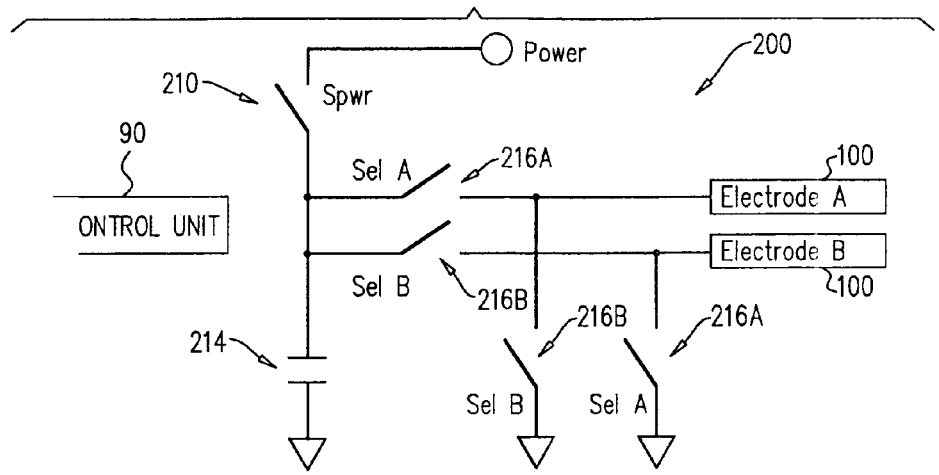
FIG. 5 is a schematic diagram of circuitry for applying the glucose level improvement signal, in accordance with an application of the present invention.

Reference is now made to FIG. 5, which is a schematic diagram of circuitry 200 for applying the glucose level improvement signal, in accordance with an application of the present invention. Circuitry 200 controls a switch 210 ("Spwr") that connects a power source 212 to charge a capacitor 214 which is connected to electrode contact surfaces 100. The power source thus charges the capacitor, and the capacitor discharges the charge to the tissue through the electrode contact surfaces. The electrode contact surfaces are separately controlled using respective electrode switches 216A ("SelA") and electrode switches 216B ("SelB").

Stimulation using some of the techniques described hereinabove was tested in two experiments conducted on a total of 12 human diabetic subjects suffering from type 2 diabetes. In each of the subjects, a bipolar electrode structure (UltraFlex Implantable Gastric Lead, MetaCure (USA), Orangeburg, N.Y.) was placed in the muscle layer of the anterior wall of the fundus about 2 cm from the Lower Esophageal Sphincter (LES), such that the two electrode contact surfaces of the bipolar electrode structure were 2 cm apart (generally as shown in FIG. 1). (The length of the lead from the IS-1 connector to the bifurcation was about 33-35 cm, and from the bifurcation to each of the electrodes was 10-12 cm. A control unit similar to control unit 90 was implanted. The control unit was configured to apply biphasic stimulation electrical pulses continuously (i.e., 10 times a second, every second of the day, every day until programmed off by a medical professional) for a period having a duration of three months. The pulses had a voltage of between 3.2 to 4.1 volts (5 mA-35 mA, depending on the tissue impedance), and were applied 10 times every second (i.e., at a frequency of 10 Hz). Each pulse included positive and negative phases, each of which phases had a duration of either 30.5 or 61 microseconds, depending on the electrode-tissue interface impedance. The control unit did not measure blood glucose, and the signal was thus not modulated or withheld responsive to blood glucose levels.

In two different experiments performed, after three months of treatment, the subjects showed a statistically significant improvement in HbA1c compared with baseline values prior to device implantation and activation. In one cohort (n=8), mean HbA1c decreased from 8.4% at baseline to 7.3% after three months treatment, P<0.01); while in the second cohort (n=4), mean HbA1c decreased from 7.12% at baseline to 6.65% after three months treatment. In six of the subjects, HbA1c decreased to less than 7%, reflecting normalization of blood glucose level. No hypoglycemia events were reported in any of the 12 subjects during the three months of stimulation.

In eight of the 12 subjects, the signal was applied for an additional three months (for a total of six months). The following table shows average HbA1c (percentage) for these eight subjects at baseline, at three months, and at six months:

TABLE 1

|  | Baseline (SD) | 3 months (SD) | 6 months (SD) |
|---|---|---|---|
| HbA1c | 8.1 ± 0.6 | 7.3 ± 0.8 | 6.9 ± 0.4 |

These results show a noticeable additional improvement in HbA1c from three to six months (P=0.06 at six months compared to baseline).

The experiment that included the above-mentioned cohort of eight patients additionally included five patients that served as a control group. The same system was implanted in these five patients as in the eight patients, including the control unit and electrode contact surfaces. However, the system was not activated in the control group. In the control group, on average no change was observed in HbA1c levels between baseline and 3 months after implantation (7.6%). Comparison of this lack of change with the decrease in HbA1c observed in the eight patients that received stimulation (at 6 months) was statistically significant (p=0.007).

Figure 9A:
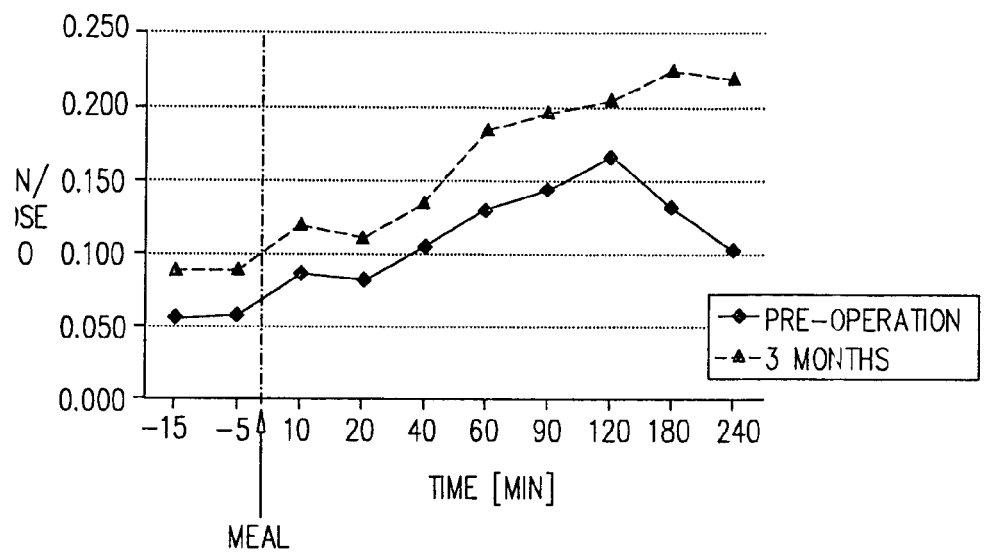
FIGS. 9A-B are graphs showing experimental results obtained in accordance with an application of the present invention.
Figure 9B:
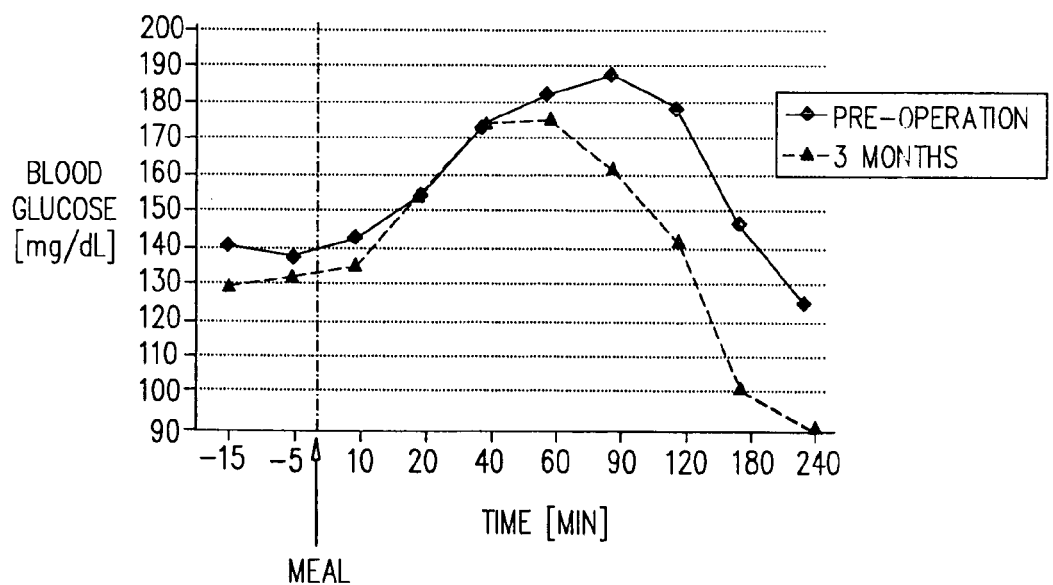

Reference is now made to FIG. 9A-B, which are graphs showing experimental results obtained in accordance with an application of the present invention. Stimulation using some of the techniques described hereinabove was tested in a third experiment conducted on a total of four human diabetic subjects suffering from type 2 diabetes (separate from the 12 subjects mentioned above). In each of the subjects, a bipolar electrode structure (UltraFlex Implantable Gastric Lead, MetaCure (USA), Orangeburg, N.Y.) was placed in the muscle layer of the anterior wall of the fundus about 2 cm from the Lower Esophageal Sphincter (LES), such that the two electrode contact surfaces of the bipolar electrode structure were 2 cm apart (generally as shown in FIG. 1). (The length of the lead from the IS-1 connector to the bifurcation was about 33-35 cm, and from the bifurcation to each of the electrodes was 10-12 cm. A control unit similar to control unit 90 was implanted. The control unit was configured to apply biphasic stimulation electrical pulses continuously (i.e., 10 times a second, every second of the day, every day until programmed off by a medical professional) for a period having a duration of three months. The pulses had a voltage of between 3.2 to 4.1 volts (5 mA-35 mA, depending on the tissue impedance), and were applied 10 times every second (i.e., at a frequency of 10 Hz). Each pulse included positive and negative phases, each of which phases had a duration of either 30.5 or 61 microseconds, depending on the electrode-tissue interface impedance. The control unit did not measure blood glucose, and the signal was thus not modulated or withheld responsive to blood glucose levels.

After three months of chronic treatment, all four of the subjects showed an improvement in postprandial glucose control, as reflected by the ratio of insulin to glucose, and glucose level. After three months of signal application, as described above, all four subjects were fed a test meal consisting of two slices of toast, 10 g butter, 20 g marmalade, two scrambled eggs, and one slice of cheese. Insulin and glucose levels were measured beginning 15 minutes before the meal, and eight times during the four-hour period after the meal. In addition, C-peptide, and four hormones related to the gastrointestinal system (as defined hereinabove) were also measured: ghrelin, glucagon, pancreatic polypeptide, and glucagon-like peptide-1 (GLP-1). As a control, the subjects were fed the same meal prior to implantation of the device ("pre-op").

The curves shown in FIG. 9A reflect the ratio of insulin to blood glucose at the measured time points, on average for the four subjects. As can be seen in the graph, the postprandial ratio of insulin to glucose increased after three months of signal-application compared to prior to application of the signal (pre-op). The improvement was particularly pronounced beginning at 60 minutes after the meal, and through the end of the measurement period (4 hours after the meal).

The curves shown FIG. 9B reflect blood glucose levels at the measured time points, on average for the four subjects. As can be seen in the graph, the area under the curve was lower after three months of signal-application compared to prior to application of the signal (pre-op). The improvement was particularly pronounced beginning at 60 minutes after the meal, and through the end of the measurement period (4 hours after the meal).

The following table shows measurements for glucose and C-peptide, and five hormones related to the gastrointestinal system, and/or associated with glycemic control and/or a metabolic disorder (e.g., metabolic syndrome): insulin, ghrelin, glucagon, pancreatic polypeptide, and GLP-1. The values in the table reflect the average (and Standard Error of Measurement (SEM)) areas under the curve (AUC) of all four subjects (except for GLP-1, which could be measured in only two of the subjects) over the postprandial period beginning 15 minutes before commencement of the meal and ending 4 hours after the meal.

TABLE 2

| | Area Under the Curve | |
|---|---|---|
| | Baseline (SEM) | 3 months (SEM) |
| Glucose (mg/dl/min) | 38,619 (5527) | 32,290 (2509) |
| Insulin (U/lit/min) | 5338 (1872) | 5845 (1963) |
| Ghrelin (pg/ml/min) | 160,413 (11607) | 155,953 (11804) |
| C-peptide (ng/ml/min) | 223 (39) | 234 (35) |
| Glucagon (Pg/mL/min) | 11,929 (1166) | 11,639 (1834) |
| Pancreatic polypeptide (pmol/L/min) | 31,699 (6045) | 34,668 (6606) |
| GLP-1 (pmol/L/min) | 352 (211) | 441 (255) |

As can be seen in the table, all of the measured values reflect positive trends and improved levels, indicative of improved glycemic control in diabetic patients. In particular:
the AUC of glucose tended to be lower following treatment;
the AUC of insulin tended to be higher following treatment;
the AUC of ghrelin tended to be lower following treatment. Fasting levels of ghrelin also tended to be lower after treatment;
the AUC of C-peptide tended to be higher following treatment. In particular, the AUC of C-peptide tended to be higher in the first hour after the meal following treatment;
the AUC of glucagon tended to be lower following treatment. In particular, the AUC of glucagon tended to be lower during the first 90 minutes after the meal following after treatment;
the AUC of pancreatic polypeptide (PP) tended to be higher following treatment. In addition, fasting levels of PP tended to be higher following treatment;
the AUC of GLP-1 tended to be higher after treatment; and
the AUC of peptide YY (PYY) (not shown in the table) did not change meaningfully following treatment.

For some applications, the control unit is configured to configure one or more parameters of the electrical signal to cause one or more of the improvements set forth above, and/or activating the control unit comprises configuring one or more parameters of the electrical signal to cause one or more of the improvements set forth above. For some applications, the control unit is configured to configure one or more parameters of the electrical signal to cause an improvement in a level (e.g., a postprandial level and/or a fasting level) of at least one hormone, such as a hormone related to (e.g., secreted by) the gastrointestinal system (e.g., stomach, such as the fundus and/or the antrum, the pancreas, and/or the duodenum), and/or a hormone associated with glycemic control and/or a metabolic disorder (e.g., metabolic syndrome), including, but not limited to, the hormones discussed above, and/or activating the control unit comprises configuring one or more parameters of the electrical signal to cause such an improvement in the level of the at least one hormone. For some applications, the improvement is a normalization of secretion, expression, and/or blood level of the at least one hormone. For some applications, the electrical signal causes a simultaneous improvement in a plurality of such hormones, such as normalization of secretion, expression, and/or blood levels of the hormones. For example, the electrical signal may upregulate some of the hormones and down-regulate others, as is therapeutically beneficial.

For some applications, the improvement includes one or more of the following improvements:
an improvement (e.g., an increase) in a level (e.g., a postprandial and/or fasting level) of insulin;
an improvement (e.g., a decrease) in a level (e.g., a postprandial and/or fasting level) of ghrelin;
an improvement (e.g., a decrease) in a level (e.g., a postprandial and/or fasting level) of glucagon;
an improvement (e.g., an increase) in a level (e.g., a postprandial and/or fasting level) of pancreatic polypeptide;
an improvement (e.g., an increase) in a level (e.g., a postprandial and/or fasting level) of GLP-1; and/or
an improvement (e.g., an increase) in a level (e.g., a postprandial and/or fasting level) of C-peptide.

For some applications, the glucose level improvement signal described herein is applied (e.g., to the fundus) in combination with application of a separate stimulation signal. For example, the separate stimulation signal may be configured to increase a force of contraction of muscle of the stomach, such as using techniques described in above-mentioned U.S. Pat. No. 6,600,953 to Flesler et al. Optionally, the signal is an Excitable-Tissue Control (ETC) signal, as described in the '953 patent.

FIGS. 10A-F are schematic illustrations of gastric control apparatus 180, in accordance with respective applications of the present invention. For some applications, apparatus 180 applies electrical energy to modify the activity of a portion of the gastrointestinal tract of a patient. Apparatus 180 typically comprises an implantable or external control unit 190, and one or more electrodes 200 coupled to control unit 190 by respective leads 202. For some applications, electrodes 200 are configured to be coupled to respective sites on or in a stomach 20 of a patient. Typically, the electrodes are configured to be inserted into a muscular layer of the stomach. In general, the specific sites on the antrum and corpus shown in the figures are exemplary, and the electrodes may be applied to other sites on the antrum and corpus.

Electrodes 200 are typically configured to be coupled to the serosal layer of stomach 20 and/or inserted into the muscular layer of the stomach. Alternatively or additionally, the electrodes are coupled elsewhere on the gastrointestinal tract, or to other suitable locations in or on the patient's body. The number of electrodes, as well as the positions thereof, are shown in FIGS. 10A-F by way of example, and other sites on stomach 20 or in or on the patient's body are appropriate for electrode placement in other applications of the present invention. Different types of electrodes known in the art are typically selected based on the specific condition of the patient's disorder, and may comprise stitch, coil, screw, patch, basket, needle and/or wire electrodes, or substantially any other electrode known in the art of electrical stimulation or sensing in tissue. For some applications, the electrodes comprise bipolar electrodes, while for other applications the electrodes comprise monopolar electrodes. For some applications in which the electrodes comprise bipolar electrodes, the cathode and anode are placed between 1 and 4 cm apart from each other (e.g., between 2 and 4 cm apart for applying the non-excitatory signal, and between 1 and 4 cm apart for applying the pacing signal or the neural activation signal). For some applications, the electrodes are sutured to muscle tissue.

Control unit 190 drives electrodes 200 to apply signals to the GI tract, such as stomach 20. For some applications, the control unit configures the signals pace peristaltic movement of material through the GI tract, such as through the stomach. The signals include a non-excitatory signal, such as an Excitable-Tissue Control (ETC) signal, and in addition, for some applications, an excitatory pacing signal. The pacing signal initiates contraction of the muscle of the GI tract by generating slow waves (propagating action potentials) in the muscle, while the non-excitatory signal modulates, e.g., increases, the contraction of the muscle, while not generating a propagating action potential in the tissue. For some applications, the non-excitatory signal modulates contraction forces induced by the pacing signal, while for other applications, the non-excitatory signal modulates contraction forces occurring naturally in the GI tract.

When applying an ETC signal, control unit 190 may use techniques described in the above-referenced U.S. Pat. Nos. 6,571,127 and 6,317,631, mutatis mutandis. For some applications, the ETC signal is applied responsive to natural electrical activity of stomach 20, for example, after a designated delay following a detected activation of a portion of the stomach. For these applications, described may be used that are described in the above-referenced U.S. Pat. No. 6,587,721 to Prutchi et al., mutatis mutandis. Alternatively, the ETC signal is applied subsequent to an artificial gastric pacing pulse, as described hereinbelow.

For some applications, control unit 190, electrodes 200, and the various sensors described herein are implanted in the patient in a manner generally similar to that used to implant gastric pacemakers or other apparatus for stimulating the gastrointestinal tract which are known in the art. For some applications, implantation techniques may be used that are described in PCT Publication WO 07/080,595, and in U.S. patent application Ser. No. 12/160,616 in the national stage thereof, both of which are incorporated herein by reference. As appropriate, techniques described in one or more of the patents cited in the Background section of the present patent application may be adapted for use with these embodiments of the present invention.

For the applications described herein with reference to FIGS. 10A-F and/or 11, apparatus 180 may have a number of configurations, including the following configurations.

Configuration 1

Reference is again made to FIG. 10A. In this configuration of apparatus 180, a set of bipolar electrodes 200A and 200B are placed at antrum 26 of stomach 20. Electrodes 200A and 200B are coupled to control unit 190 by leads 202A and 202B, respectively. For some applications, one of the electrodes 200A is placed on an anterior wall of antrum 26, and the other electrode 200B is placed on the posterior wall of the antrum 26.

For some applications, control unit 190 is configured to drive the electrodes to apply a non-excitatory signal, such as an ETC signal, to the antrum. The non-excitatory signal modulates, e.g., increases, the contraction of the muscle, while not generating a propagating action potential in the tissue.

For some applications, the control unit configures the non-excitatory signal with one or more of the following parameters:
- a pulse width of between 3 and 12 ms, such as between 5 and 8 ms, e.g., 5 ms or 6 ms;
- an amplitude of between 10 and 20 mA, such as between 10 and 13 mA (because an amplitude of greater than between 13 and 15 mA usually (but not always) is felt by the patient, it is generally desirable to limit the amplitude to no more than the sensation threshold of the particular patient);
- biphasic pulses, delivered in pulse trains of between 10 and 1000 pulses, such as between 20 and 200 pulses, e.g., between 50 and 150 pulses, such as between 20 and 120 pulses, e.g., 100 pulses, with a delay between pulses within a given train of between 0 and 500 ms, such as between 0.1 and 500 ms, such as between 0.25 and 100 ms, e.g., 0.25 ms or 2.5 ms, with a total train duration of between 2 and 3000 ms; and/or
- each pulse train includes on/off modulation, with on periods having a duration of between 5 and 20 minutes, such as between 10 and 15 minutes, and off periods having a duration of between 5 and 20 minutes, such as between 10 and 15 minutes; for example, each pulse train may begin with an on period of 15 minutes, followed by three on periods of 10 minutes each, with off periods of 10 minutes between each on period.

Typically, the control unit applies each pulse train after a short delay (e.g., between 100 ms and 10 seconds, such as between 100 ms and 2 seconds) after detection of a natural electrical event indicative that a slow wave has occurred in the antrum. Such electrical events may be detected using electrodes 200A and/or 200B, and/or using a separate local sense electrode, as described hereinbelow with reference to FIG. 11. (These detection techniques may be used for all techniques described herein that comprise detecting slow waves.) For some applications, the control unit is configured to have a refractory period (e.g., of 8 to 10 seconds) after application of each pulse train, during which the device does not apply a subsequent pulse train.

For some applications, the control unit is configured to deliver the stimulation during eating, and for a specific time after eating, by the subject. The control unit may be configured to detect such eating, such as using sensors and techniques described hereinbelow with reference to FIG. 11, or to receive an input from the patient manually activating the signal application, for example, upon experiencing a severe symptom, such as nausea. Typically, the control unit is configured to deliver the stimulation for a period having a duration of between 0.5 and 4 hours, beginning after commencement of eating. Alternatively, the control unit is configured to apply the stimulation at certain time(s) of day. This approach obviates the need for an eating detection sensor and its associated lead, and also eliminates the need for patient compliance, and an associated external manual controller device.

Application of an ETC signal at these antral sites has been shown in the above-mentioned article by Sanmiguel et al. to increase gastric emptying in patients. In addition, application of such an ETC signal to the stomach has been shown in the above-mentioned article by Bohdjalian et al. (2006) to increase muscle contraction force.

Alternatively, for some applications both bipolar electrodes 200A and 200B are implanted in the anterior wall of the antrum (configuration not shown). Surgical procedures for implanting electrodes in the anterior wall are generally simpler than those for implanting electrodes on both the anterior and posterior walls of the antrum.

Further alternatively, for some applications, a single bipolar electrode 200 is implanted in the anterior wall of the antrum (configuration not shown). The use of a single bipolar electrode simplifies the surgical implantation procedure and reduces the cost of the procedure.

Still further alternatively, a single bipolar bifurcated lead 202 is used, and one of the electrodes of the bifurcated lead is implanted in the anterior wall of the antrum, and the other electrode in the posterior wall of the antrum (configuration not shown). Use of such a bifurcated lead causes activation of a large portion of the entire antrum using a single lead.

Yet further additionally, two leads 202 are provided, each of which comprises a single unipolar electrode 200, respectively (configuration not shown). One of the electrodes is implanted in the anterior wall of the antrum, and the other electrode is implanted in the posterior wall of the antrum.

Configuration 2

Figure 10A:
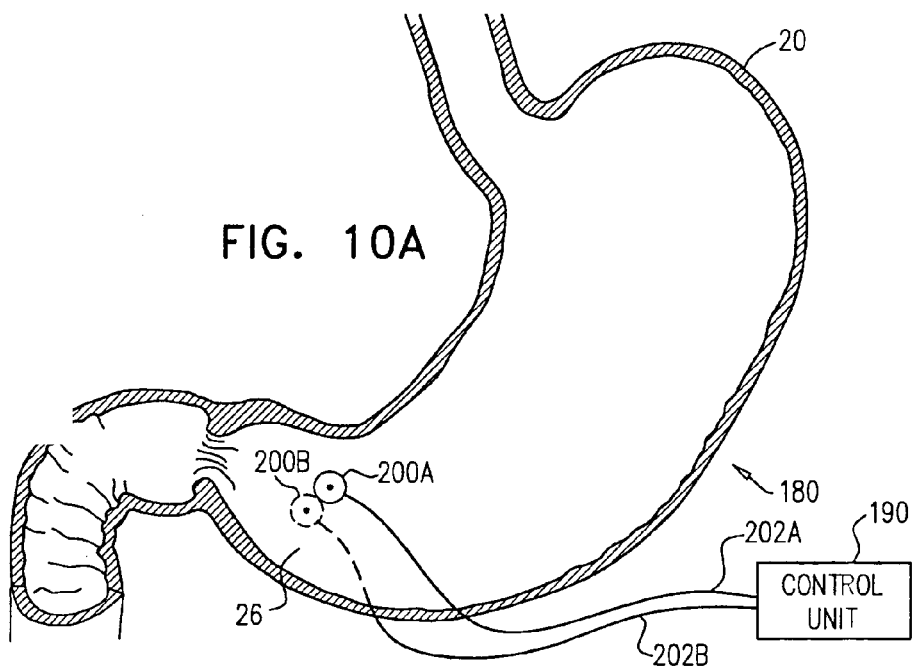
FIGS. 10A-F are schematic illustrations of gastric control apparatus, in accordance with respective applications of the present invention.

Reference is still made to FIG. 10A. In this configuration, control unit 190 is configured to drive electrodes 200A and 200B to apply an excitatory pacing signal to antrum 26. The pacing signal initiates contraction of the muscle of the antrum by generating a propagating action potential in the muscle.

For some applications, the control unit configures the pacing signal with one or more of the following parameters:
  a pulse width of between 50 and 400 ms, such as between 100 and 300 ms; and/or
  an amplitude of between 2 and 20 mA, such as between 2 and 20 mA, such as between 4 and 12 mA.

Alternatively, the pacing signal is delivered as a pulse train, e.g., having pulse durations of 4-6 ms, an amplitude of 1-10 mA, a frequency of 10-40 Hz, modulated on and off with a ratio of 0.5-5 seconds to 4-10 seconds, respectively, an inter-train interval of between 15 and 30 seconds, an inter-pulse interval (between consecutive pulses in the same train) of between 0.1 and 500 ms, such as between 0.25 and 190 ms, and/or as described in the above-mentioned article by Yang et al.

Application of a pacing signal at these antral sites (as well as in the corpus at 10 to 16 cm from the pylorus, along the greater curvature) has been shown in the above-mentioned article by Lin et al. to normalize gastric electrical activity (slow waves), and increase gastric emptying in patients suffering from gastroparesis.

Alternatively, the control unit configures the pacing signal with one or more of the following parameters:
  a pulse train of pulses having a width of between 3 and 10 ms, such as between 4 and 6 ms;
  an amplitude of between 1 and 10 mA;
  a frequency of between 10 and 40 Hz; and/or
  and on/off modulation with a ratio of 0.5 to 5 seconds to 4 to 10 seconds, respectively; for example, the signal may have the parameters specified in the above three bullets, and be applied for a fixed time, such as 0.5 seconds, then not applied for a fixed time, such as 4 seconds.

Application of such a pacing signal at a site 10 cm from the pylorus along the greater curvature of the corpus has been shown in the above-mentioned article by Yang et al. to normalize gastric slow waves.

Configuration 3

Reference is still made to FIG. 10A. In this configuration, control unit 190 is configured to drive electrodes 200A and 200B to apply to antrum 26 an excitatory pacing signal, followed by a non-excitatory signal, such as an ETC signal. The pacing signal initiates contraction of the muscle of the antrum by generating a propagating action potential in the muscle, while the non-excitatory signal modulates, e.g., increases, the contraction of the muscle, while not generating a propagating action potential in the tissue. For example, the control may apply the non-excitatory signal between 0.1 and 5 seconds after applying the pacing signal. The control unit typically uses the parameters described above for applying the non-excitatory signal (Configuration 1) and pacing signal (either of the sets of parameters described above for Configuration 2). Alternatively, separate electrodes are used to apply the pacing and non-excitatory signals.

Application of an ETC signal at these antral sites has been shown in the above-mentioned article by Sanmiguel et al. to increase gastric emptying in patients. Application of a pacing signal at these antral sites has been shown in the above-mentioned article by Lin et al. to normalize gastric electrical activity (slow waves), and increase gastric emptying in patients suffering from gastroparesis. Normalizing the slow waves enables proper timing of the application of the non-excitatory signal for applications in which the non-excitatory signal is applied after a delay from detection of a slow wave, as described hereinabove.

Alternatively, any of the alternative configurations described above for Configuration 1 for configuration and placement of the electrodes may be used.

Configuration 4

Figure 10B:
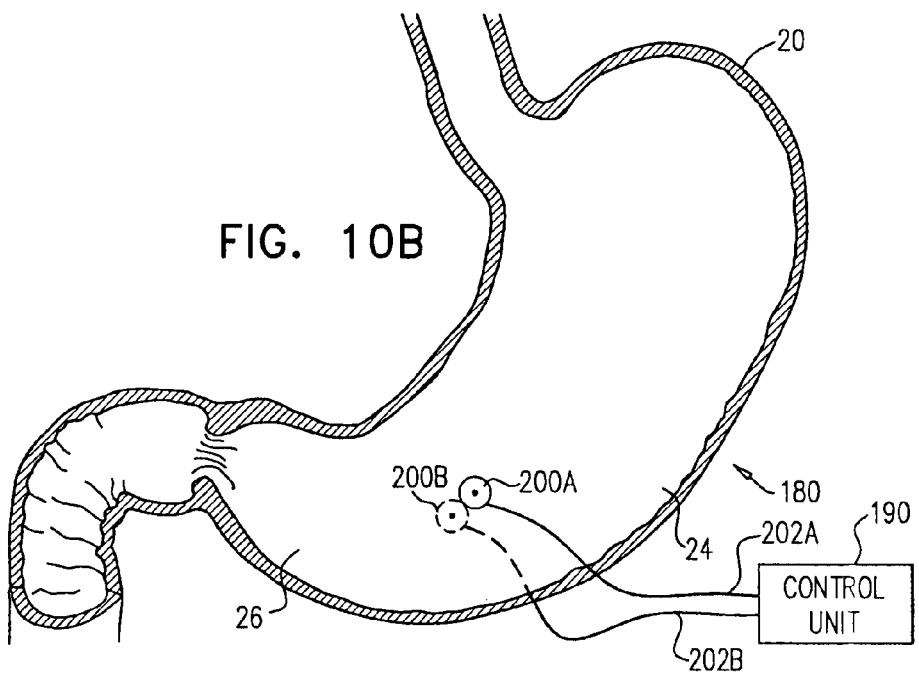

Reference is now made to FIG. 10B. This configuration of apparatus 180 is identical to Configuration 1 described above, except that electrodes 200 are placed on stomach 20 at the border between antrum 26 and a corpus 24. Placement at this location generally stimulates more tissue of stomach 20 than does placement on the antrum.

For some applications, one of the electrodes 200A is placed on an anterior wall of antrum 26, and the other electrode 200B is placed on the posterior wall of the antrum 26. Alternatively, any of the alternative configurations described above for Configuration 1 for configuration and placement of the electrodes may be used, with the electrodes placed at the border between the antrum and the corpus.

Configuration 5

Reference is still made to FIG. 10B. This configuration of apparatus 180 is identical to Configuration 2 described above, except that electrodes 200 are placed on stomach 20 at the border between antrum 26 and corpus 24. Electrical conduction and mechanical contraction usually occur from the corpus to the antrum. Placing the electrodes between the corpus and the antrum may prevent retrograde conduction when pacing in the antrum and elicit a more physiological conduction and contraction response (distal to proximal).

Alternatively, any of the alternative configurations described above for Configuration 2 for configuration and placement of the electrodes may be used.

Configuration 6

Reference is still made to FIG. 10B. This configuration of apparatus 180 is identical to Configuration 3 described above, except that electrodes 200 are placed on stomach 20 at the border between antrum 26 and corpus 24. In addition to the rationale given for Configuration 3 above, this configuration provides a more physiological conduction/contraction flow by being more distal on the stomach.

Alternatively, any of the alternative configurations described above for Configuration 3 for configuration and placement of the electrodes may be used.

Configuration 7

Figure 10C:
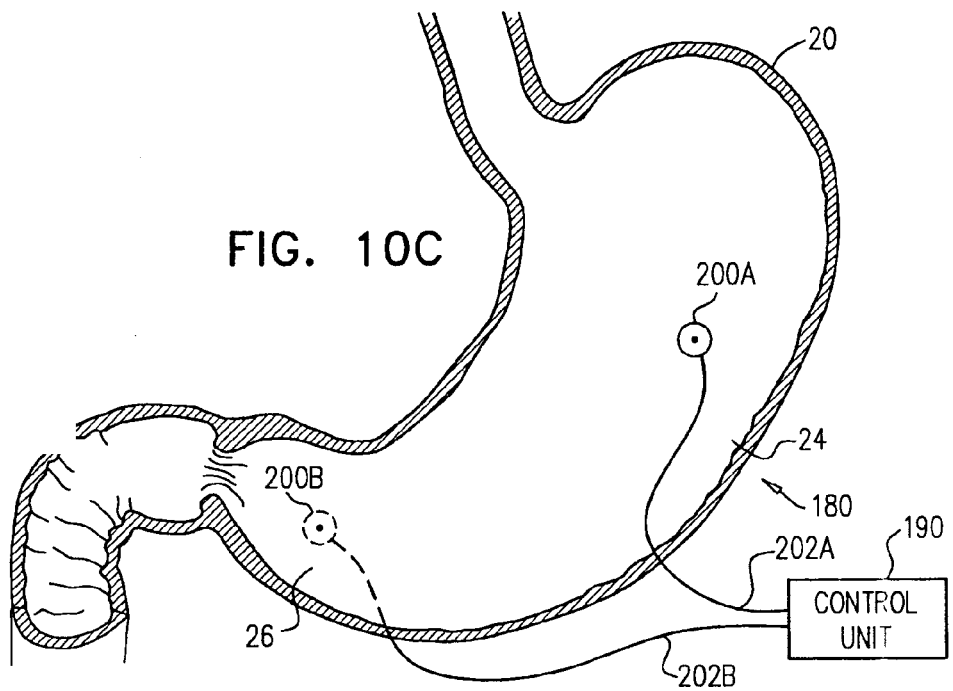

Reference is now made to FIG. 10C. In this configuration of apparatus 180, bipolar electrode 200A is placed at corpus 24 of stomach 20 near the stomach's natural pacemaker, and bipolar electrode 200B is placed at antrum 26 of stomach 20. For some applications, bipolar electrode 200A is placed on the anterior wall of corpus 24, and bipolar electrode 200B is placed on the posterior wall of antrum 26, as shown in the figure. Alternatively, both electrodes are placed on the anterior wall of the stomach, both electrodes are placed on the posterior wall of the stomach, or electrode 200B is placed on the posterior wall of the corpus and electrode 200A is placed on the anterior wall of the antrum.

Control unit 190 is configured to drive electrode 200B to apply an excitatory pacing signal to corpus 24, and to drive electrode 200A to apply a non-excitatory signal to antrum 26, such as an ETC signal. The pacing signal initiates contraction of the muscle of the corpus by generating a propagating action potential in the muscle, while the non-excitatory signal modulates, e.g., increases, the contraction (slow wave) when it arrives in the antrum, while not generating a propagating action potential in the tissue. The control unit typically uses the parameters described above for applying the non-excitatory signal (Configuration 1) and pacing signal (either of the sets of parameters described above for Configuration 2).

For some applications, the control unit is configured to provide a delay between pacing at the corpus and applying the non-excitatory signal to the antrum, in order to allow for conduction of the pacing-triggered slow wave from the corpus to the antrum. Typically, the delay has a duration of at least 10 seconds, such as at least 18 seconds, e.g., between 5 seconds and 25 seconds, such as between 8 seconds and 20 seconds.

Alternatively, the control unit is configured to apply the signal to the antrum after detecting arrival of the slow wave induced by pacing in the corpus. Electrical events associated with the slow wave may be detected using electrodes 200B, and/or using a separate local sense electrode, as described hereinbelow with reference to FIG. 11.

For some applications, the control unit is configured to deliver the stimulation during eating, and for a specific time after eating, by the subject. The control unit may be configured to detect such eating, such as using sensors and techniques described hereinbelow with reference to FIG. 11, or to receive an input from the patient manually activating the signal application, for example, upon experiencing a severe symptom, such as nausea. Typically, the control unit is configured to deliver the stimulation for between 0.5 and 4 hours after commencement of eating. Alternatively, the control unit is configured to apply the stimulation at certain time(s) of day.

This approach obviates the need for an eating detection sensor and its associated lead, and also eliminates the need for patient compliance, and an associated external manual controller device.

Pacing in the corpus near the site of the stomach's natural pacemaker has been shown in the above-mentioned article by Lin et al. to normalize slow waves and slow wave propagation in patients suffering from gastroparesis. Application of an ETC signal in the antrum has been shown in the above-mentioned articles by Bohdjalian et al. (2006 and 2009) to increase gastric contractility and strengthen contractions. In addition, application of an ETC signal in the antrum has been shown in the above-mentioned article by Sanmiguel et al. to increase gastric emptying in patients. Normalizing the slow waves enables proper timing of the application of the non-excitatory signal after a delay from initiation of a slow wave in the corpus.

Alternatively, lead 202B is bifurcated, and one of the electrodes of the bifurcated lead is implanted in the anterior wall of the antrum, and the other electrode in the posterior wall of the antrum (configuration not shown). Alternatively or additionally, lead 202A is bifurcated, and one of the electrodes of the bifurcated lead is implanted in the anterior wall of the corpus, and the other electrode in the posterior wall of the corpus (configuration not shown). Use of such bifurcated leads causes activation of a large portion of the entire antrum or corpus using a single lead.

Further alternatively, a set of two bipolar electrodes 200B are placed on antrum 26, such that one of the bipolar electrodes is implanted on the anterior wall of the antrum, and the other bipolar electrode is implanted on the posterior wall of the antrum. Alternatively or additionally, a set of two bipolar electrodes 200A are placed on corpus 24, such that one of the bipolar electrodes is implanted on the anterior wall of the corpus, and the other bipolar electrode is implanted on the posterior wall of the corpus.

Figure 10D:
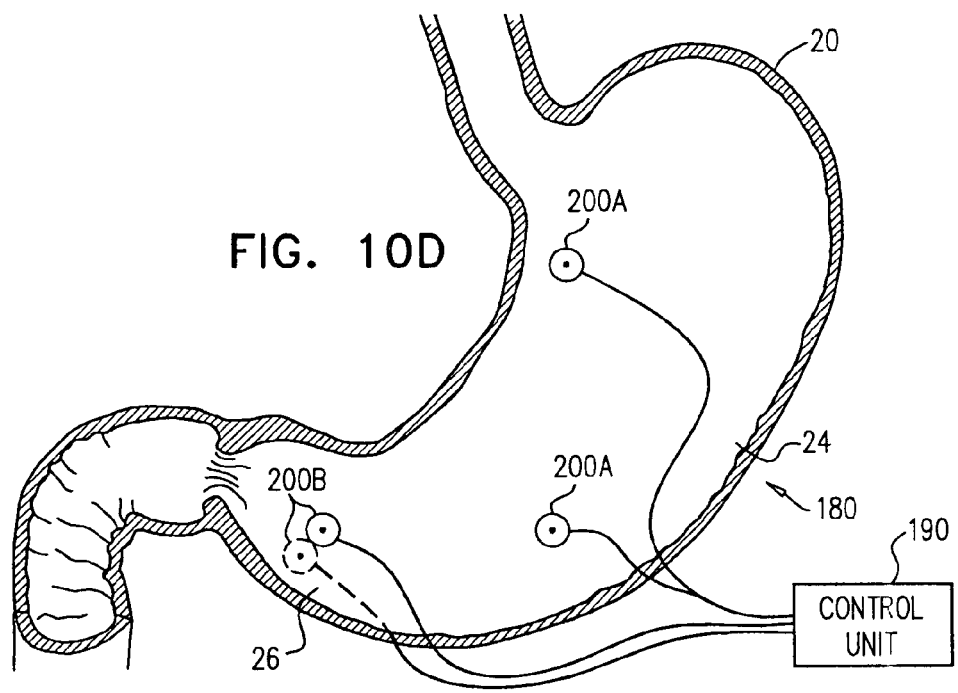

Alternatively or additionally, a set of two bipolar electrodes 200A are placed on corpus 24, such that one of the bipolar electrodes is implanted on the lesser curvature of the corpus, and the other electrode along the greater curvature of the corpus (such as shown in FIG. 10D). Stimulation with this placement generally causes activation of a large portion of the corpus. Also, the vagus nerve innervation of the stomach is concentrated at a location in the lesser curvature, such that vagus stimulation in this area may help control obesity.

Alternatively, any of the alternative configurations described above for Configuration 2 for configuration and placement of the electrodes may be used.

Configuration 8

Reference is still made to FIG. 10C. In this configuration, bipolar electrode 200A is placed at corpus 24 of stomach 20 near the stomach's natural pacemaker, and bipolar electrode 200B is placed at antrum 26 of stomach 20, such as described above for Configuration 7.

Control unit 190 is configured to drive bipolar electrode 200B to apply an excitatory pacing signal to corpus 24, followed by a non-excitatory signal, such as an ETC signal. The pacing signal initiates contraction of the muscle of the corpus by generating a propagating action potential in the muscle, while the non-excitatory signal modulates, e.g., increases, the contraction of the muscle, while not generating a propagating action potential in the tissue. For example, the control may apply the non-excitatory signal between 0.1 and 5 seconds after applying the pacing signal. The control unit typically uses the parameters described above for applying the non-excitatory signal (Configuration 1) and pacing signal (either of the sets of parameters described above for Configuration 2).

For some applications, in addition to applying the excitatory and non-excitatory signals to the corpus, control unit 190 drives bipolar electrode 200A to apply an excitatory pacing signal to antrum 26, followed by a non-excitatory signal, such as an ETC signal. The pacing signal initiates contraction of the muscle of the antrum by generating a propagating action potential in the muscle, while the non-excitatory signal modulates, e.g., increases, the contraction of the muscle, while not generating a propagating action potential in the tissue. For example, the control may apply the non-excitatory signal between 0.1 and 5 seconds after applying the pacing signal. The control unit typically uses the parameters described above for applying the non-excitatory signal (Configuration 1) and pacing signal (either of the sets of parameters described above for Configuration 2).

Alternatively, for some applications, after applying the excitatory and non-excitatory signals to the corpus, control unit 190 drives bipolar electrode 200A to apply a non-excitatory signal to antrum 26, such as an ETC signal. The non-excitatory signal modulates, e.g., increases, the contraction (slow wave) when it arrives in the antrum, while not generating a propagating action potential in the tissue. The control unit typically uses the parameters described above for applying the non-excitatory signal (Configuration 1).

In addition, for some applications, the control unit is configured to provide a delay between pacing at the corpus and pacing (or application of the non-excitatory signal, in the case of the alternative applications) at the antrum, in order to allow for conduction of the pacing-triggered slow wave from the corpus to the antrum. Typically, the delay has a duration of at least 10 seconds, such as at least 15 seconds, e.g., between 5 seconds and 25 seconds, such as between 8 seconds and 20 seconds. Alternatively, the control unit is configured to simultaneously or nearly simultaneously (i.e., within 1 second of commencement of applying the excitatory signal to the corpus) drive the pacing at the corpus and the pacing (or application of the non-excitatory signal, in the case of the alternative applications) at the antrum.

For some applications, the control unit is configured to deliver the stimulation during eating, and for a specific time after eating, by the subject. The control unit may be configured to detect such eating, such as using sensors and techniques described hereinbelow with reference to FIG. 11, or to receive an input from the patient manually activating the signal application, for example, upon experiencing a severe symptom, such as nausea. Typically, the control unit is configured to deliver the stimulation for between 0.5 and 4 hours after commencement of eating. Alternatively, the control unit is configured to apply the stimulation at certain time(s) of day. This approach obviates the need for an eating detection sensor and its associated lead, and also eliminates the need for patient compliance, and an associated external manual controller device.

Neural stimulation has been shown in the above-mentioned article by van der Voort et al. to relieve symptoms of nausea and vomiting in gastroparesis patients.

Alternatively, lead 202B is bifurcated, and one of the electrodes of the bifurcated lead is implanted in the anterior wall of the antrum, and the other electrode in the posterior wall of the antrum (configuration not shown). Alternatively or additionally, lead 202A is bifurcated, and one of the electrodes of the bifurcated lead is implanted in the anterior wall of the corpus, and the other electrode in the posterior wall of the corpus (configuration not shown). Use of such bifurcated leads causes activation of a large portion of the entire antrum or corpus using a single lead.

Further alternatively, a set of two bipolar electrodes 200B are placed on antrum 26, such that one of the bipolar electrodes is implanted on the anterior wall of the antrum, and the other bipolar electrode is implanted on the posterior wall of the antrum. Alternatively or additionally, a set of two bipolar electrodes 200A are placed on corpus 24, such that one of the bipolar electrodes is implanted on the anterior wall of the corpus, and the other bipolar electrode is implanted on the posterior wall of the corpus.

Alternatively or additionally, a set of two bipolar electrodes 200A are placed on corpus 24, such that one of the bipolar electrodes is implanted on the lesser curvature of the corpus, and the other electrode along the greater curvature of the corpus (such as shown in FIG. 10D). Stimulation with this electrode placement generally causes activation of a large portion of the corpus. Also, the vagus nerve innervation of the stomach is concentrated at in the lesser curvature, such that vagus stimulation in this area may help control obesity.

Alternatively, any of the alternative configurations described above for Configuration 2 for configuration and placement of the electrodes may be used.

Configuration 9

This configuration is identical to Configuration 3, except that electrodes are placed on the corpus of the stomach, and control unit 190 is configured to drive the electrodes to apply to the corpus an excitatory pacing signal, followed by a non-excitatory signal, such as an ETC signal. The pacing signal initiates contraction of the muscle of the corpus by generating a propagating action potential in the muscle, while the non-excitatory signal modulates, e.g., increases, the contraction of the muscle, while not generating a propagating action potential in the tissue. For example, the control may apply the non-excitatory signal between 0.1 and 5 seconds after applying the pacing signal. The control unit typically uses the parameters described above for applying the non-excitatory signal (Configuration 1) and pacing signal (either of the sets of parameters described above for Configuration 2).

Alternatively, control unit 190 is configured to drive the electrodes to apply the non-excitatory signal, such as the ETC signal, to the corpus, without also applying the pacing signal to the corpus. For some applications, the control unit applies the signal after a delay from a sensed slow wave in the corpus or antrum, as described hereinbelow in Configuration 14.

Application of the non-excitatory signal to the corpus, with or without the pacing signal, modulates the force the region produces, and improves the electro-mechanical coupling in the corpus.

Alternatively, any of the alternative configurations described above for Configuration 1 for configuration and placement of the electrodes may be used.

Configuration 10

Reference is now made to FIG. 10D. In this configuration, two bipolar electrodes 200B are applied to the anterior and posterior walls of antrum 26, as in Configuration 1. In addition, two bipolar electrodes 200A are applied to corpus 24, such that one of the bipolar electrodes is implanted on the lesser curvature of the corpus, and the other electrode along the greater curvature of the corpus. Stimulation with this placement generally causes activation of a large portion of the corpus. For some applications, the two bipolar electrodes are placed on the corpus between 8 and 10 cm apart from each other. The bipolar electrode along the lesser curvature of the corpus may be placed between 8 and 10 cm from the closest electrode in the antrum, and the electrode along the greater curvature of the corpus may be placed between 10 and 13 cm from the closest electrode in the antrum. Alternatively or additionally, the antrum electrodes are placed on the border between the corpus and antrum, such as shown in FIG. 10B.

Configuration 11

Figure 10E:
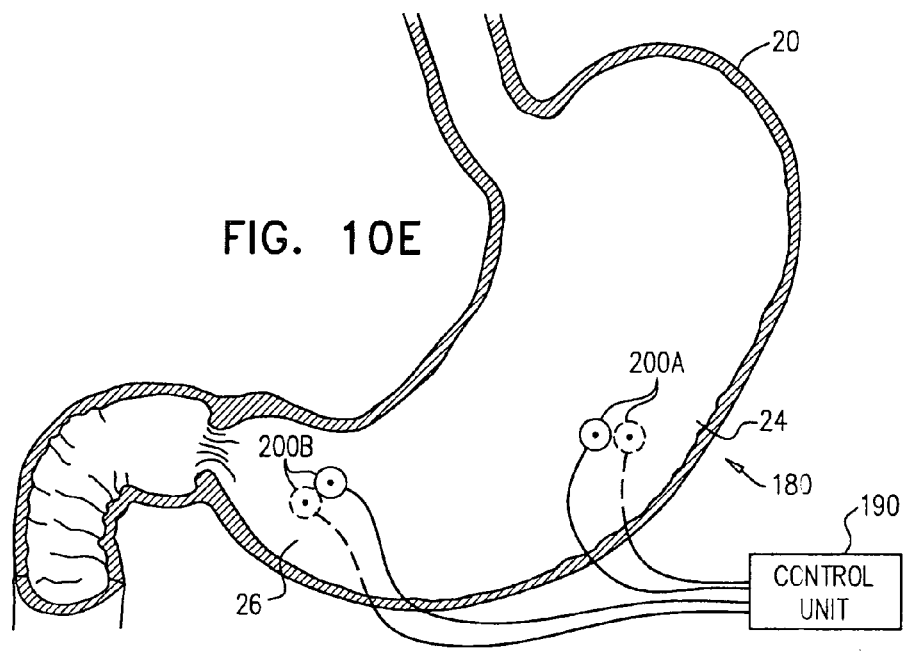

Reference is now made to FIG. 10E. This configuration is similar to that of Configuration 7 (shown in FIG. 10C), except that two bipolar electrodes 200B are applied to the anterior and posterior walls of antrum 26, as in Configuration 1, and two bipolar electrodes 200A are applied to the anterior and posterior walls of corpus 24, typically along the greater curvature of the corpus. Alternatively or additionally, the antrum electrodes are placed on the border between the corpus and antrum, such as shown in FIG. 10B.

Configuration 12

Figure 10F:
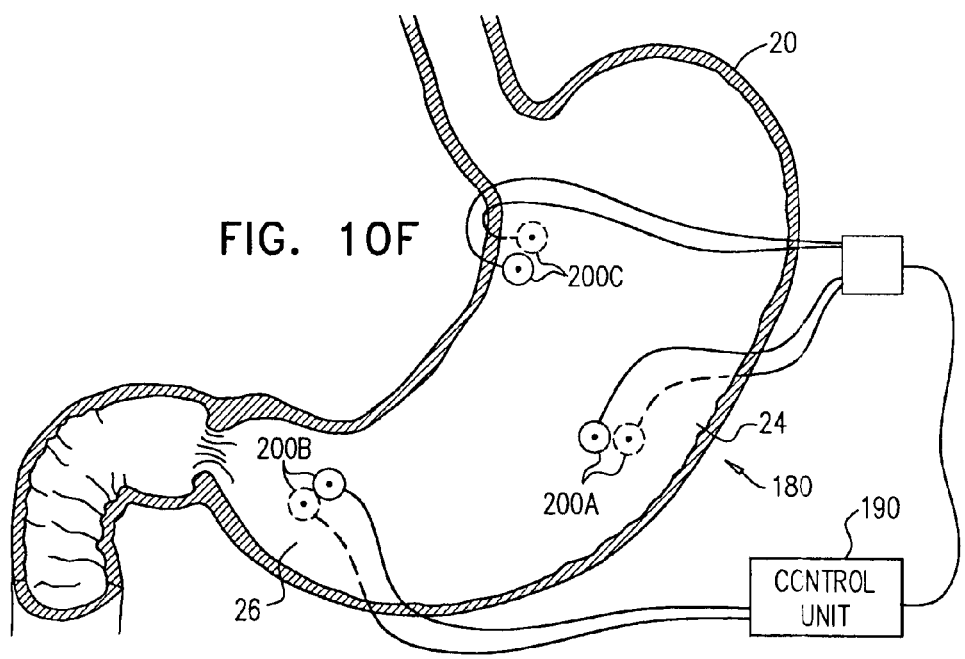

Reference is now made to FIG. 10F. This configuration is similar to that of Configuration 11 (shown in FIG. 10E), except that in addition, two bipolar electrodes 200C are applied to the anterior and posterior walls of corpus 24 along the less curvature of the corpus. Alternatively or additionally, the antrum electrodes are placed on the border between the corpus and antrum, such as shown in FIG. 10B.

Configuration 13

In this configuration, the techniques of Configurations 7, 8, 9, 10, 11, or 12 are used, except as follows. The control unit is configured to deliver the stimulation during eating, and for a specific time after eating, by the subject. The control unit may be configured to detect such eating, such as using sensors and techniques described hereinbelow with reference to FIG. 11, or to receive an input from the patient manually activating the signal application, for example, upon experiencing a severe symptom, such as nausea. Typically, the control unit is configured to deliver the stimulation for between 0.5 and 4 hours after commencement of eating. Alternatively, the control unit is configured to apply the stimulation at certain time(s) of day.

At other times, control unit 190 is configured drive one or more electrodes to apply a neural modulation signal to corpus 24, such as to the lesser curvature of the corpus, or near the natural pacemaker site (10 cm from pylorus along greater curvature at the Musularis Propia. Typically, the signal is applied with pulses having a duration of 200-400 microseconds (e.g., 300 microseconds), an amplitude of 2 to 8 mA, a frequency of 10 to 20 Hz, and modulated on and off with a ratio of between 0.5 and 3 seconds to between 2 and 7 seconds, respectively. Such stimulation is believed to cause afferent activation of the vagus nerve, and to treat symptoms of gastroparesis, such as nausea, dizziness, and/or vomiting. Alternatively, the neural modulation signal is applied at substantially all times (including during eating), at pre-defined times (regardless of eating, or only not during eating), or on-demand by the patient.

Neural stimulation has been shown in the above-mentioned article by van der Voort et al. to relieve symptoms of nausea and vomiting in gastroparesis patients.

Alternatively, during eating, the control unit is configured to apply the signals described above as being applied to the antrum (Configurations 1-6), rather than applying signals to the corpus.

Configuration 14

Reference is again made to FIGS. 10C-F. In this configuration, the techniques of Configuration 7, 8, 9, 10, 11, or 12 are used, except that control unit 190 is configured to drive bipolar electrode 200A to apply a non-excitatory signal, such as an ETC signal, to corpus 24, and bipolar electrode 200B to apply a non-excitatory signal to antrum 26. The control unit typically uses the parameters described above for applying the non-excitatory signal (Configuration 1). In this configuration, the control unit does not drive the electrodes to apply a pacing signal to either the corpus or the antrum.

For some applications, the control unit is configured to apply the non-excitatory signal to the corpus after a delay after sensing a slow wave. The delay may be measured:
from the sensing of a slow wave in the corpus, in which case the delay may be between 0.1 and 10 seconds, such as between 1 and 2 seconds, for example; or
from the sensing of a slow wave in the antrum, in which case the delay may be between 8 and 13 seconds, such as between 9 and 11 seconds, e.g., 10 seconds; this technique may be particularly appropriate when slow waves are not present and/or not detectable in the corpus.

For some applications, simultaneously, or nearly simultaneously (i.e., within 1 second of commencement of applying the non-excitatory signal to the corpus), control unit 190 drives bipolar electrode 200B to apply a non-excitatory signal, such as an ETC signal, to antrum 26.

Alternatively, control unit 190 drives bipolar electrode 200B to apply the non-excitatory signal to antrum 26 at a later time than the application of the non-excitatory signal to corpus 24. The timing of the application of the signal to the antrum may be performed by:
sensing the slow wave in the corpus, and waiting a delay, such as between 8 and 13 seconds, e.g., between 9 and 11 seconds, such as 10 seconds (slows waves typically travel at a velocity of 1-1.5 cm/second in the stomach); or
sensing the slow wave in the antrum, and waiting a delay, such as between 1 and 2 seconds.

For some applications, control unit 190 is configured to attempt to detect slow waves in the corpus. If such slow waves are present and detectable, the control unit times the application of the non-excitatory signal to the corpus (and, optionally, to the antrum) based on delay(s) after the detection of the slow waves in the corpus. If such slow waves are not detectable, the control unit times the application of the non-excitatory signals to the corpus and the antrum based on respective delays after the detection of slow waves in the antrum. The inventors believe that in patients suffering from untreated gastroparesis, slows waves are sometimes not present or detectable in the corpus. However, after long-term treatment with the techniques described herein, such slow waves may become detectable in the corpus, as electromechanical coupling improves in the stomach muscle tissue (such as described hereinbelow with reference to FIGS. 13A-B). The control unit is thus configured to time the application of the non-excitatory stimulation in the corpus based on slows waves detected in the antrum if necessary, but to prefer to base the timing on slow waves detected in the corpus when available. A delay from slow waves in the corpus is believed to provide more precise timing for the application of the signal to the corpus.

Such stimulation enhances contraction in both the antrum and corpus, but at different phases of the refractory period. This may emulate normal conduction and contraction cycles.

Alternatively, any of the alternative configurations described above for Configuration 7 for configuration and placement of the electrodes may be used, mutatis mutandis because no pacing is applied.

Configuration 15

Reference is again made to FIG. 10C. In yet another configuration, control unit 190 is configured to apply a pacing signal to corpus 24 regularly, such as once every 15 to 20 seconds. Control unit 190 is configured to sense slow waves in antrum 26 until the slow waves are normalized to the pacing in the corpus. Upon detecting such normalization, which generally occurs about 10 to 20 seconds, for example, after pacing in the corpus, control unit 190 continues to pace in the corpus, and additionally drives the electrodes to apply a non-excitatory signal, such as an ETC signal, to the antrum and the corpus simultaneously or nearly simultaneously (i.e., within 1 second of each other), after a delay from application of the pacing signal, having, for example, a duration of between 0.1 and 5 seconds. Alternatively, the control unit applies the non-excitatory signals to the corpus and antrum non-simultaneously, such as between 2 and 15 seconds apart, such as between 5 and 10 seconds apart.

For some applications, the techniques described herein for applying signals to, and sensing at, the corpus and antrum of the stomach are used to apply the signals described hereinabove to, and sense at, a first, more proximal site of the stomach, and a second, more distal site of the stomach, which is typically at least 3 cm from the first proximal site, such as at least 5 cm, 8 cm, 10 cm, 15 cm, or 20 cm from the first proximal site. The signals described hereinabove as being applied to the corpus are applied to the first proximal site of the stomach, and the signals described hereinabove as being applied to the antrum are applied to the second distal site of the stomach. Similarly, the sensing described hereinabove as being performed at the corpus is performed at the first proximal site, and the sensing described hereinabove as being performed at the antrum is performed at the second distal site. For example, both the first and second sites may be on the corpus, or both the first and second sites may be on the antrum. Alternatively, one or both of the first and second sites may be elsewhere on the GI tract, such as the fundus of the stomach, the esophagus, the esophageal sphincter, the pyloric sphincter, the duodenum, the small intestine, or the colon. In this case, the second distal site is typically at least 3 cm from the first proximal site, such as at least 5 cm, 8 cm, 10 cm, 15 cm, or 20 cm, 50 cm, 70 cm, 100 cm, 300 cm, 500 cm, or 1000 cm from the first proximal site. For some applications, the control unit is configured to apply the non-excitatory signal at a plurality of sites with a delay between application at the sites. In addition, the control unit may be configured to fence for inhibiting arrhythmia.

For some applications, the techniques described herein are applied to more than two longitudinal sites of the GI tract, such as to three, four, or more sites.

Figure 11:
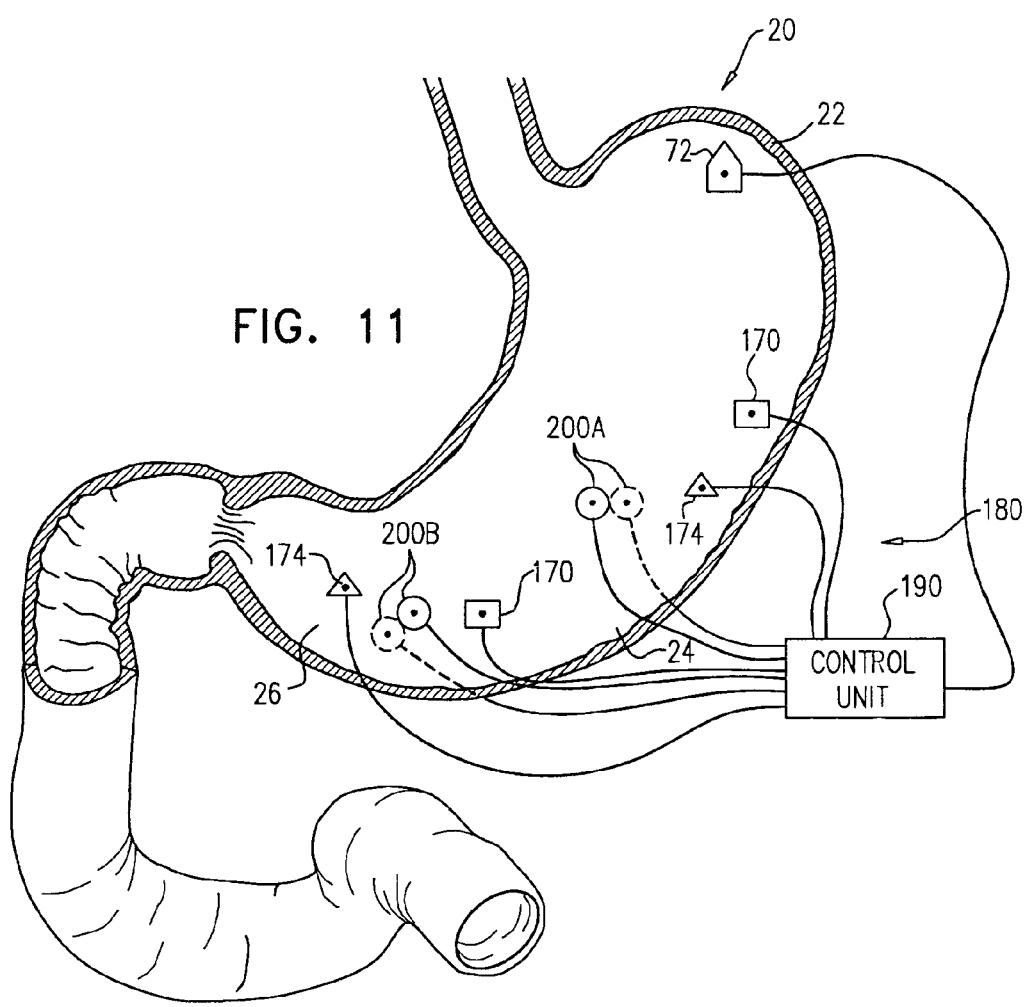
FIG. 11 is a schematic illustration the gastric control apparatus of FIGS. 10A-F comprising additional electrodes and sensors, in accordance with an application of the present invention.

Reference is made to FIG. 11, which is a schematic illustration gastric control apparatus 180 comprising additional electrodes and sensors, in accordance with an application of the present invention. Although the configuration of electrodes 200A and 200B is shown as in FIG. 10E, the configurations shown in FIGS. 10A-D and 10F, and described hereinabove, may also be used. As mentioned above, electrodes 200 function as signal-application electrodes. For some applications, electrodes 200 may also operate in a sensing mode. In addition, one or more dedicated local sense electrodes 174 may also be placed on or in stomach 20, and convey electrical signals to control unit 190 responsive to natural gastric electric activity, such as for detecting slow waves, as described hereinabove. In addition, one or more mechanical sensors 170 (e.g., accelerometers, force transducers, strain gauges, or pressure gauges) may be coupled to the control unit and are placed on or in the stomach. Alternatively or additionally, one or more supplemental sensors 172 (e.g., pH sensors, blood sugar sensors, intragastric pressure sensors and/or sonometric sensors) may be coupled to the control unit and are placed on or in the gastrointestinal tract or elsewhere on or in the patient's body. The control unit may modify the waveform applied through electrodes 200 responsive to signals from sensors 170 and 172 and local sense electrodes 174, as described hereinbelow with reference to FIG. 12. Typically, control unit 190 and the above-mentioned electrodes and sensors are permanently or semi-permanently implanted in or coupled to the patient's body.

Techniques for detecting eating may be used that are described in U.S. Pat. No. 7,437,195, U.S. Pat. No. 7,330,753, US Patent Application Publication 2009/0118797, US Patent Application Publication 2009/0281449, and/or PCT Publication WO 08/117,296, all of which are incorporated herein by reference. For some applications, techniques described herein as detecting eating detect any eating (i.e., either solids or liquids), while for other applications, the control unit only applies the signals upon detecting eating of solid foods, such as using the techniques described in these applications incorporated herein by reference.

Figure 12:
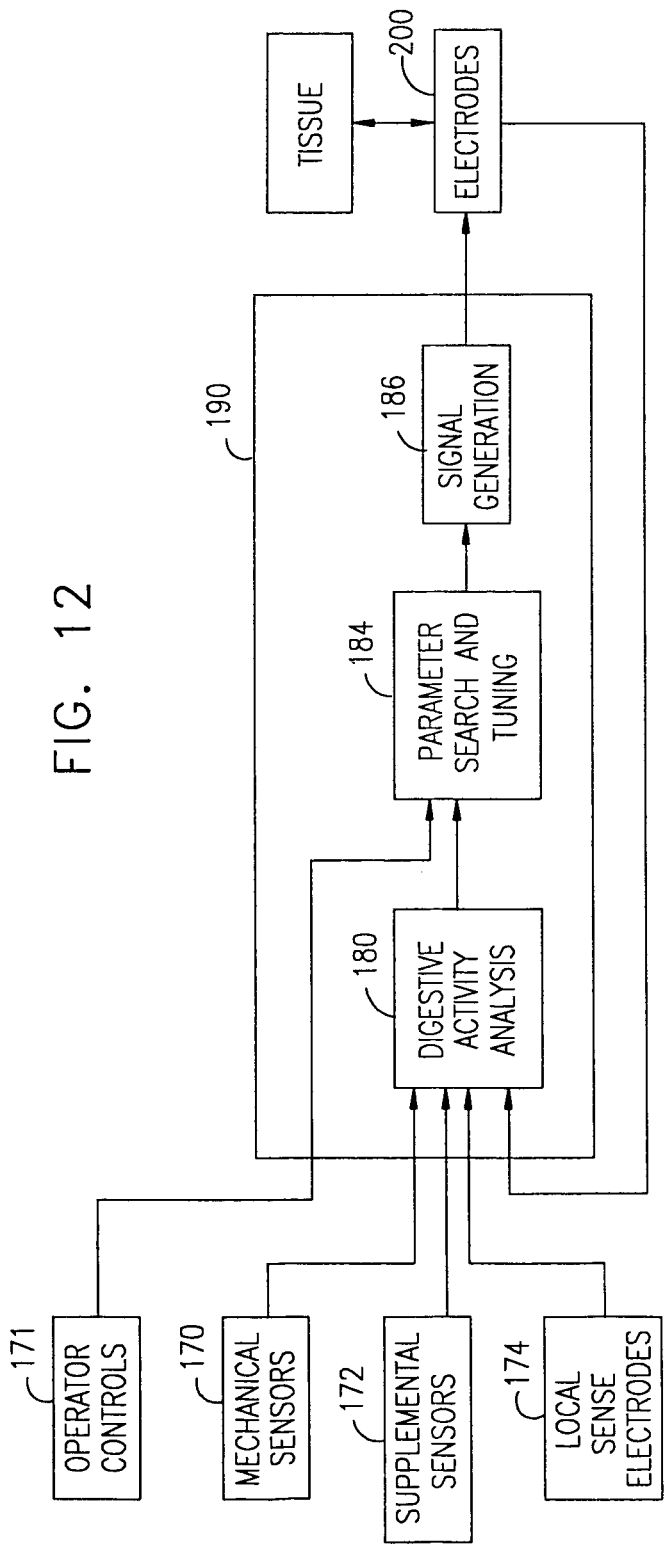
FIG. 12 is a schematic block diagram of a control unit of the gastric control apparatus of FIGS. 10A-F and 11, in accordance with an application of the present invention.

FIG. 12 is a schematic block diagram of control unit 190, in accordance with an application of the present invention. Mechanical sensors 170, supplemental sensors 172, local sense electrodes 174, and electrodes 200 may be coupled to provide feedback signals to a digestive activity analysis block 180 of control unit 190. The feedback signals generally provide block 180 with information about various aspects of the stomach's present state (e.g., empty or full) and the stomach's level of activity, so as to enable block 180 to analyze the signals and actuate control unit 190 to modify the electrical energy applied to electrodes 200 responsive to the analysis. For some applications, the enhancement signal is adjusted by the control unit responsive to the feedback signals in order to yield a desired response, e.g., an indication by mechanical sensors 170 of a desired level of muscle contraction within portion 22, or an indication by supplemental sensors 172 of maintenance of the patient's blood sugar level within a desired range.

As shown in FIG. 12, digestive activity analysis block 180 typically conveys results of its analysis of the inputs from mechanical sensors 170, supplemental sensors 172, and electrodes 200 to a "parameter search and tuning" block 184 of control unit 190, which iteratively modifies characteristics of the electrical energy applied to stomach 20 in order to attain a desired response. For some applications, operating parameters of block 184 are entered, using operator controls 171, by a physician or other human operator of the control unit. Block 184 typically utilizes multivariate optimization and control methods known in the art in order to cause one or more of the aforementioned mechanical, electrical, chemical and/or other measured parameters to converge to desired values.

In general, each one of electrodes 200 may convey a particular waveform to stomach 20, differing in certain aspects from the waveforms applied by the other electrodes. The particular waveform to be applied by each electrode is determined by control unit 190, typically under the initial control of the operator. Aspects of the waveforms which are set by the control unit, and may differ from electrode to electrode, typically include parameters such as time shifts between application of waveforms at different electrodes, waveform shapes, amplitudes, DC offsets, durations, and duty cycles. For example, although the waveforms applied to some or all of electrodes 200 usually comprise a train of biphasic square waves following a natural or applied pacing pulse, other waveforms, such as a sinusoid, one or more monophasic square waves, or a waveform including an exponentially-varying characteristic, could be applied to other electrodes. Generally, the shape, magnitude, and timing of the waveforms are optimized for each patient, using suitable optimization algorithms as are known in the art.

Typically, desired signal parameters are conveyed by block 184 to a signal generation block 186 of control unit 190, which generates, responsive to the parameters, electrical signals that are applied by electrodes 200 to the stomach. Block 186 typically comprises amplifiers, isolation units, and other standard circuitry known in the art of electrical signal generation.

In an initial calibration procedure, parameter search and tuning block 184 typically modifies a characteristic (e.g., timing, magnitude, or shape) of the enhancement signal applied through one of electrodes 200, and then determines whether a predetermined response generally improves following the modification. For example, one or more of mechanical sensors 170 may be used to determine the extent to which the shape of stomach 20 changes responsive to corresponding changes in the applied enhancement signal. In a series of similar calibration steps, block 184 repeatedly modifies characteristics of the energy applied through each of the electrodes, such that those modifications that improve the response are generally maintained, and modifications that cause it to worsen are typically eliminated or avoided. For some applications, the calibration procedure is subsequently performed by the physician at intermittent follow-up visits, and/or by unit 190 automatically during regular use of apparatus 180 (e.g., daily).

For some applications, during the initial calibration procedure, the locations of one or more of electrodes 200 are varied while the enhancement signal is applied therethrough, so as to determine optimum placement of the electrodes. In a series of calibration steps, each electrode is moved over an area of stomach 20, and an appropriate response of the stomach is measured. After the physician considers that a sufficient number of sites have been investigated to characterize the area, the electrode is returned to the site yielding the best response. Subsequently, other electrodes, placed on, in, or near the stomach are moved according to the same protocol, so as to achieve substantially optimum placement of some or all of the electrodes.

Based on results of the calibration procedure and/or an analysis of other factors pertaining to the patient's condition, the physician typically determines whether the ETC signal should be applied subsequent to an artificial pacing pulse or in response to natural electrical activity of the stomach. In the former case, the ETC signal may be applied in a vicinity of a site where standard gastric pacing pulses are applied. Optionally, the ETC signal is applied through the same electrode as that through which a gastric pacing pulse is applied.

Alternatively, stomach 20 generates the gastric rhythm, substantially without artificial pacing. In such modes, local sense electrodes 174 and, optionally, some or all of electrodes 200, convey electrical signals to control unit 190, so as to enable parameter search and tuning block 184 to synchronize the electrical signals applied by electrodes 200 with the natural electrical activity of the stomach. It will be understood that although electrodes 174 and 200 are shown for clarity of explanation as separate entities, a single set of electrodes may be used to perform both functions.

Reference is now made to FIGS. 13A and 13B, which are graphs showing experimental results measured in accordance with an application of the present invention. The experiment was performed on a single human diabetic patient (who did not suffer from gastroparesis). Two sets of electrodes were implanted on the stomach, one set on the anterior wall of the antrum, and the second set on the posterior wall of the antrum. A control unit similar to control unit 190 was implanted in the patient, and configured to apply non-excitatory ETC stimulation to the antrum after a delay of between 100 ms and 4 seconds after detection of each slow wave. Each of the signals had a duration of 1200 ms, and an amplitude of between 10 to 13 mA (with a constant voltage). The signals were applied in response to respective detected eating events. The stimulation was applied for 20 weeks.

FIG. 13A shows a baseline local sense signal (top graph), and a baseline impedance signal (bottom graph), both measured at the beginning of the experiment. FIG. 13B shows the local sense signal and impedance signal measured after 20 weeks of treatment with non-excitatory stimulation during the experiment. Each of the vertical lines in the local sense signals represent a detected slow wave, among which are interspersed occasional spikes. The deflections in the impedance signals represent detected local muscle contractions, which occur corresponding to spikes in the local sense signal.

As can be seen, the ratio of spikes to slow waves is greater in the local sense signal shown in FIG. 13B than in the local sense signal shown in FIG. 13A, which results in a greater portion of the slow waves causing mechanical contractions in FIG. 13B and than in FIG. 13A. The inventors hypothesize that this improvement is caused by greater electromechanical coupling caused by the long-term treatment with the device. The inventors further hypothesize that the stomach muscles of patients suffering from gastroparesis are characterized by disorganized cellular coupling, and that long-term treatment with the device improves this gastric coupling.

In an application of the present invention, a method is provided that comprises identifying that a patient suffers from suboptimal electromechanical coupling in stomach muscle tissue, for example by diagnosing the patient suffers from gastroparesis. Such identifying may be performed by measuring electrical signals of the patient's stomach, or by using conventional techniques for diagnosing gastroparesis (such as measuring the rate of gastric emptying and/or evaluating other symptoms of gastroparesis, as is known the medical art). The method further comprises, in response to the identifying, improving the electromechanical coupling by applying a non-excitatory signal, such as an ETC signal, to the patient's stomach (such as to the corpus and/or the antrum, e.g., using techniques described hereinabove) at least intermittently during a period having a duration of at least 12 weeks, such as at least 24 weeks. For example, the stimulation may be applied for at least 150 minutes during each day of the period.

For some applications, control unit 190 configures the applied signals to slow the speed of digestion and/or gastric emptying, by controlling the phasing of the stimulation. The control unit may be configured to modulate (increase or decrease) the amplitude of contractions.

For some applications, the stimulation techniques described herein are applied to, or applied in combination with stimulation of, a non-gastric portion of the gastrointestinal tract, such as the colon, bowel, small intestine (e.g., duodenum), esophagus, esophageal sphincter, and pyloric sphincter.

For some applications, the techniques described herein are used to treat one or more of the following disorders:

Gastroparesis
Diabetes (type 2 or type 1)
Obesity
Gastro-esophageal reflux disease (GERD)
Tachygastrias
Intestinal pseudo-obstruction
Nausea and/or vomiting (e.g., caused by pregnancy or chemotherapy), such as drug-induced nausea (e.g., chemotherapy, antibiotics, anti-depressants)
Functional dyspepsia-dysmotility type with normal gastric emptying
Gastric ulcers (acute) with nausea Post-operative conditions
Eating disorders (e.g., anorexia nervosa, bulimia nervosa)
Premature infants
Drug-induced conditions (glucagon, epinephrine, morphine sulfate)
Functional (idiopathic) dyspepsia with delayed gastric emptying
Tachyarrhythmias (mix of tachygastrias and bradygastrias)
Motion sickness
Bradygastrias
Drug induced-epinephrine
Arrhythmias
Hyperemesis gravidarum
Drug induced epinephrine
Short bowel syndrome
Idiopathic diarrhea
Irritable bowel syndrome
Constipation For some applications, apparatus 180 comprises a rechargeable battery, because applying pacing or non-excitatory signals to the smooth muscles of the stomach and GI tract requires substantial amount of energy, usually not well supported by commonly available implantable nerves or cardiac pacemakers. The rechargeable battery supports the energy needs of chronic signal delivery by the apparatus 180. Typically, the apparatus comprises energy-receiving circuitry to enable wireless recharging of the battery (e.g., by induction or RF), without the need for wires to cross the skin, and without the need to frequently replace the implantable device because of battery depletion.

For some applications, some or all of the techniques described hereinabove with reference to FIGS. 10A-13B regarding apparatus 180 may be implemented in combination with some or all of the techniques described hereinabove with reference to FIGS. 1-9B regarding apparatus 18. Such a combination of techniques may be beneficial, for example, for treating a patient who suffers from both gastroparesis and one or more of the conditions described hereinabove with reference to apparatus 18 (such as diabetes). For some applications, the functionalities of apparatus 180 and 18 are integrated in a single device (e.g., comprising a single control unit), which is configured to apply two therapies (e.g., using the same electrode set(s) at a single site, or a plurality of sites). For other applications, separate apparatus 180 and 18 are provided, as two separate devices, which optionally communicate with each other, such as in order to coordinate one or more aspects of the therapies (e.g., a timing of the application of the separate electrical signals). Alternatively, the devices share a common control unit, but use separate electrode set(s).

For some applications, when the techniques described herein are used to treat a particular condition, methods of practicing the techniques comprise identifying (e.g., diagnosing) that a subject suffers from the particular condition, and applying the stimulation in response to the identifying. For example, the methods described herein may comprise identifying that a patient suffers from gastroparesis, and applying any of the stimulation techniques described herein responsively to the identifying. Techniques for diagnosing the conditions described herein are well known in the medical art.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. Provisional Patent Application 60/259,925, filed Jan. 5, 2001, entitled, "Regulation of eating habits";

PCT Patent Application PCT/IL02/00007, filed Jan. 3, 2002, entitled, "Regulation of eating habits," which published as PCT Publication WO 02/053093;

PCT Patent Application PCT/IL00/00132, filed Mar. 5, 2000, entitled, "Blood Glucose Level Control," which published as PCT Publication WO 00/53257, and U.S. patent application Ser. No. 09/914,889 in the national stage thereof, which issued as U.S. Pat. No. 7,006,871, and U.S. patent application Ser. No. 11/318,845, which is a division thereof;

PCT Patent Application PCTIL00/00566, filed Sep. 13, 2000, entitled, "Blood Glucose Level Control," which published as PCT Publication WO 01/66183, and U.S. patent application Ser. No. 10/237,263, filed Sep. 5, 2002, which is a continuation-in-part thereof, and which issued as U.S. Pat. No. 8,019,421;

PCT Patent Application PCT/IL03/000736, filed Sep. 4. 2003, entitled, "Blood Glucose Level Control," which published as PCT Publication WO 2004/021858, and U.S. patent application Ser. No. 10/526,708 in the national stage thereof, which published as US Patent Application Publication 2006/0085045 and U.S. patent application Ser. No. 10/804,560, filed Mar. 18, 2004, which is a continuation-in-part thereof, and which published as US Patent Application Publication 2004/0249421;

PCT Patent Application PCT/IL04/000797, filed Sep. 5, 2004, entitled, "Blood Glucose Level Control," which published as PCT Publication WO/2005/023081, and U.S. patent application Ser. No. 10/570,576 in the national stage thereof, which published as US Patent Application Publication 2007/0156177;

PCT Patent Application PCT/IL04/000664, filed Jul. 21, 2004, entitled, "Gastrointestinal methods and apparatus for use in treating disorders and controlling blood sugar," which published as PCT Publication WO/2005/007232;

U.S. patent application Ser. No. 09/734,358, filed Dec. 21, 2000, entitled, "Acute and chronic electrical signal therapy for obesity," which issued as U.S. Pat. 6,600,953;

PCT Patent Application PCT/IL05/000904, filed Aug. 18, 2005, entitled, "Monitoring, analysis, and regulation of eating habits," which published as WO06/018851, and U.S. patent application Ser. No. 11/573,722 in the national stage thereof, which published as US Patent Application Publication 2009/0118797;

US Provisional Patent Application 60/602,550, filed Aug. 18, 2004, entitled, "Monitoring, analysis, and regulation of eating habits";

PCT Patent Application PCT/IL2007/000052 to Levi et al., filed Jan. 14, 2007, entitled, "Electrode assemblies, tools, and methods for gastric wall implantation," which published as PCT Publication WO 07/080595;

PCT Patent Application PCT/IL12006/000198 to Ben-Haim, filed Feb. 15, 2006, entitled, "Charger with data transfer capabilities," which published as PCT Publication WO 06/087712, and U.S. patent application Ser. No. 11/816,574 in the national stage thereof, which published as US Patent Application Publication 2012/0101.874:

PCT Patent Application PCT/IL2005/000316 to Harel et. al., filed Mar. 18, 2005, entitled, "Gastrointestinal methods and apparatus for use in treating disorders and controlling blood sugar," which published as PCT Publication WO 05/087310, and U.S. patent application Ser. No. 10/599,015 in the national stage thereof, which published as US Patent Application Publication 2009/0088816:

PCT Patent: Application PCT/IL2004/000550 to Ben-Haim et al., filed Jun. 20, 2004, entitled. "Gastrointestinal methods and apparatus for use in treating disorders," which published as PCT Publication WO 04/112563, and U.S. patent application Ser. No. 10/561,491 in the national stage thereof. which issued as U.S. Pat. 7,502.649;

PCT Patent Application PCT/IL2006/000204, filed Feb. 16. 2006, entitled, "Non-immediate Effects of Therapy," which published as PCT Publication WO 2006/087717. and U.S. patent application Ser. No. 11/884,389 in the national stage thereof, which published as US Patent Application Publication 2009/0131993;

PCT Patent Application PCT/US05/044557, filed Dec. 9, 2005, entitled, "Protein Activity Modification," which published as PCT Publication WO/2006/073671, and U.S. patent application Ser. No. 11/792,811 in the national stage thereof, which published as US Patent Application Publication 2009/0292324;

PCT Patent Application PCT/US06/17281, filed May 4, 2006, entitled, "Protein Activity Modification," which published as PCT Publication WO 2006/119467, and U.S. patent application Ser. No. 11/919,491 in the national stage thereof, which published as US Patent Application Publication 2010/0016923, and U.S. patent. application Ser. No. 11/802,685, filed May 25, 2007, which is a continuation-in-part thereof, and which published as US Patent Application Publication 2007/0293901;

PCI Patent. Application PCT/US2006/010911 to Policker et al., tiled Mar. 24, 2006, entitled, "Wireless leads for gastrointestinal tract applications," which published as PCT Publication WO 06/102626, and U.S. patent application Ser. No. 11/909,501, filed Sep. 24, 2007 in the national stage thereof, which published as US Patent Application Publication 2010/0228105:

PCT Patent Application PCT/IL2006/000644 to Policker et al., filed Jun. 4. 2006, entitled. "GI lead implantation," which published as PCT Publication WO 06/129321;

US Provisional Patent Application 60/916,919 filed May 9. 2007. entitled, "Analysis and regulation of food intake";

US Provisional Application 61/051,901, filed May 9, 2008, entitled, "Optimization of filters and parameters for eating detection";

PCT Patent Application PCT/IL08/000646, filed May 11, 2008, entitled, "Analysis and regulation of food intake," which published as PCI Publication WO 08/139461 and U.S. patent application Ser. No. 12/599,350 in the national stage thereof. which published as US Patent Application Publication 2010/0305468: and/or U.S. patent application Ser. No. 12/256,819, filed Oct. 23, 2008, entitled, "Optimization of thresholds for eating detection " which published as US Patent Application Publication 2009/0281449.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for treating a human patient, comprising:
implanting one or more electrode contact surfaces in contact with a fundus of the patient;
providing a control unit coupled to the electrode contact surfaces; and
activating the control unit to drive the electrode contact surfaces to apply an electrical signal to at least one fundic site of the patient that chronically improves a blood glucose level of the patient, in order to treat the patient, (a) without sensing eating by the patient, and (b) without detecting a characteristic of food eaten by the patient by calculating an impedance of tissue of the fundus based on a sensed parameter that varies in response to the electrical signal.

2. The method according to claim 1, wherein activating comprises configuring the control unit to apply the signal to the at least one fundic site at least intermittently during a period having a duration of at least one week, without applying any electrical signals to any antral, sites of the patient during the period.

3. The method according to claim 1, wherein implanting the electrode contact surfaces and activating the control unit comprises identifying that the patient suffers from hypertension, and implanting and activating in response to the identifying.

4. The method according to claim 1, wherein activating the control unit comprises activating the control unit to drive the electrode contact surfaces to apply the electrical signal to the at least one fundic site of the patient that chronically improves the blood glucose level of the patient, in order to treat the patient, without the control unit applying, or generating a signal for applying, any additional glucose-control or weight-control therapy to the patient.

5. A method for treating a human patient, comprising:
identifying that the patient might experience a chronic improvement in a blood glucose level in response to application of an electrical signal to at least one fundic site of the patient; and
in response to identifying:
implanting one or more electrode contact surfaces in contact with a fundus of the patient;
providing a control unit coupled to the electrode contact surfaces; and
activating the control unit to drive the electrode contact surfaces to apply the electrical signal to the at least one fundic site of the patient that chronically improves the blood glucose level of the patient, in order to treat the patient, without sensing eating by the patient.

6. The method according to claim 5, wherein implanting the one or more electrode contact surfaces in contact with the fundus of the patient comprises:
endoseopically making one or more incisions through a fundic wall of the patient; and
via exactly one of the one or more incisions, implanting the one or more electrode contact surfaces in contact with the fundus of the patient.

7. The method according to claim 6, wherein providing the control unit comprises implanting the control unit in a body of the patient via the exactly one of the one or more incisions.

8. The method according to claim 7, wherein providing the control unit comprises providing the control unit sized such that at least one line that passes from edge to edge of the control unit through the center of gravity thereof has a length of no more than 2 cm.

9. The method according to claim 8, wherein the length is no inure than 1 cm.

10. The method according to claim 6, wherein making the one or more incisions and implanting comprise making the one or more incisions and implanting during a surgical implantation procedure having a duration of no more than 45 minutes.

11. The method according to claim 5,
wherein activating the control unit to drive the electrode contact surfaces to apply the electrical signal to the at least one fundic site of the patient that chronically improves the blood glucose level of the, patient comprises activating the control unit to drive the electrode contact surfaces to apply the electrical signal to the at least one fundic site of the patient that chronically improves the blood glucose level of the patient during signal-application periods, and
further comprising activating the control unit to provide reduced-signal-application periods, which alternate with the signal-application periods, and during which the electrode contact surfaces apply the electrical signal having an average energy current that is less than 20% of the average energy of the electrical signal applied during the signal-application periods,
wherein the control unit provides one or more of the reduced-signal-applications periods during every 24-hour period, each of which reduced-signal-application periods has a duration of at least 30 minutes.

12. The method according to claim 11, wherein the reduced-signal-application periods are non-signal-application periods, and wherein activating comprises configuring the control unit to withhold applying the electrical signal during the non-signal-application periods.

13. The method according to claim 5, wherein activating the control unit comprises activating the control unit to drive the one or more electrode contact surfaces using no more than 5 J over a 24-hour period.

14. The method according to claim 5, wherein implanting the one or more electrode contact surfaces comprises implanting exactly one implantable electrode structure that includes the one or more electrode contact surfaces.

15. The method according to claim 5, wherein implanting the one or more electrode contact surfaces comprises implanting the one or more electrode contact surfaces in physical contact with muscle tissue of the fundic site.

16. The method according to claim 15, wherein implanting the one more electrode contact surfaces comprises positioning the one or more electrode contact surfaces within the muscle tissue.

17. The method according to claim 5, wherein implanting the electrode contact surfaces and activating the control unit comprises identifying that the patient suffers from diabetes, and implanting and activating in response to the identifying 18. The method according to claim 5, wherein implanting the electrode contact surfaces and activating the control unit comprises identifying that the patient suffers from metabolic syndrome, and implanting and activating in response to the identifying.

19. The method according to claim 5, wherein implanting the electrode contact surfaces and activating the control unit comprises identifying that the patient might experience an improvement in the blood glucose level in response to applying the signal, and implanting and activating in response to identifying.

20. The method according to claim 5, wherein activating comprises configuring one or more parameters of the electrical signal to cause a reduction in a fasting glucose blood level of the patient.

21. The method according to claim 5, wherein activating comprises configuring one or more parameters of the electrical signal to cause a reduction in postprandial glucose level of the patient.

22. The method according to claim 5, wherein activating comprises configuring one or more parameters of the electrical signal to cause an improvement in a level at least one hormone selected from the group consisting of: at least one hormone associated with glycemic control, and at least one hormone associated with a metabolic disorder.

23. The method according to claim 22, further comprising assessing the level of the at least one hormone after activating the control unit.

24. The method according to claim 22, wherein the improvement in the level of the at least one hormone includes a normalization of at least one element selected from the group consisting of: secretion of the at least one hormone, expression of the at least one hormone, and a blood level of the at least one hormone.

25. The method according to claim 22, wherein configuring comprises configuring the one or more parameters of the electrical signal to simultaneously cause the improvement in levels of a plurality of hormones.

26. The method according to claim 22, wherein the at least one hormone is secreted by a stomach of the patient.

27. The method according to claim 26, wherein the at least one hormone is secreted by the fundus.

28. The method according to claim 26, wherein the at least one hormone is secreted by an antrum of the stomach.

29. The method according to claim 22, wherein the at least one hormone is secreted by an organ of the patient selected from the group of organs consisting of: a duodenum of the patient, and a pancreas of the patient.

30. The method according to claim 22, wherein the improvement is an improvement selected from the group of improvements consisting of: improvement in a postprandial level of the at least one hormone, and an improvement in a fasting level of the at least one hormone.

31. The method according claim 30, wherein the improvement includes an improvement selected from the group of improvements consisting of: an improvement in a postprandial level of insulin, and an improvement in a fasting level of insulin.

32. The method according to claim 30, wherein the improvement includes an improvement selected from the group of improvements consisting of: an improvement in a postprandial level of ghrelin, an improvement in a fasting level of ghrelin, an improvement in a postprandial level of glucagon, an improvement in a postprandial level of pancreatic polypeptide, an improvement in a fasting level of pancreatic polypeptide, an improvement in a postprandial level of glucagon-like peptide-1 (GLP-1), and an improvement in a postprandial level of C-peptide.

33. The method according to claim 5, wherein implanting the electrode contact surfaces and activating the control unit comprises identifying that the patient might experience an improvement in a level at least one hormone in response to applying the signal, and implanting and activating in response to identifying, wherein the at least one hormone is selected from the group consisting of: at least one hormone associated with glycemic control, and at least one hormone associated with a metabolic disorder.

34. The method according to claim 33, wherein the improvement in the level of the at least one hormone includes a normalization of at least one element selected from the group consisting of: secretion of the at least one hormone, expression of the at least one hormone, and a blood level of the at least one hormone.

35. The method according to claim 33, wherein the improvement is a simultaneous improvement in levels of a plurality a hormones.

36. The method according to claim 33, wherein the at least one hormone is secreted by an organ of the patient selected from the group of organs consisting of: a stomach of the patient, the fundus, an antrum of the stomach, a duodenum of the patient, and a pancreas of the patient.

37. The method according to claim 33, wherein the improvement is an improvement selected from the group of improvements consisting of: an improvement in a postprandial level of the at least one hormone, and an improvement in a listing level of the at least one hormone.

38. The method according to claim 33, wherein the improvement includes an improvement selected from the group of improvements consisting of: an improvement in a postprandial level of insulin, and an improvement in a fasting level of insulin.

39. The method according to claim 37, wherein the improvement includes an improvement selected from the group a improvements consisting of: an improvement in a postprandial level of ghrelin, an improvement in a fasting level of ghrelin, an improvement in a postprandial level of glucagon, an improvement in a postprandial level of pancreatic polypeptide, an improvement in a fasting level of pancreatic polypeptide, an improvement in a postprandial level of glucagon-like peptide-1 (GLP-1) and an improvement in a postprandial level of C-peptide.

40. The method according to claim 5, further comprising assessing blood glucose level control by measuring a level of HbA1c of the patient after activating the control unit.

41. The method according to claim 5, further comprising assessing blood glucose level improvement by measuring the blood glucose level after activating the control unit.

42. The method according to claim 5, wherein activating comprises configuring one or more parameters of the electrical signal to not cause hypoglycemia of the patient.

43. The method according to claim 42, wherein configuring the one or more parameters of the electrical signal to not cause the hypoglycemia does not comprise measuring the blood glucose level of the patient.

44. The method according to claim 5, wherein activating comprises configuring the control unit to apply the signal in a series of pulses having an energy per pulse of no more than 5 microjoules.

45. The method according to claim 5, wherein activating comprises configuring the control unit to apply the signal in a series of pulses having an average energy per pulse of no more than 5 microjoules.

46. The method according to claim 5, wherein activating comprises configuring the control unit to apply the signal having an instantaneous power of no more than 100 milliwatts.

47. The method according to claim 5, wherein activating comprises configuring the control unit to apply the signal in a series of pulses, at least one of which pulses has an amplitude of between 5 mA and 35 mA.

48. The method according to claim 5, wherein activating comprises configuring the control unit to apply the signal for at least three months.

49. The method according to claim 5, wherein activating the control unit comprises activating the control unit to drive the electrode contact surfaces to apply the electrical signal to the at least one fundic site of the patient that chronically improves the blood glucose level of the patient, in order to treat the patient, without detecting a characteristic of food eaten by the patient by calculating an impedance of tissue of the fundus based on a sensed parameter that varies in response to the electrical signal.

50. The method according to claim 5, wherein activating the control unit comprises activating the control unit to:
during first and second modes of operation, drive the electrode contact surfaces to apply the electrical signal to the at least one fundic site of the patient, and configuring one or more parameters of the electrical signal to chronically improve the blood glucose level of the patient, in order to heat the patient, and
during the first mode, and not during the second mode, sense a parameter that varies in response to the applied electrical signal, and calculate, based on the sensed parameter, an impedance of tissue of the fundus.

51. The method according to claim 5, wherein activating the control unit comprises activating the control unit to drive the electrode contact surfaces to apply the electrical signal to the at least one fundic site of the patient that chronically improves the blood glucose level of the patient, in order to treat the patient, without the control unit applying, or generating a signal for applying, any additional glucose-control or weight-control therapy to the patient.

52. The method according to claim 5, wherein implanting the electrode contact surfaces and activating the control unit comprises identifying that the patient suffers from hypertension, and implanting and activating in response to the identifying.

53. A method for treating a human patient, comprising:
identifying that the patient might experience a chronic improvement in a blood glucose level in response to application of an electrical signal to at least one fundic site of the patient; and
in response to identifying:
implanting one or more electrode contact surfaces in contact with a fundus of the patient;
providing a control unit coupled to the electrode contact surfaces; and
activating the control unit to drive the electrode contact surfaces to apply the electrical signal to the at least one fundic site of the patient that chronically improves the blood glucose level of the patient, in order to treat the patient,
wherein activating comprises configuring the control unit to (a) apply the signal in a series of pulses, at least one of which pulses has a duration of no more than 5 milliseconds, and (b) configure the pulses to have an average energy per pulse of no more than 50 microjoules.

54. The method, according to claim 53, wherein the duration is between 2 microseconds and 5 milliseconds.

55. The method according to claim 53, wherein the duration is no more than 1 millisecond.

56. The method according to claim 55, wherein the duration is no more than 100 microseconds.

57. The method according to claim 53, wherein implanting the electrode contact surfaces and activating the control unit comprises identifying that the patient suffers from hypertension, and implanting and activating in response to the identifying.

58. A method for treating a human patient, comprising;
- implanting one or more electrode contact surfaces in contact with a fundus of the patient;
- providing a control unit coupled to the electrode contact surfaces; and
- activating the control unit to drive the electrode contact surfaces to apply an electrical signal, as a plurality of pulses, to at least one fluidic site of the patient that chronically improves a blood glucose level of the patient, in order to treat the patient, (a) without detecting eating by the patient by calculating impedance of tissue of the fundus based on a sensed parameter that varies in response to the electrical signal, and (b) without detecting a characteristic of food eaten by the patient by calculating impedance of tissue of the fundus based on a sensed parameter that varies in response to the electrical signal,
- wherein one or more of the pulses have a pulse width of no more than 5 milliseconds.

59. The method according to claim 58, wherein the duration is between 2 microseconds and 5 milliseconds.

60. The method according to claim 58, wherein the duration is no more than 1 millisecond.

61. The method according to claim 60, wherein the duration is no more than 100 microseconds.

62. The method according to claim 58, wherein activating comprises configuring the control unit to configure the pulses to have an average energy per pulse of no more than 50 microjoules.

63. The method according to claim 58, wherein activating comprises configuring the control unit to generate the electrical signal using no more than 5 J over a 24-hour period.

64. The method according to claim 58, wherein implanting the electrode contact surfaces and activating the control unit comprises identifying that the patient suffers from hypertension, and implanting and activating in response to the identifying.

65. A method for treating a human patient, comprising:
- identifying that the patient might experience a chronic improvement in a blood glucose level in response to application of an electrical signal to at least one fundic site of the patient; and
- in response to identifying:
  - implanting one or more electrode contact surfaces in contact with a fundus of the patient;
  - providing a control unit coupled to the electrode contact surfaces; and
  - activating the control unit to drive the electrode contact surfaces to apply the electrical signal to the at least one fundic site of the patient that chronically improves the blood glucose level of the patient, in order to treat the patient,
- wherein activating the control unit comprises (a) configuring the control unit to apply the signal in series of pulses, at least one of which pulses has a duration of no more than 5 milliseconds, and (b) activating the control unit to drive the one or more electrode contact surfaces using no more than 5 J over a 24-hour period.

66. The method according to claim 65, wherein activating comprises configuring the control unit to configure the pulses to have an average energy per pulse of no more than 50 microjoules.

* * * * *